United States Patent [19]
Hemminger et al.

[11] Patent Number: 5,297,288
[45] Date of Patent: Mar. 22, 1994

[54] SYSTEM FOR USE WITH A HIGH RESOLUTION SCANNER FOR SCHEDULING A SEQUENCE OF SOFTWARE TOOLS FOR DETERMINING THE PRESENCE OF BANDS IN DNA SEQUENCING SAMPLES

[75] Inventors: Robert W. Hemminger, Oberlin; Robert J. Emery, Wakeman, both of Ohio

[73] Assignee: United States Biochemical Corporation, Cleveland, Ohio

[21] Appl. No.: 897,606

[22] Filed: Jun. 10, 1992

Related U.S. Application Data

[60] Continuation of Ser. No. 640,471, Jan. 15, 1991, abandoned, which is a division of Ser. No. 442,553, Nov. 28, 1989, abandoned.

[51] Int. Cl.$^5$ .............. G06F 9/44; G06F 13/10; G06F 15/42; G06F 15/70
[52] U.S. Cl. ................. 395/700; 364/223.3; 364/281.8; 364/DIG. 1; 364/924; 435/6
[58] Field of Search ............ 364/200, 900; 395/700; 435/6

[56] References Cited

U.S. PATENT DOCUMENTS

| | | | |
|---|---|---|---|
| 4,103,287 | 7/1978 | Frank | 382/56 |
| 4,107,648 | 8/1978 | Frank | 382/56 |
| 4,122,518 | 10/1978 | Castleman et al. | 364/300 |
| 4,163,212 | 7/1979 | Buerger et al. | 382/8 |
| 4,404,683 | 9/1983 | Kobayashi et al. | 382/6 |
| 4,642,763 | 2/1987 | Cummins | 364/300 |
| 4,718,090 | 1/1988 | Cooper, Jr. | 382/26 |
| 4,831,580 | 5/1989 | Yamada | 364/900 |
| 4,888,695 | 12/1989 | Shtraishi et al. | 364/413.01 |
| 4,958,281 | 9/1990 | Hara | 364/413.01 |
| 4,980,827 | 12/1990 | Hara | 364/413.01 |
| 5,072,382 | 12/1991 | Kamentsky | 364/413.08 |
| 5,107,422 | 4/1992 | Kamentsky et al. | 364/413.08 |

*Primary Examiner*—Thomas C. Lee
*Assistant Examiner*—Peter Y. Wang
*Attorney, Agent, or Firm*—Lyon & Lyon

[57] ABSTRACT

Method for optically scanning an object comprising a flat support for holding the object; a linear optical sensor held in a fixed position on one side of the support; a light source held in a fixed position on the other side of the support for projecting light through the object toward the optical sensor; and a drive mechanism for moving the object along one direction to successive scanning positions. The user may create custom application computer programs for performing desired image scanning and analysis on an object. To enable this, the system stores software tools each capable of performing an image scanning or image analysis function, stores an interpreter program corresponding to a natural language identifiers for the functions, and provides an interactive computer environment for the user to specify a sequence of software tools using the natural language identifiers to be executed to perform the desired image scanning and analysis.

1 Claim, 58 Drawing Sheets

Microfiche Appendix Included
(10 Microfiche, 820 Pages)

```
select program action                    [cancel]

action              description
scan sample         scan a sample
create window       create a womdpw
image reduction     make a reduced view of image
find spots          create a list of spots
```

FIG. 16F

```
[file] [return] comment middle x @y 200 x axis
  start (mm) 100      end (mm) 240      reduction power 0 y axis
  start (mm) 200      end (mm) 225      reduction power 0
  normalize (mm) 0         post (mm) 0 data storage
  resolution normal        view during scan no other
  lamp transmittance
```

FIG. 16G

```
file view return comment big window px1  0                    py1 100
px2 400                   py2 400
background color bright_white
border color border_color
border width 5
save background no
magnification x 0     y 0
center x 2500  y 10
```

FIG. 16H

```
                                    cancel black          dark_gray        menu_text_color
blue           light_blue       hotkey_text
green          light_green      warning_text
cyan           light_cyan       help_text
red            light_red        black
magenta        light_magenta    background_color
brown          yellow           cursor_color
white          bright_white     border_color
none
```

FIG. 16I

```
                                    cancel reduction    resulting
      power     image size
        0       1X of original
       -1       2X of original
       -2       4X of original
       -3       8X of original
       -4      16X of original
       -5      32X of original
       -6      64X of original
```

FIG. 16J

```
 up down top end cancel  reduction parameters

DEFAULT  creates half size image
REDUC4T  creates 1/4 size image
```

FIG. 16K

```
result          select item to use as input              cancel  ↑
file  action 001    scan sample                         middle 80 mm, 25 mm long
002      image reduction                   creates half size image

```
file  return comment default spot parameters delta x half size 15
delta x threshold 15
rise count min 10
fall count min 10
entity length max 15
average O.D. min 4
spot area min 50
spot O.D. min 3
's' factor 2
```

FIG. 16O

```
program windows go done  f3=printscrn  f1=help
point to window and click         cancel
```

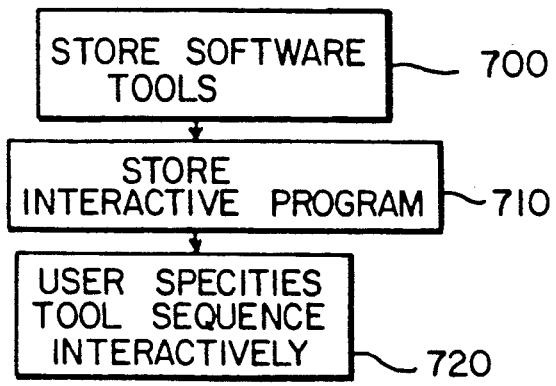
FIG. 17A
FIG. 17B
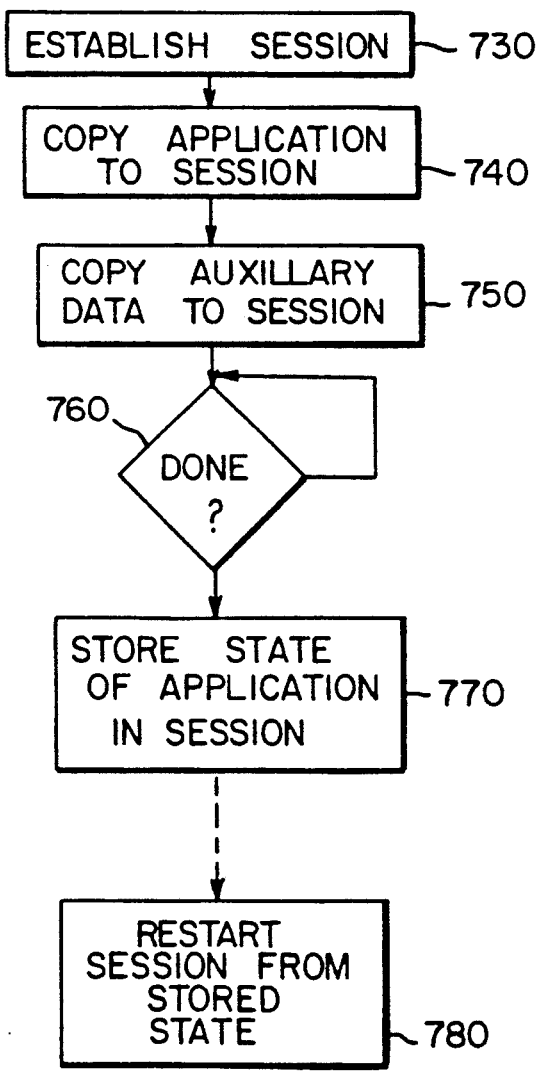

SYSTEM FOR USE WITH A HIGH RESOLUTION SCANNER FOR SCHEDULING A SEQUENCE OF SOFTWARE TOOLS FOR DETERMINING THE PRESENCE OF BANDS IN DNA SEQUENCING SAMPLES

CROSS-REFERENCE TO RELATED APPLICATIONS

This application is a continuation of U.S. Ser. No. 07/640,471, filed on Jan. 15, 1991, now abandoned, which is a divisional of U.S. Ser. No. 07/442,553, filed on Nov. 28, 1989, now abandoned.

COPYRIGHT NOTICE

A portion of this disclosure is subject to copyright protection (e.g., the figures and the Microfiche Appendix B). The copyright owner has no objection to the reproduction of the patent document as it appears in the United States Patent and Trademark Office patent file or records, but otherwise reserves all copyright rights whatsoever.

Other embodiments are within the scope of the claims which follow the appendices.

BACKGROUND OF THE INVENTION

This invention relates to optical scanners suitable for analyzing images on a film. For example, such scanners are suitable for analyzing an autoradiographic image of the products of a deoxyribonucleic acid (DNA) sequencing reaction in order to determine the nucleotide base sequence of a DNA molecule.

DNA is a double stranded or single stranded polymeric molecule formed by covalent joining of the four deoxynucleotide bases, namely, adenine (A), guanine (G), thymine (T), and cytosine (C). The sequence of these deoxynucleotide bases determines the utility of a DNA molecule. For example, a DNA molecule may encode a controlling region for another DNA molecule, or may encode a polypeptide or a protein. It is common to determine the deoxynucleotide base sequence of a DNA molecule in a variety of manners. Generally, this process, called DNA sequencing, involves generation of four populations of single-stranded DNA fragments having one defined terminus and one variable terminus. The variable terminus generally terminates at a specific given nucleotide base. The four different sets of fragments are each separated, on the basis of their length, to form bands on a high resolution polyacrylamide gel. Each band on the gel corresponds colinearly to a specific deoxynucleotide base in the DNA sequence, thus identifying the position in the sequence of a given deoxynucleotide base.

The most commonly use method of DNA sequencing is termed dideoxy-sequencing. This method involves enzymatic synthesis of a DNA strand using a DNA polymerase. Generally, four separate synthesis reactions are run, each reaction being caused to terminate at a specific nucleotide base by incorporation of an appropriate chain terminating agent, e.g., a dideoxynucleotide. Enzymes used for dideoxysequencing include the *E. coli* DNA polymerase large fragment (Klenow), reverse transcriptase, T7 DNA polymerase, and Taq DNA polymerase.

Tabor and Richardson 86 Proc. Natl. Acad. Sci. USA 4076, 1989 describe use of a manganese-based buffer (in place of the usual magnesium-based buffer) for a DNA sequencing reaction. Use of manganese results in uniform terminations of DNA sequencing reactions with intensity of adjacent bands on a polyacrylamide gel varying in most instances by less than 10%. They state that this property should be of use for DNA sequencing, particularly by automated procedures.

The normal nomenclature used by persons in this field will be used in this application. Thus, the term "lane" refers to a generally narrow linear band between the top and bottom of an acrylamide gel in which a sample to be electrophoresed is placed and then electrophoresed. A "base" is generally used to refer to a deoxynucleotide base. A "smile" refers to an artifact produced during electrophoresis where the distance traveled by samples within adjacent lanes differs, such that the central lanes in an acrylamide gel will travel further than those on either side, thus creating a curved front in the gel. A "band" refers to the image on an autoradiogram of a DNA product running within a lane at a specific linear position along that lane. DNA products which differ by one or more bases form distinct bands along a lane. In ideal conditions, a band is a rectangular square the width of which is equal to the width of a lane, and the length of which is relatively small such that adjacent bands do not merge.

There follow references to machines designed to aid analysis of products of a DNA sequencing reaction, for example, an autoradiogram resulting from a DNA sequencing reaction. These references are generally based on trade literature. These machines are not admitted to be prior art to the present application.

IntelliGenetics TM literature describes a device for acquiring the image of a DNA sequencing autoradiogram and deciphering the pattern of bands. It is described as being capable of compensating for common defects. For example, it is said to straighten distorted lanes, flatten bands, and minimize smiles even in the same lane set.

UltroScan TM literature is a laser densitometer suitable for scanning autoradiographs, photographs, slab gels, blots, and tube gels. Slab gels and tube gels refer to agarose or polyacrylamide gels formed, respectively, as a flat rectangular gel or within a tube. The literature states that "only a laser can help . . . get the maximum amount of information from today's high resolution separations . . ."

BioRad TM literature describes a video densitometer for analyzing autoradiograms and gels. The system is provided with a 1728 element CCD linear diode array detector, and a light source for transmission or reflectance which illuminates a narrow 20 cm slot. Light from the sample is directed by two mirrors to a lens which focuses the light onto a CCD linear array detector. 1660 elements of the linear array are used to measure the data simultaneously. The sample is placed on a platten controlled by stepper motor. The platten is moved back and forth either automatically or manually. An entire lane of data is illuminated and measured at once.

BioMed Instruments TM literature describes several laser scanning densitometers. A ribbon laser beam suitable for scanning by absorbance or transmittance, is used scan two dimensional gels.

Applied Biosystems TM literature describes a sequencing system using four different fluorescent dye labels each corresponding to one of the four deoxynucleotide bases. The gel is analyzed by a laser light beam which scans the electrophoresis gel.

Molecular Dynamics ™ literature describes a densitometer able to automatically scan an entire sample area. 13,000 density measurements are made on each square centimeter of sample.

Hitachi ™ America literature describes a DNA film scanner. The scanner appears similar to a desk top copier and uses a charge coupled device (CCD).

BioRad ™ literature describes an automatic sequence reader and analysis system. The optical scanner utilizes a charge coupled device. The software is designed to correct for smiling and other electrophoretic artifacts.

BioImage ™ literature describes an instrument able to scan whole gels quickly and automatically. The gel is scanned using a Kodak camera or an optional laser scanner. The camera is a Kodak CCD camera, formed as a two dimensional CCD device having 1024×1024 arrays. Reflective scanning is also possible.

SUMMARY OF THE INVENTION

The invention provides a scanner capable of analyzing DNA autoradiograms, e.g., sequencing autoradiograms, gels stained for analysis of large DNA or RNA fragments (agarose or acrylamide gels), polyacrylamide gels stained for protein analysis, isoelectric focusing gels, Petri dishes containing colonies for counting, and films produced by Northern, Western, and Southern blotting. The scanner also is useful for analysis of products useful in forensic science, for general imaging, for transmittal of scientific or medical information from one location to another, for population screening and diagnosis (including AIDS testing using Western blot, Southern blot, and Northern blot methods and indirect immunofluorescence), and microtitre plate reading. The scanner also is suitable for use in prenatal hemoglobin determination and analysis of seed isoenzymes. The scanner is designed to provide high resolution at low cost with readily available relatively cheap replaceable components.

In general, in one aspect, the invention features apparatus for optically scanning an object comprising a flat support for holding the object; a linear optical sensor held in a fixed position on one side of the support; a light source held in a fixed position on the other side of the support for projecting light through the object toward the optical sensor; and a drive mechanism for moving the object along one direction to successive scanning positions.

Preferred embodiments include the following features. The flat support includes an opaque surface interrupted by a linear aperture for allowing the light to pass from the light source to the object, and a variable shutter mechanism for selectively confirming the linear aperture to a length corresponding to a width of the object. The drive mechanism includes a rotationally driven rod having a high friction surface for engaging one side of the object, and an idler assembly for urging the object against the driven rod. The idler assembly includes (a) an idler wheel for contacting the other side of the object, and (b) a mount for the idler wheel, the mount being pivotally held with respect to the object to permit the idler wheel to selectively make or not make contact with the object. The mount includes a spring for pivoting the mount so that the idler wheel is pressed against the object, and an eccentric cam shaft engaging a surface of the mount and the spring so that rotating the cam shaft selectively applies or removes tension on the spring to cause or not cause the pivoting. The idler assembly provides clearance of at least $\frac{1}{8}''$ above the surface to accommodate objects of any thickness up to $\frac{1}{8}''$.

The drive mechanism includes a controllable motor, the flat support bears an index mark spaced apart from the light source; and the motor is controlled to move the object a predetermined distance from the index mark toward the light source.

In general, in another aspect, the invention features a method for enabling a user to create a custom application computer program for performing desired image scanning and analysis on an object. The method includes storing software tools each capable of performing an image scanning or image analysis function, storing an interpreter program corresponding to a natural language identifiers for the functions, and providing an interactive computer environment for the user to specify a sequence of software tools using the natural language identifiers to be executed to perform the desired image scanning and analysis.

Preferred embodiments include the following features. A session is established for applying the program to image scanning and analysis of a given object, by storing a copy of the program data related to the object, and state information concerning a state of execution of the program as of a given time; the copy of the program is executed using the object data. Execution of the program may be terminated and later restarted in the same state. The interactive computer environment includes displaying information concerning available tools and the information is organized in a hierarchical tree. The information displayed at a given time is sensitive to the current context.

In a preferred aspect, the invention features a method for determining the DNA sequence of a DNA molecule. This method includes the following steps: performing a DNA sequencing reaction in a manganese-based buffer under conditions in which the products of the sequencing reaction are synthesized in uniform amounts and are radioactively labeled; separating the products according to size in a jar; producing an autoradiogram of the products after the separating step; providing the above apparatus; placing the autoradiogram on the flat support; causing the drive mechanism to move the autoradiogram along the one direction and simultaneously causing light to pass through the autoradiogram to the linear optical sensor; and analyzing signals from the sensor. The signals are representative of the DNA sequence of the DNA molecule.

The invention provides an easy to manufacture, easy to maintain, easy to use, high resolution scanner which accommodates objects of a wide variety of widths, lengths, and thicknesses. The user can take advantage of a variety of tools using a simple, easily understood interactive software environment.

A scanner of the present invention provides high resolution analysis of any of a number of formats in the biological and medical sciences, as well as in other sciences. The object to be analyzed may be an autoradiogram, a wet gel, an agarose gel within a Petri dish, or even a microtitre plate. Light may be applied in both transmitting and reflecting formats. Autoradiogram gels of almost any length may be analyzed; the limitation on length is purely one of available computer storage space.

Other features and advantages of the invention will be apparent from the following description of the preferred embodiments thereof, and from the claims.

DESCRIPTION OF THE PREFERRED EMBODIMENT

The drawings will first briefly be described.

DRAWINGS

Figure 7:
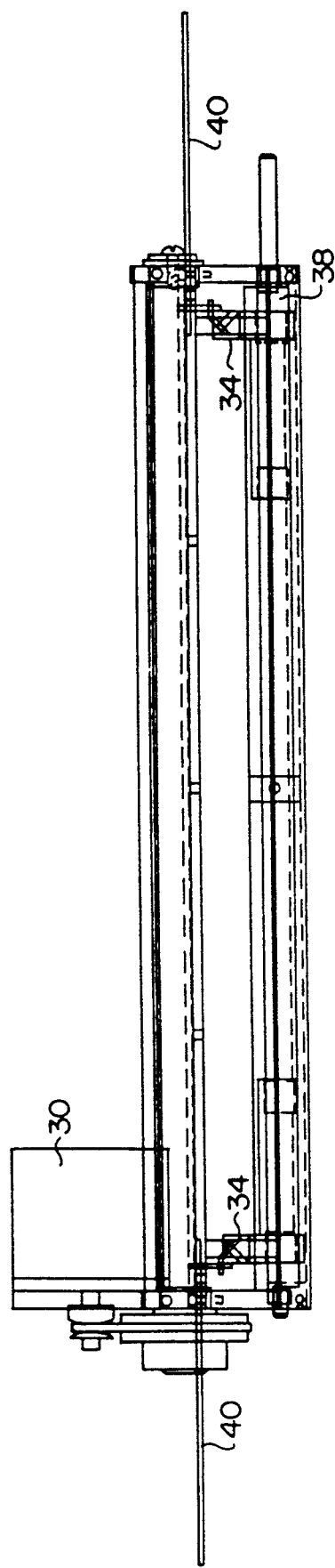
Figure 8:
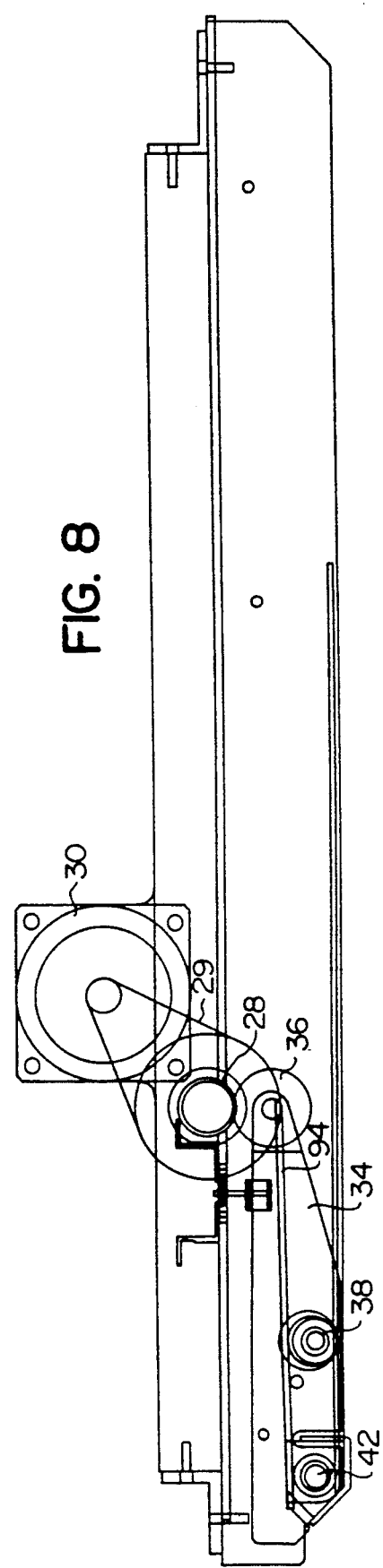
Figure 9:
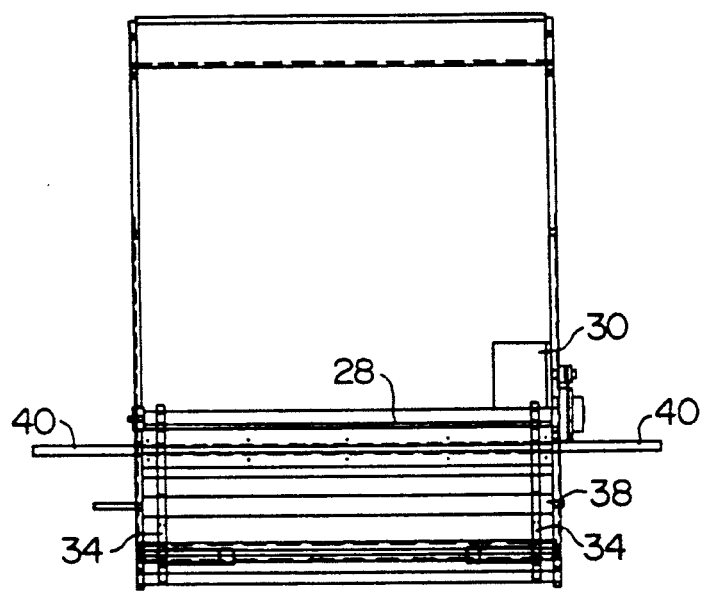
Figure 10A:
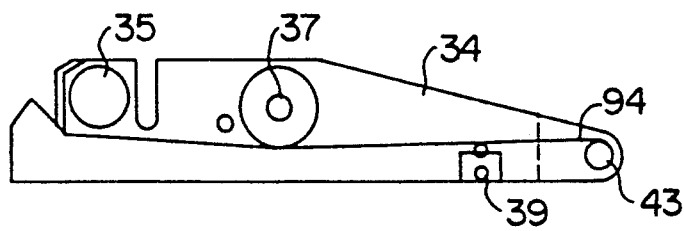
Figure 10B:
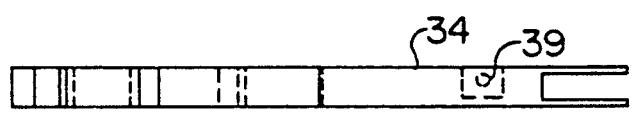
Figure 10C:
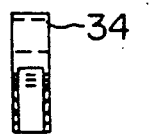
Figure 10D:
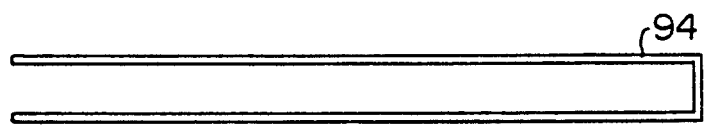
Figure 10E:
Figure 10F:
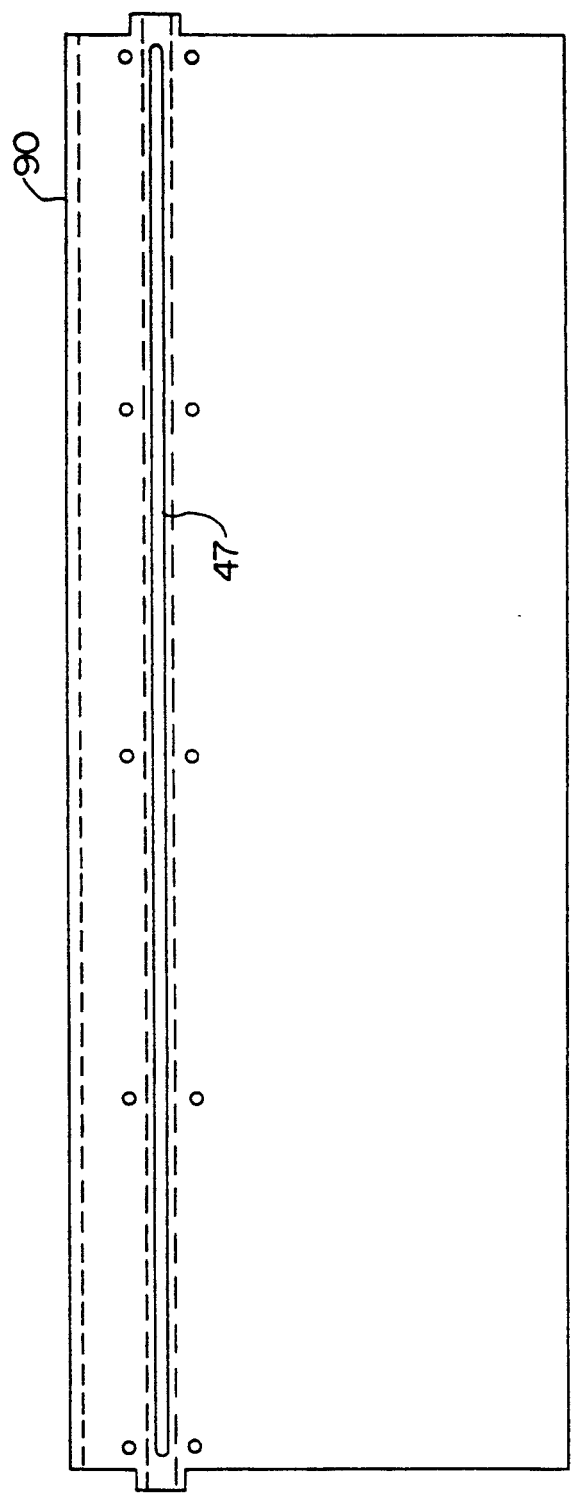
Figure 10G:
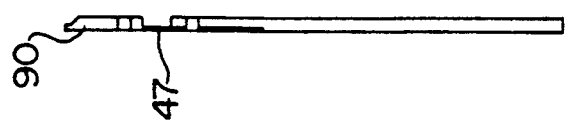
Figure 10H:
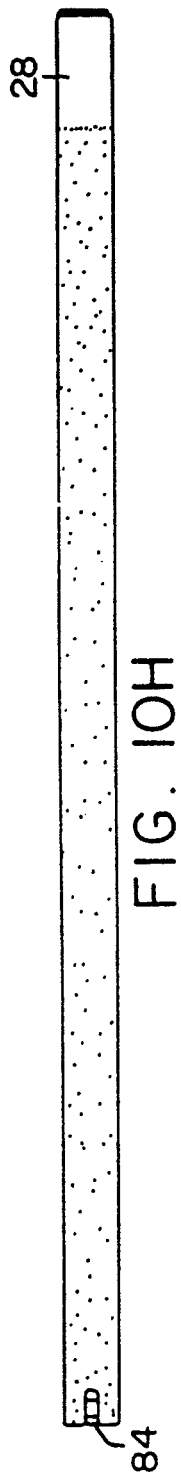
Figure 10I:
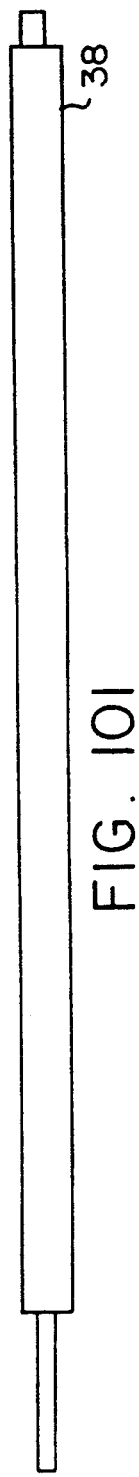
Figure 10J:
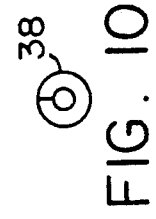
Figure 10K:
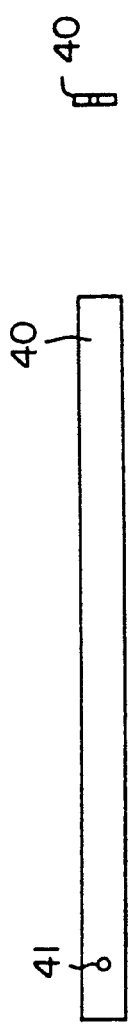
Figure 10L:
Figure 11:
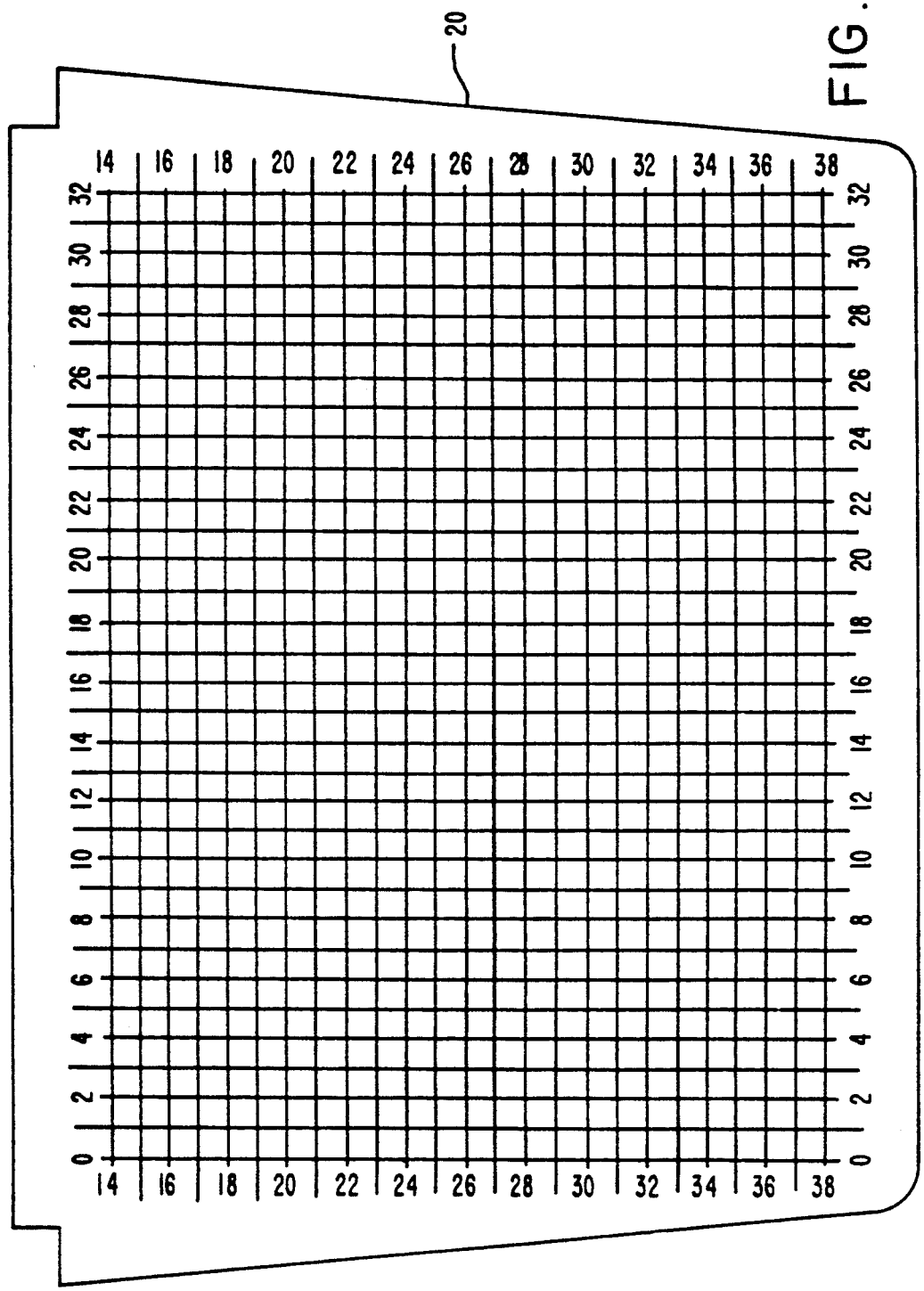
Figures 1, 12A:
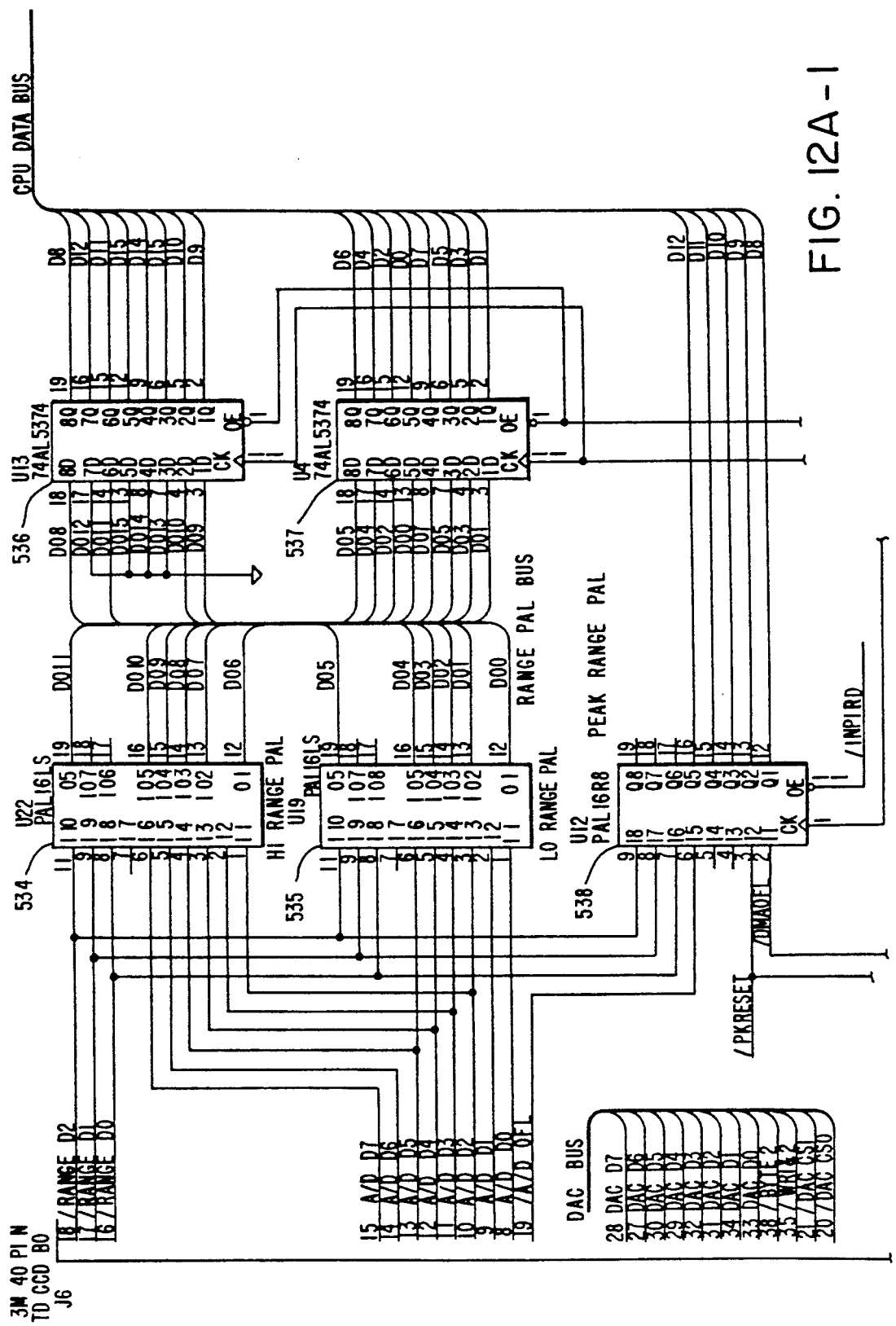
Figures 2, 12A:
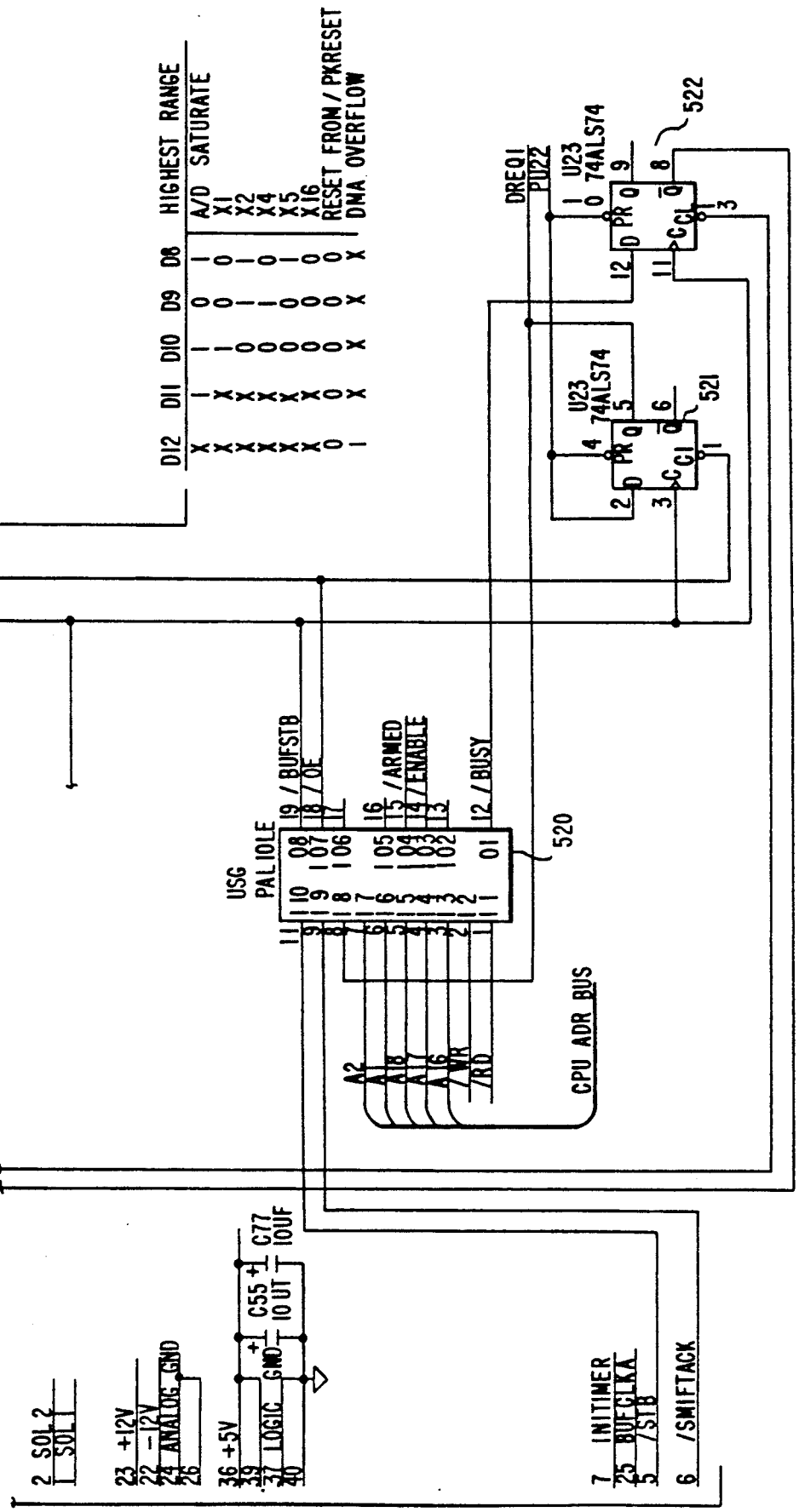
Figures 3, 12A:
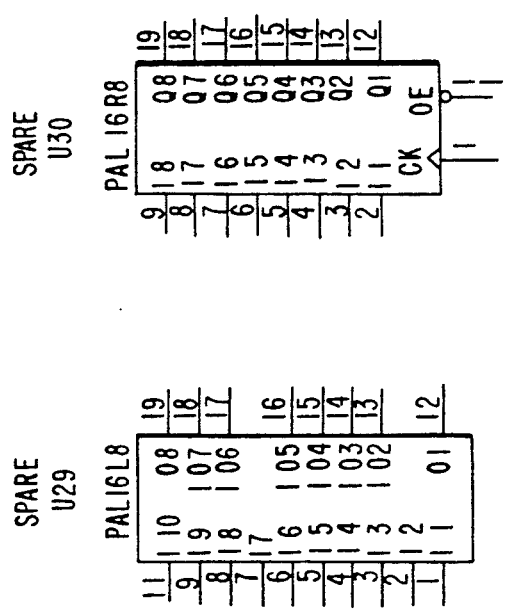
Figures 1, 12B:
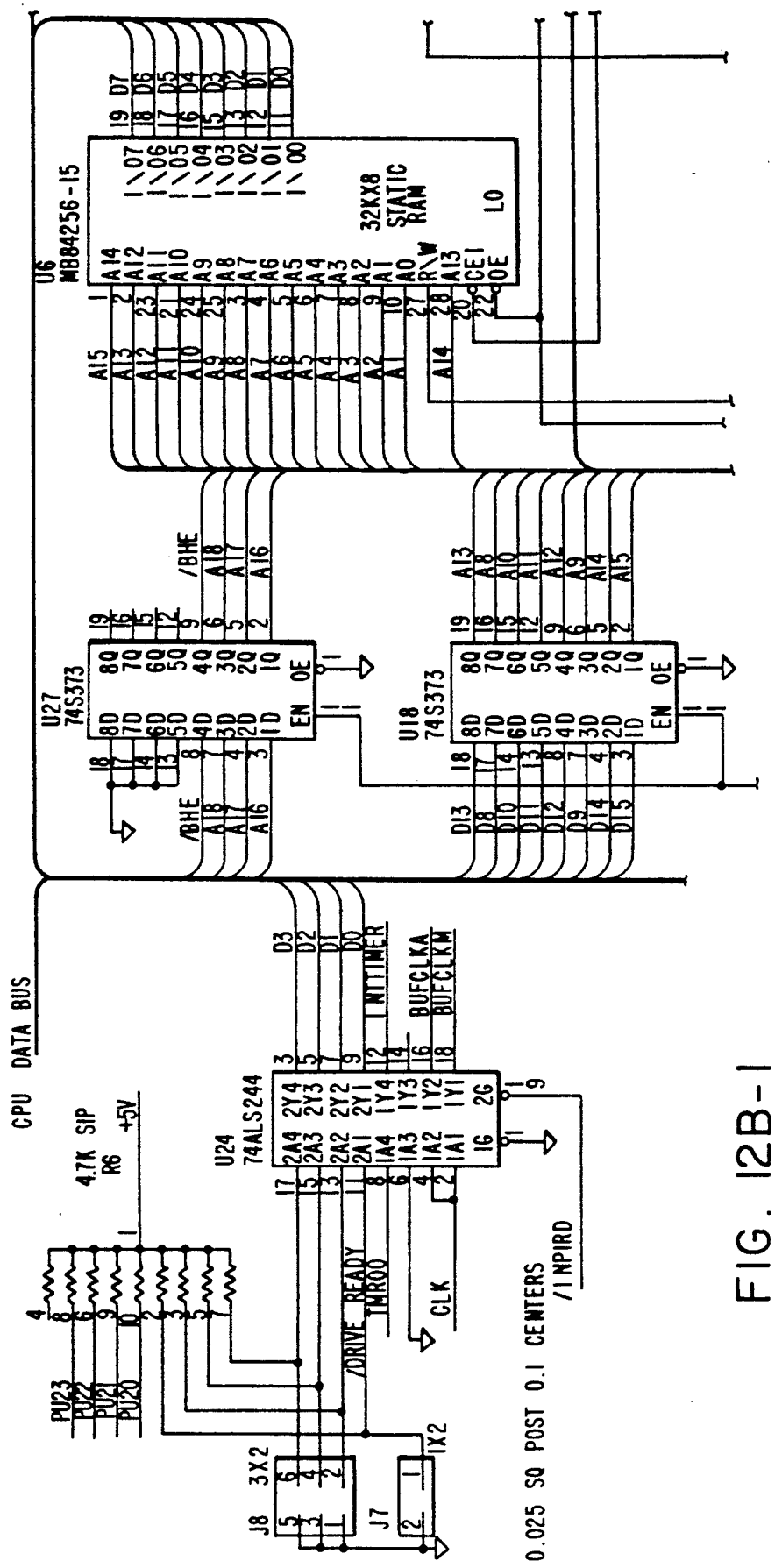
Figures 2, 12B:
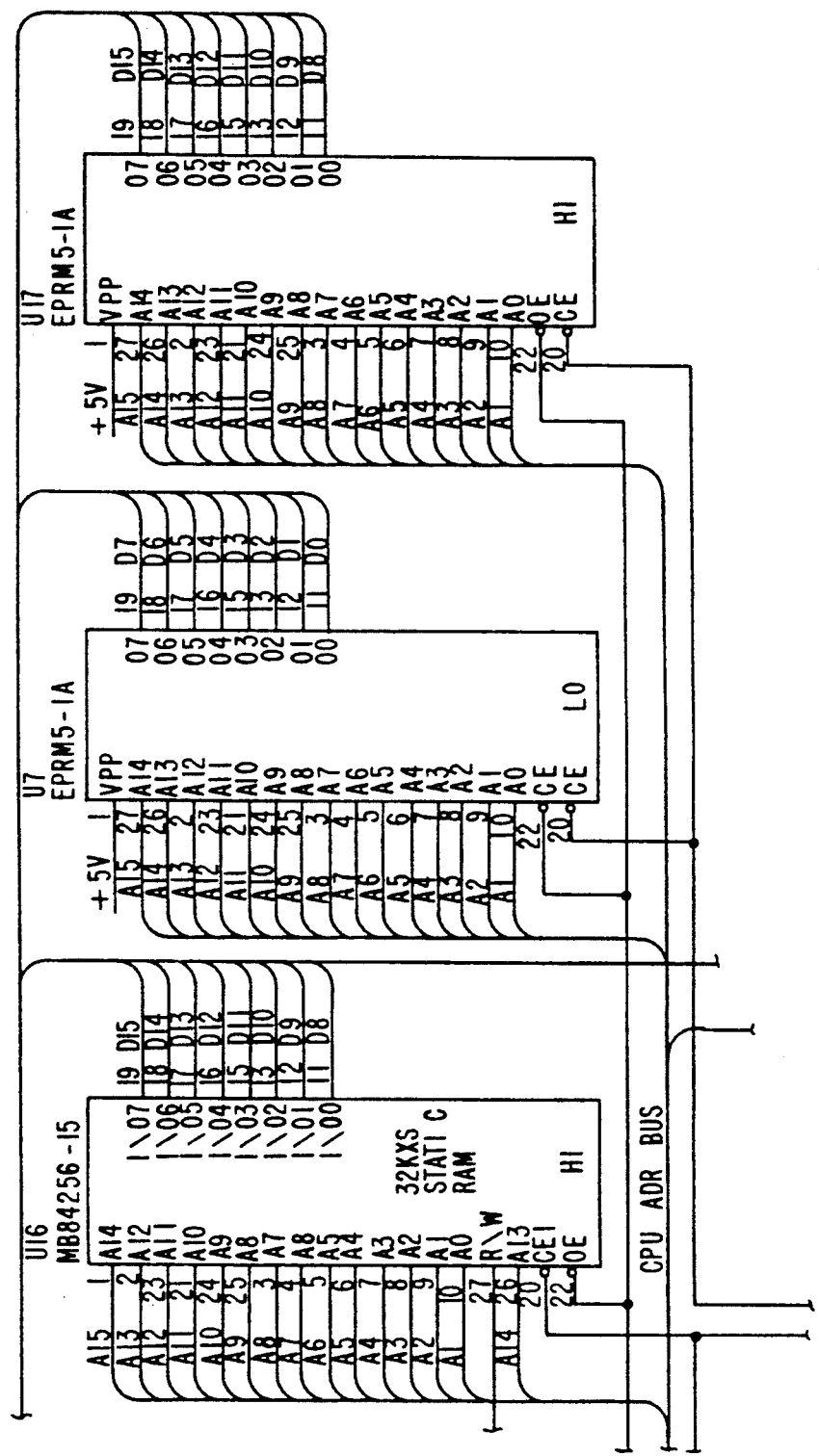
Figures 3, 12B:
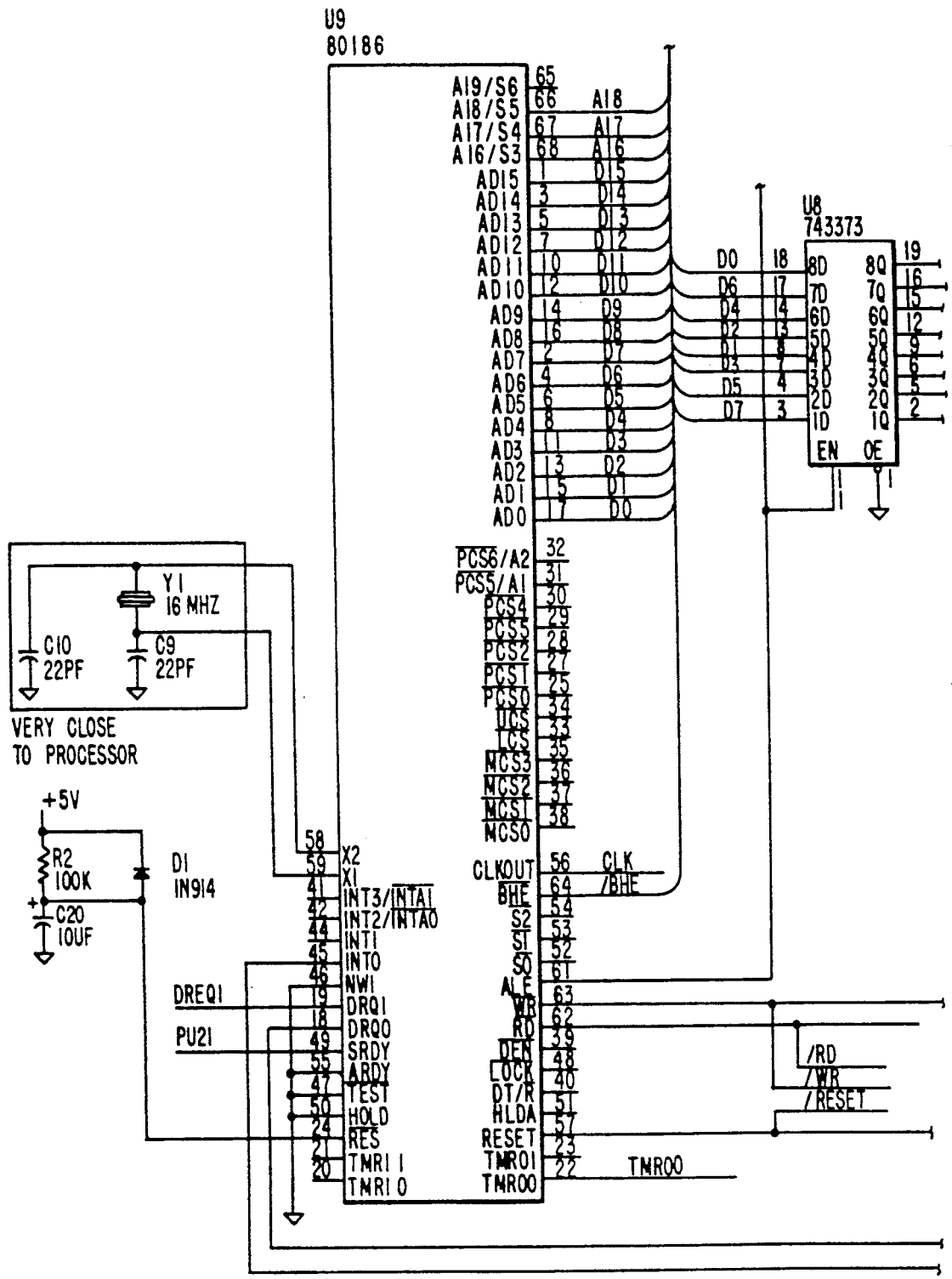
Figures 4, 12B:
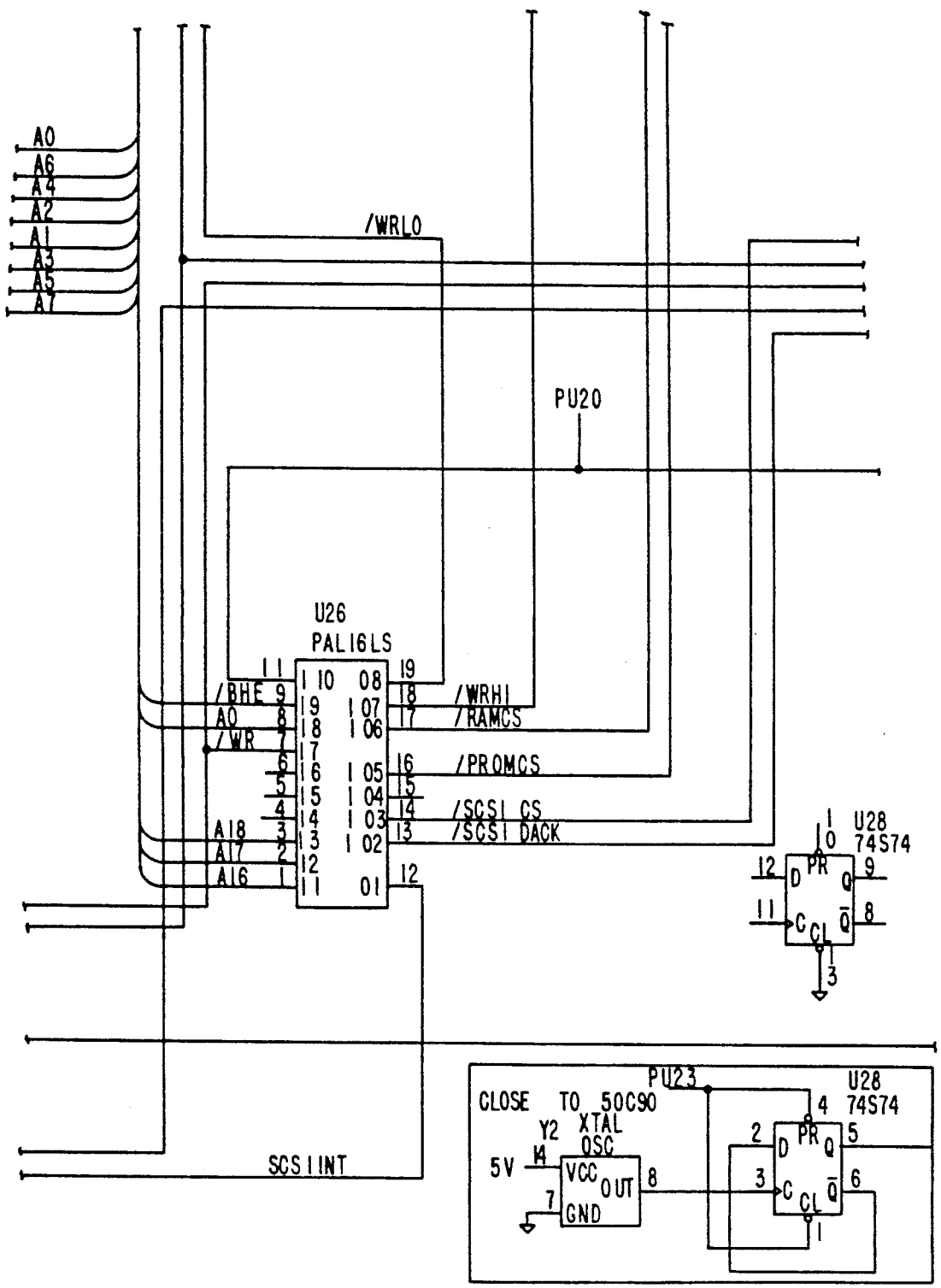
Figures 5, 12B:
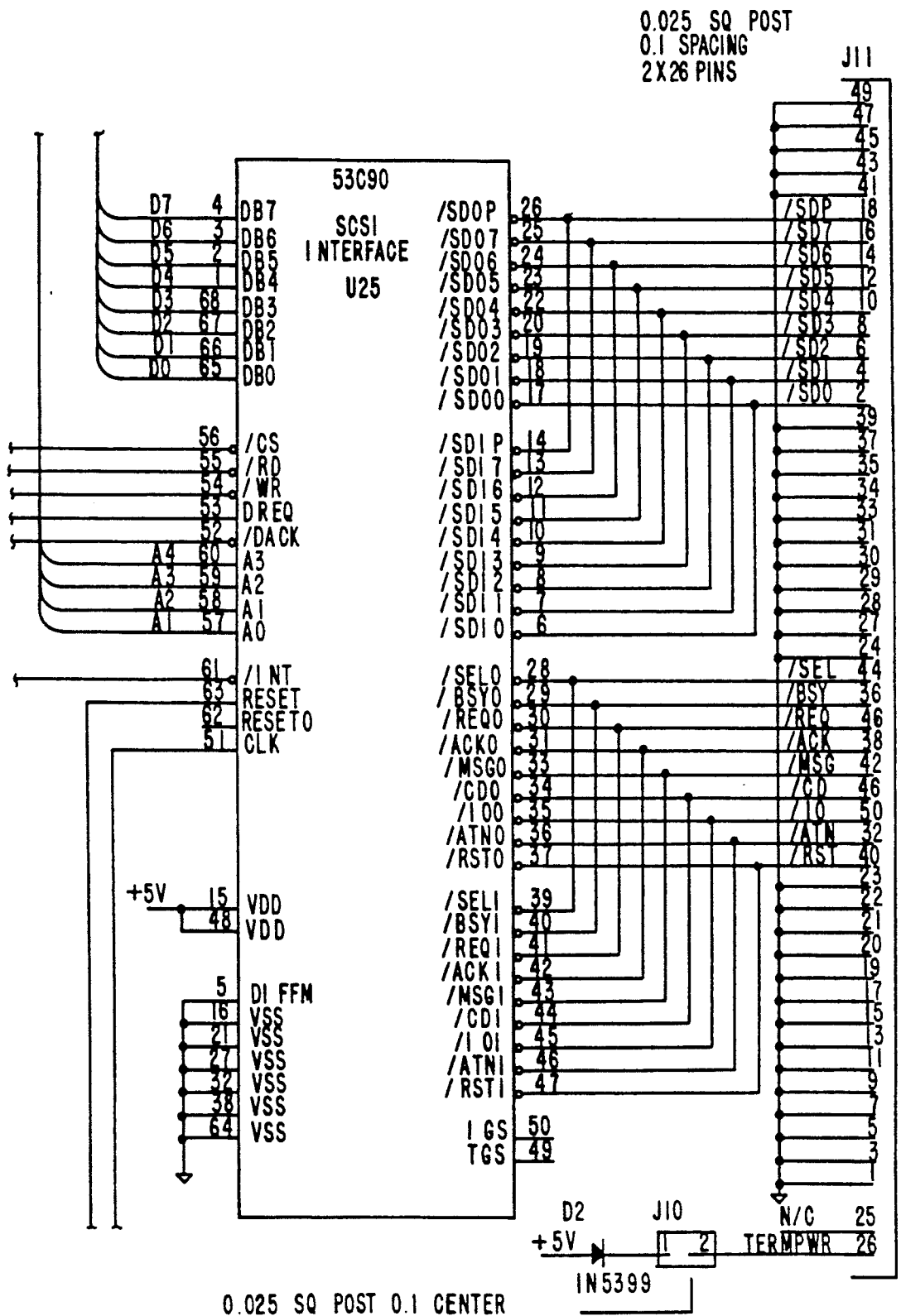
Figures 1, 12C:
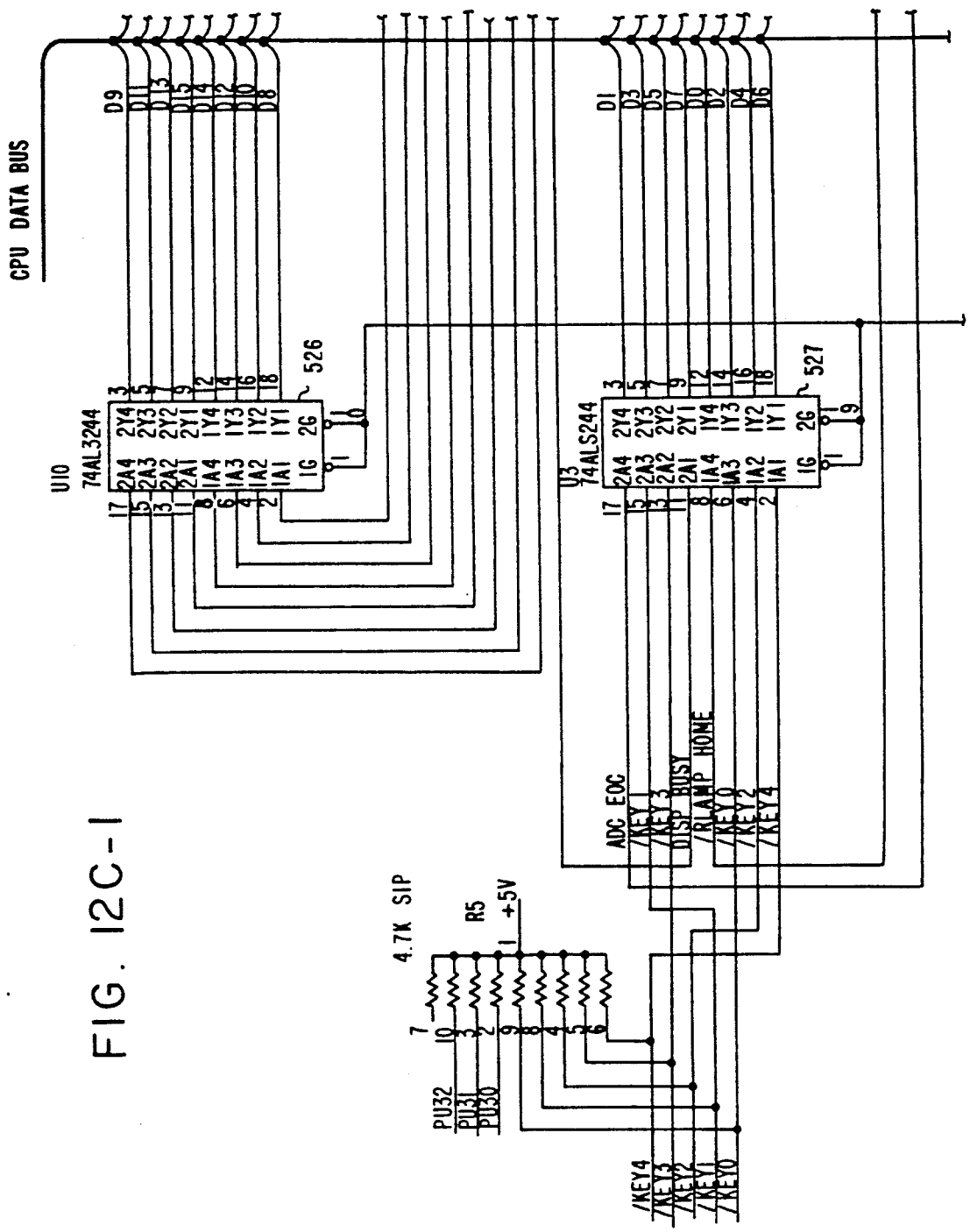
Figures 2, 12C:
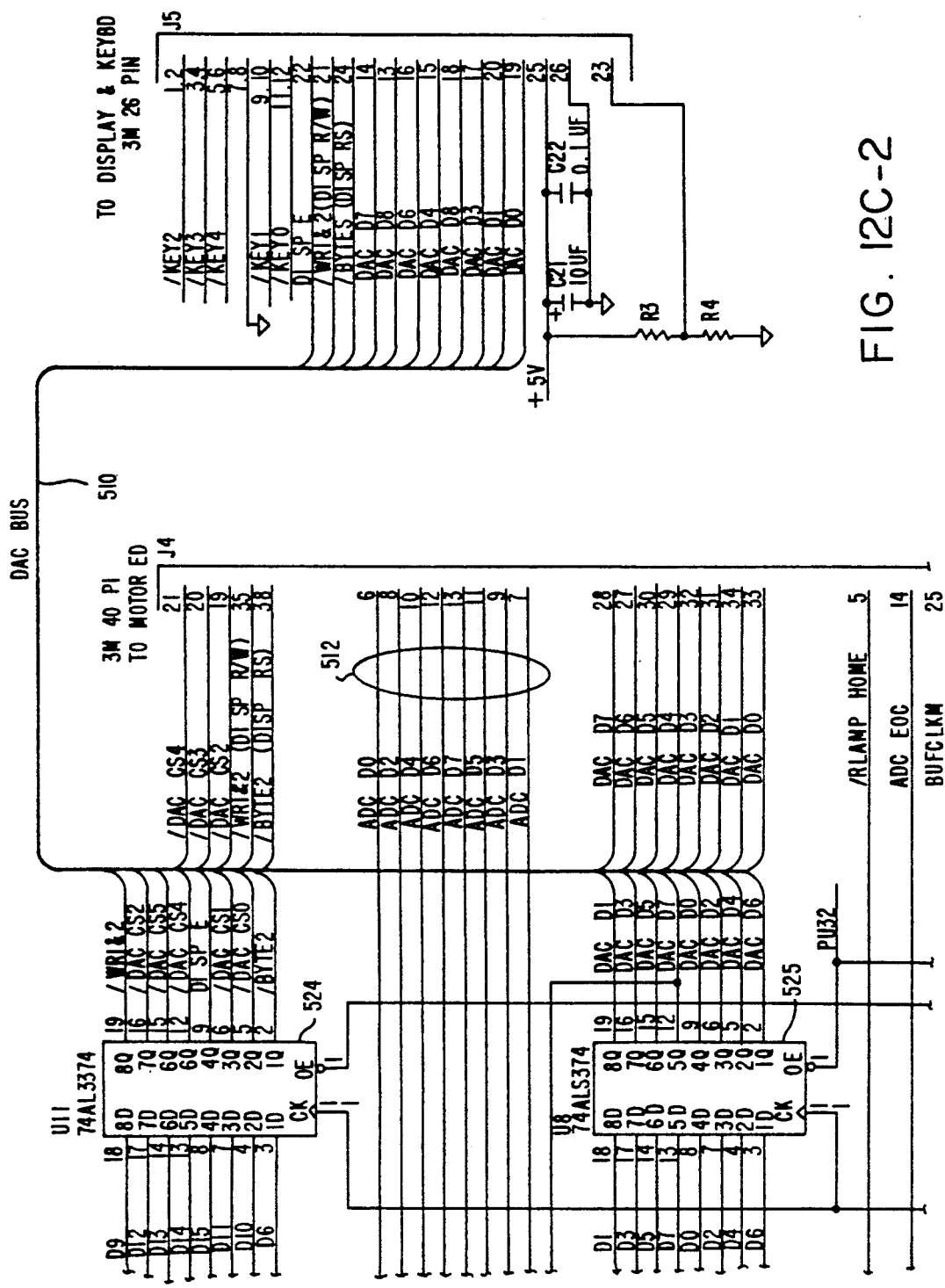
Figures 3, 12C:
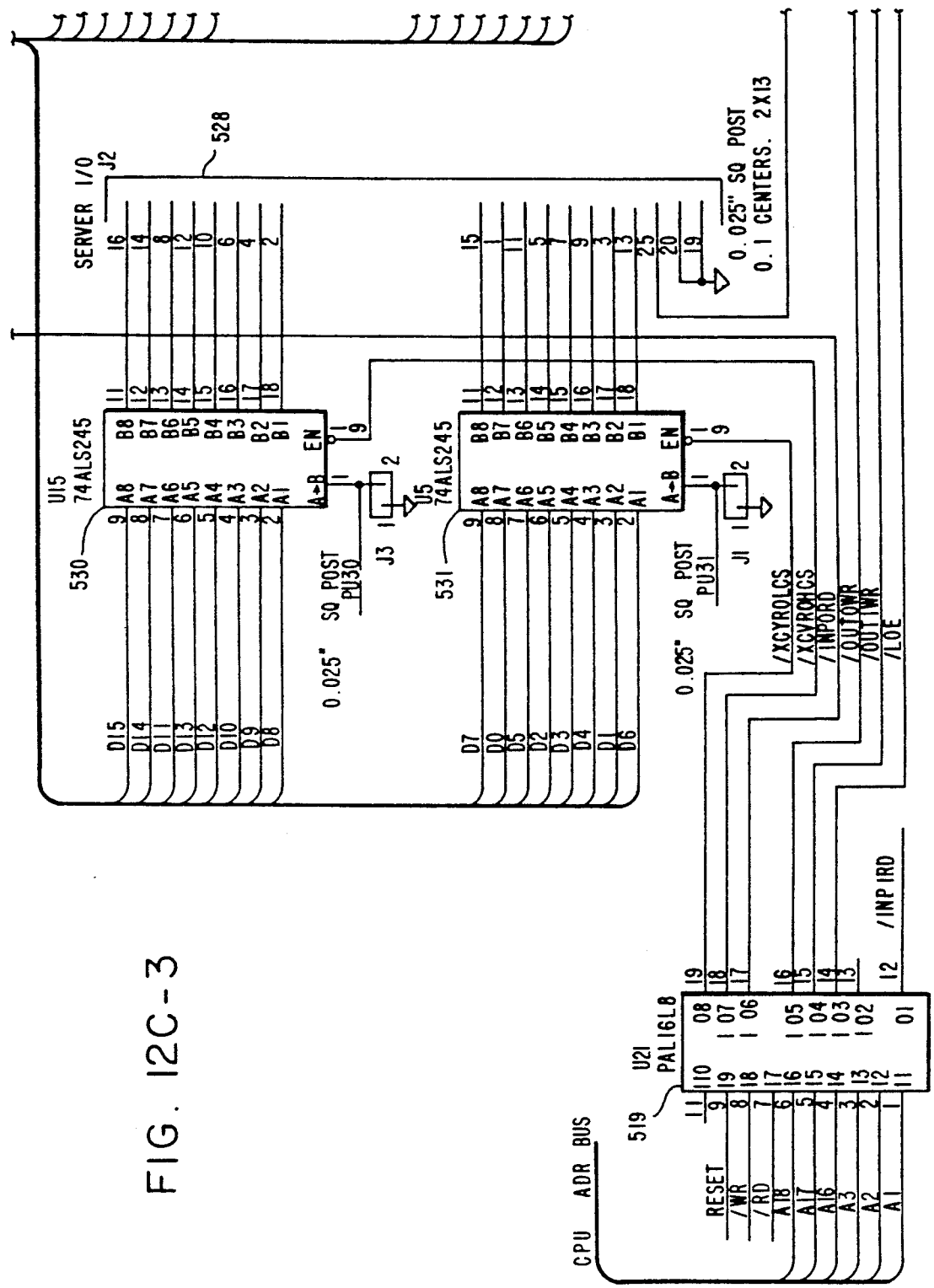
Figures 4, 12C:
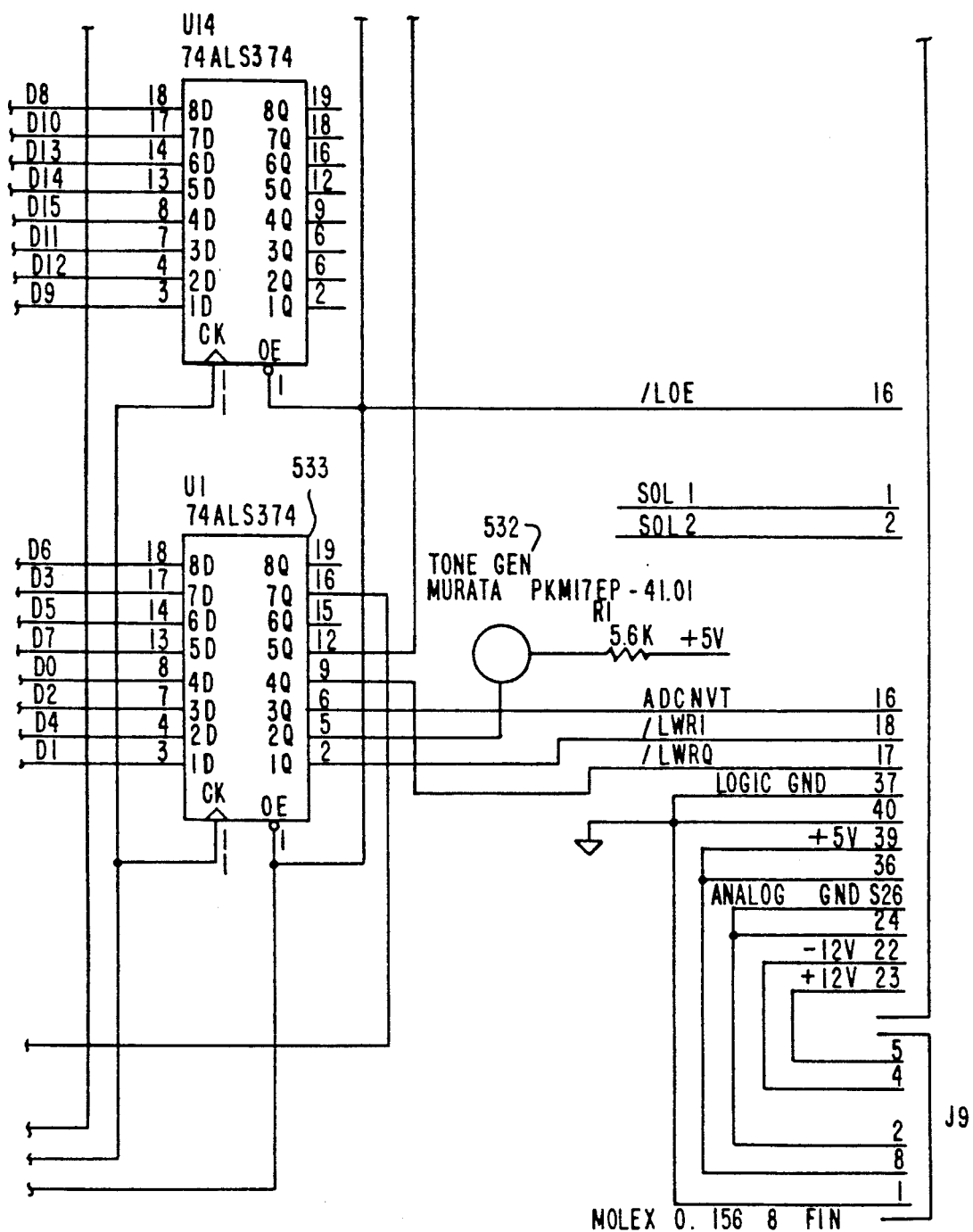
Figures 1, 13A:
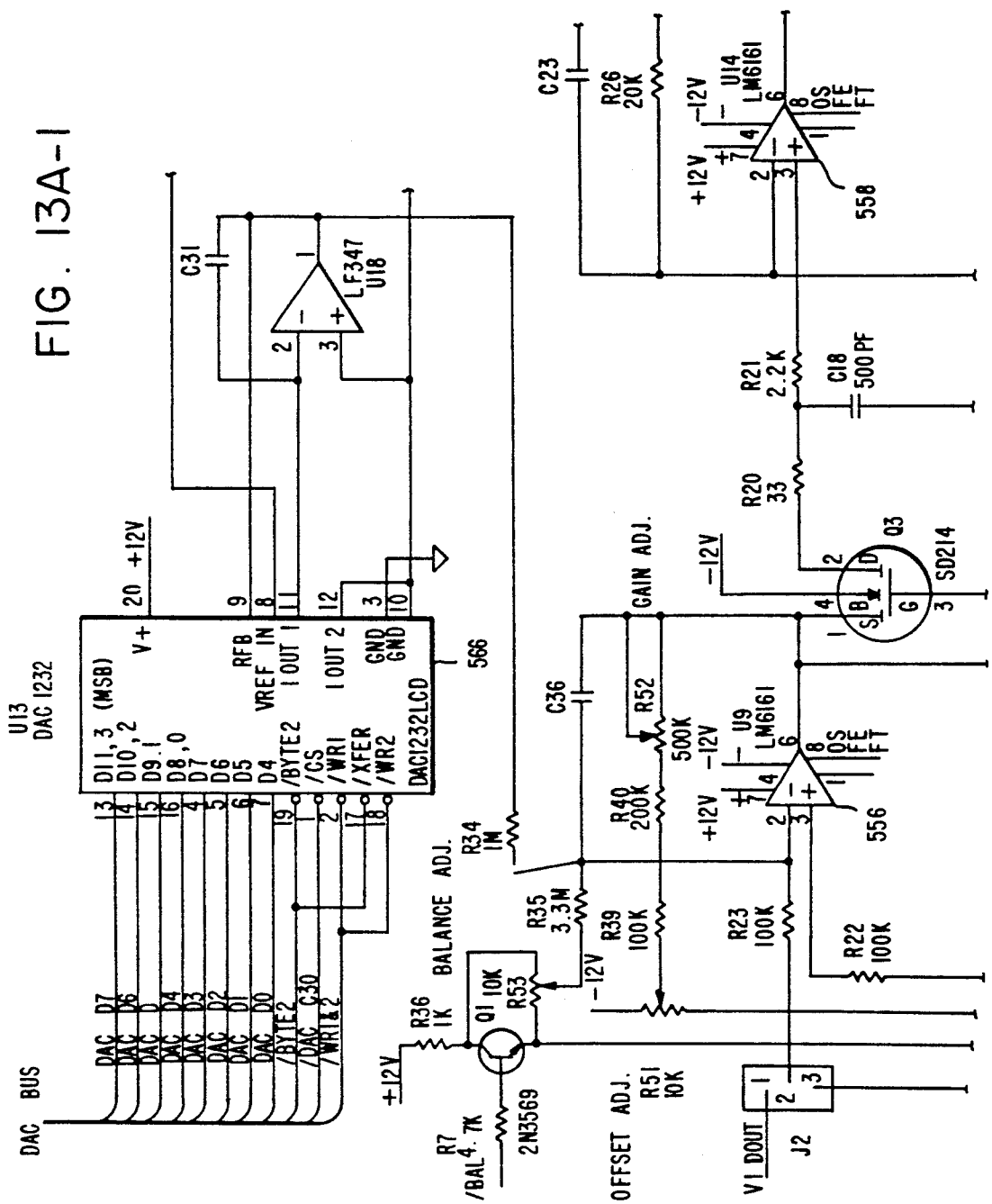
Figures 2, 13A:
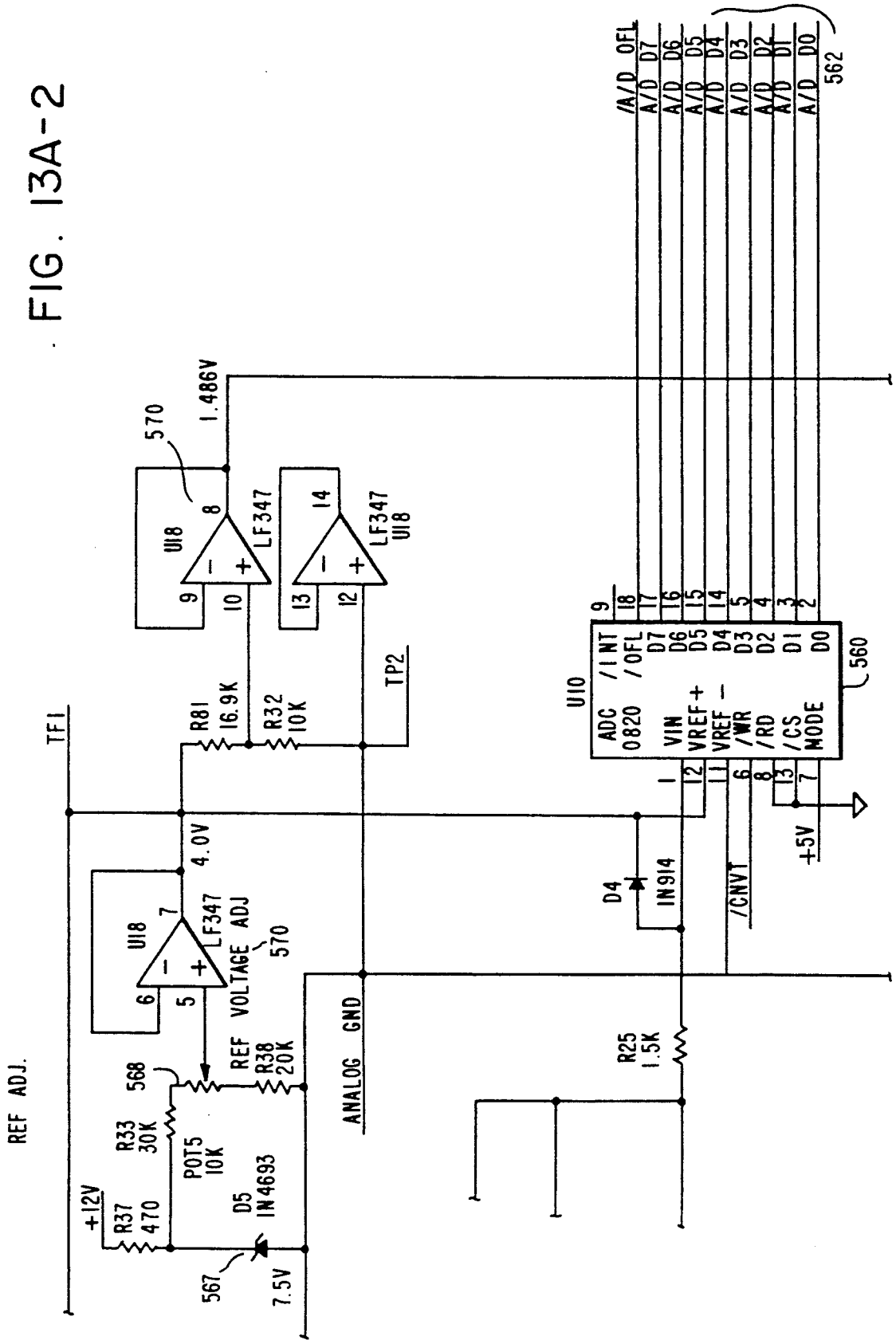
Figures 3, 13A:
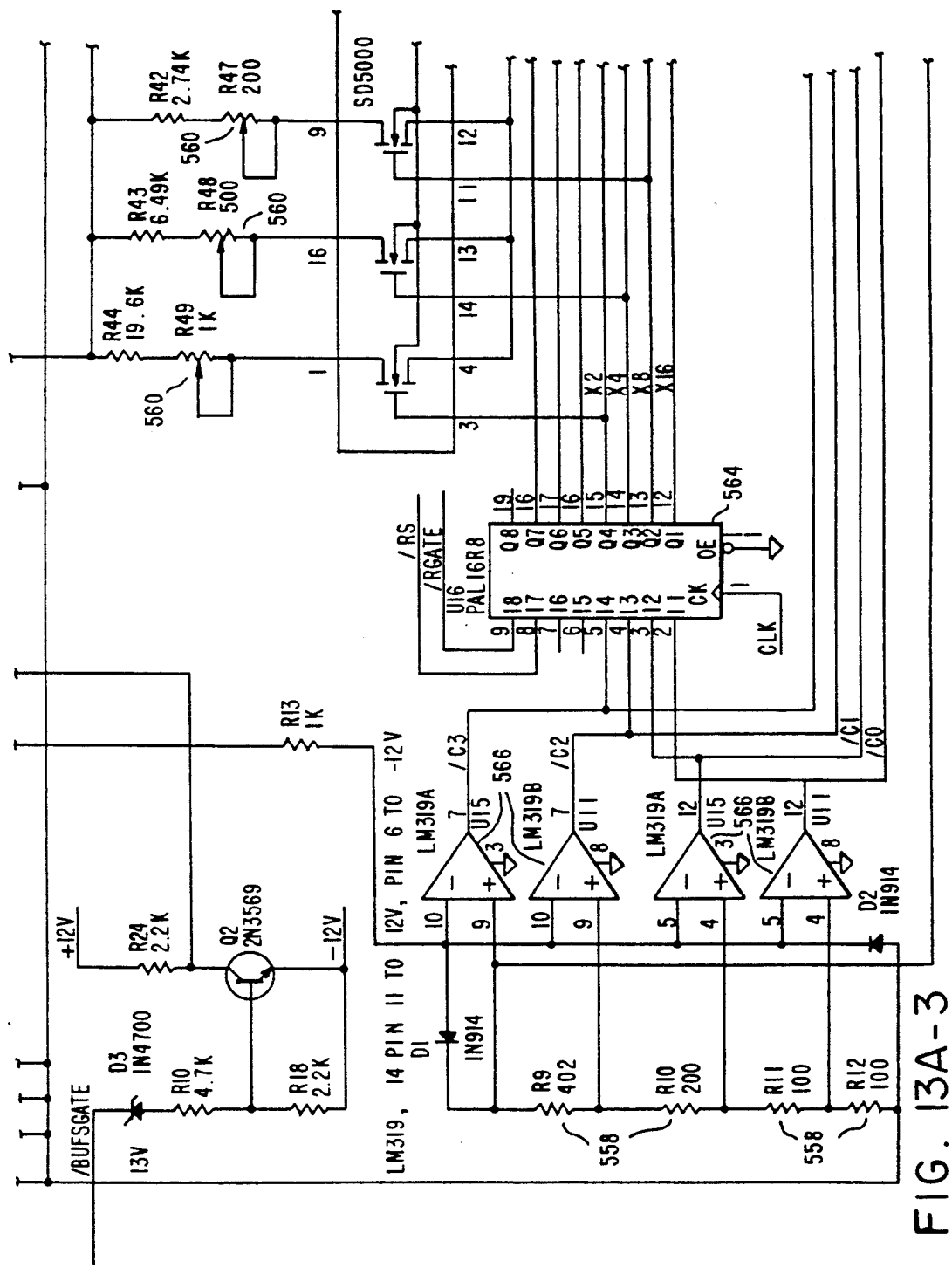
Figures 4, 13A:
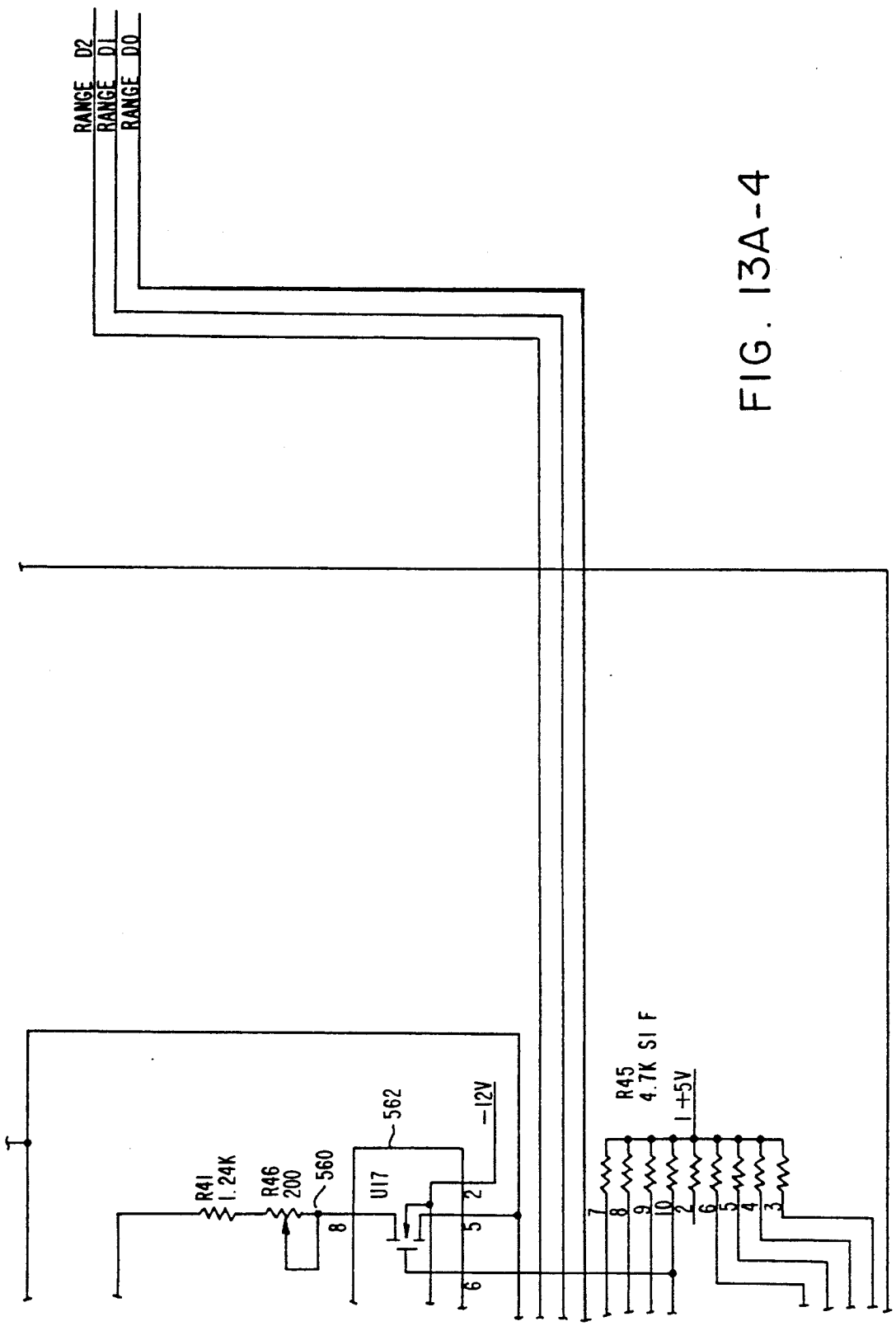
Figures 1, 13B:
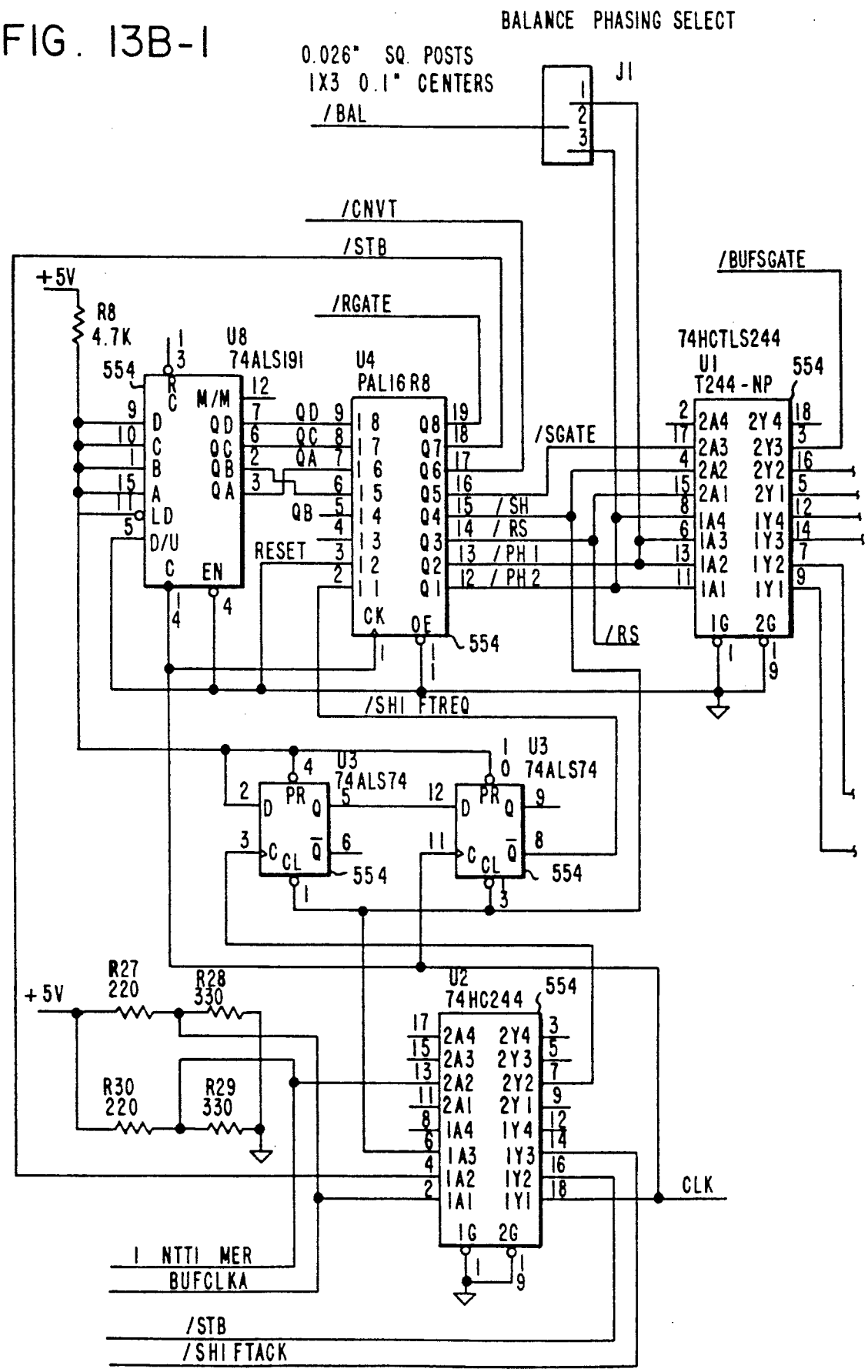
Figures 2, 13B:
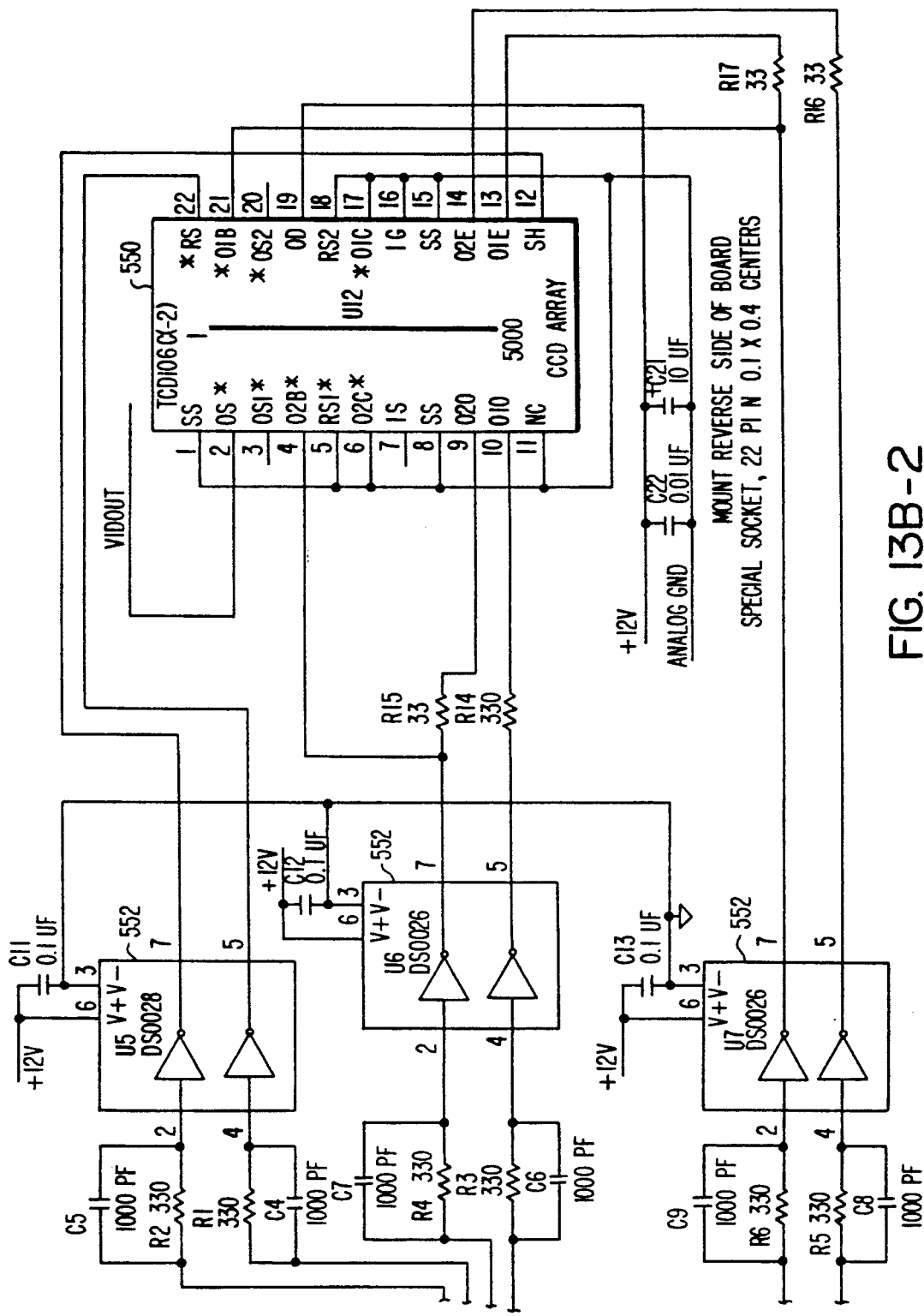
Figure 13C:
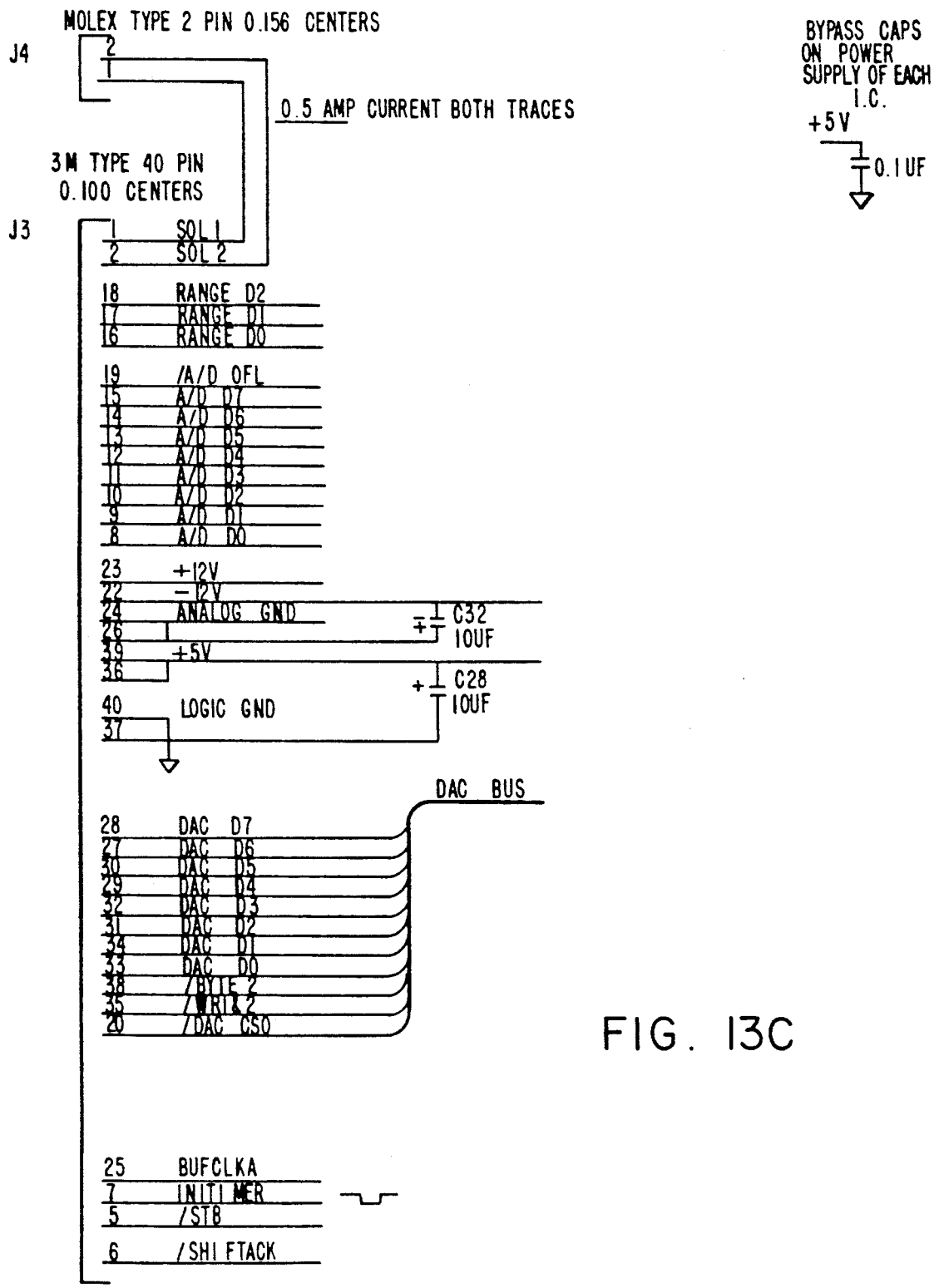
Figures 1, 14A:
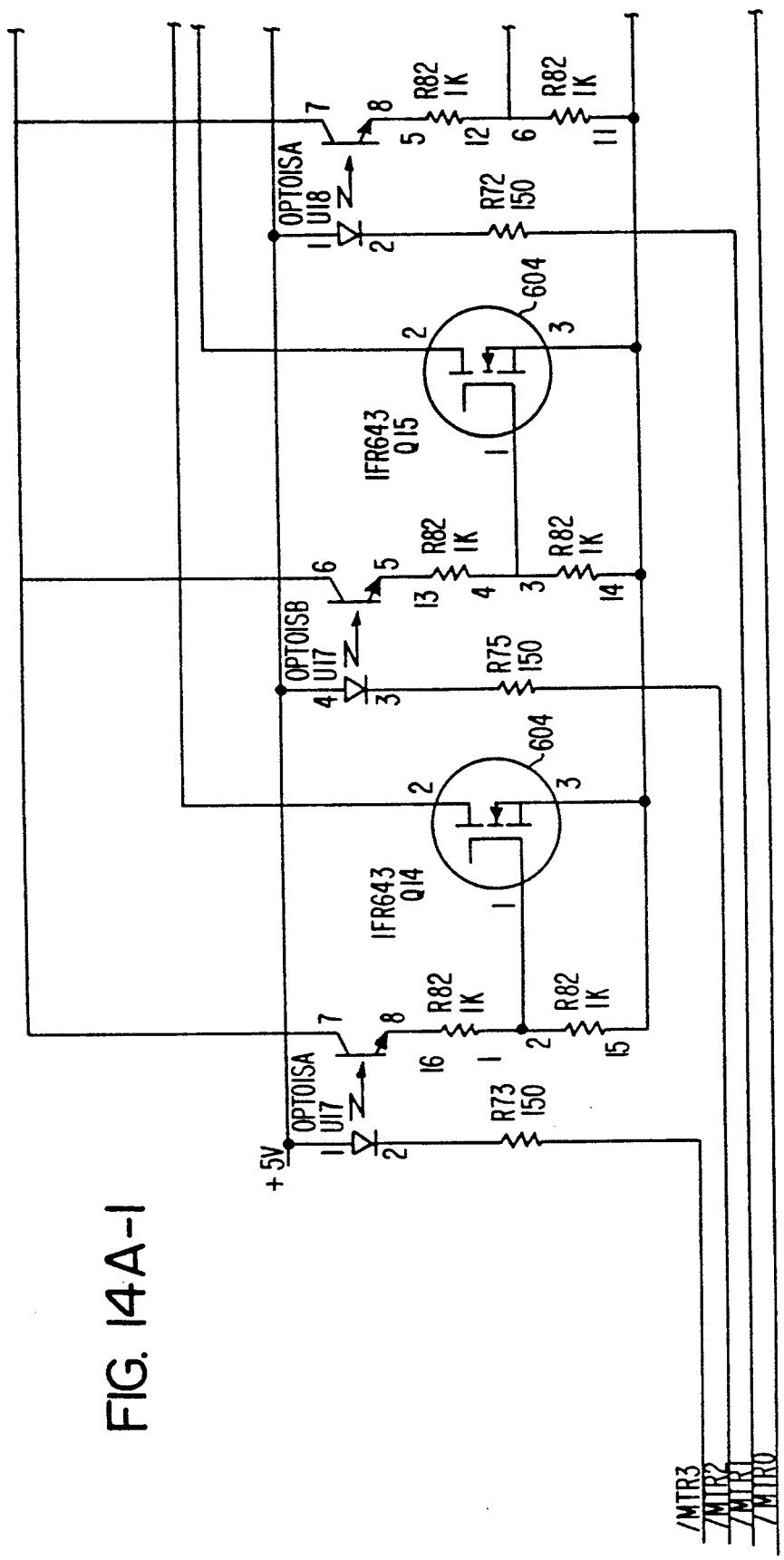
Figures 2, 14A:
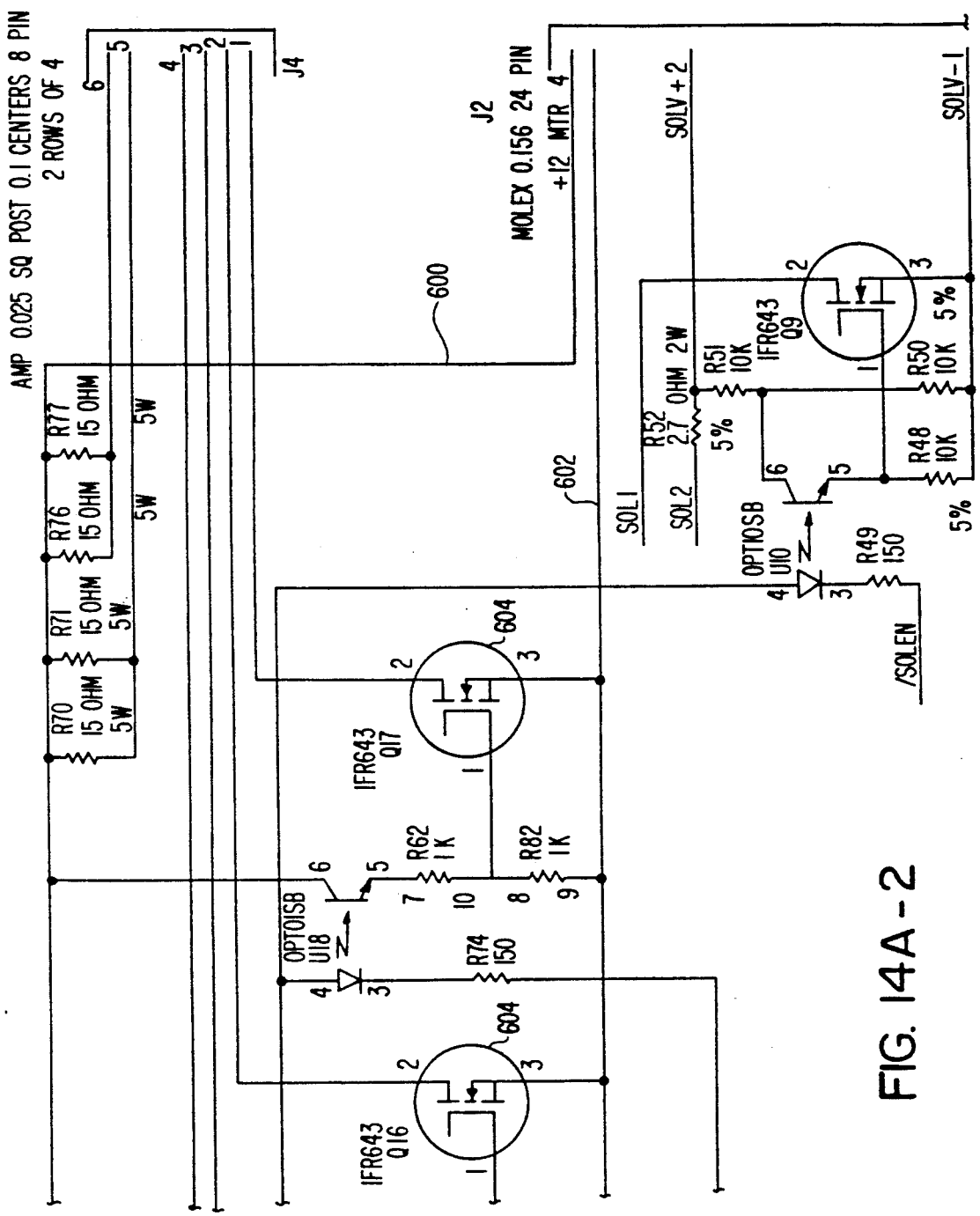
Figures 3, 14A:
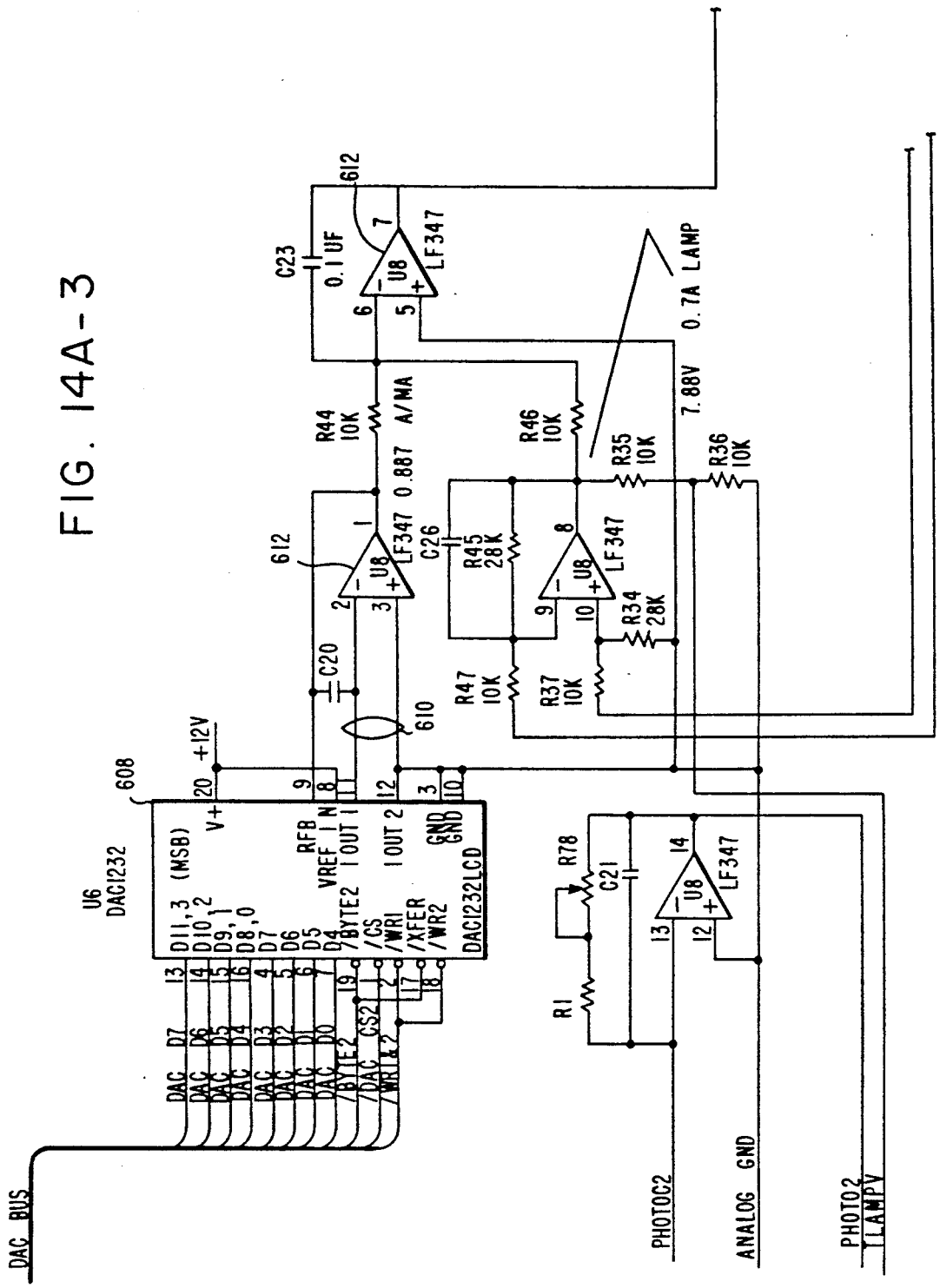
Figures 4, 14A:
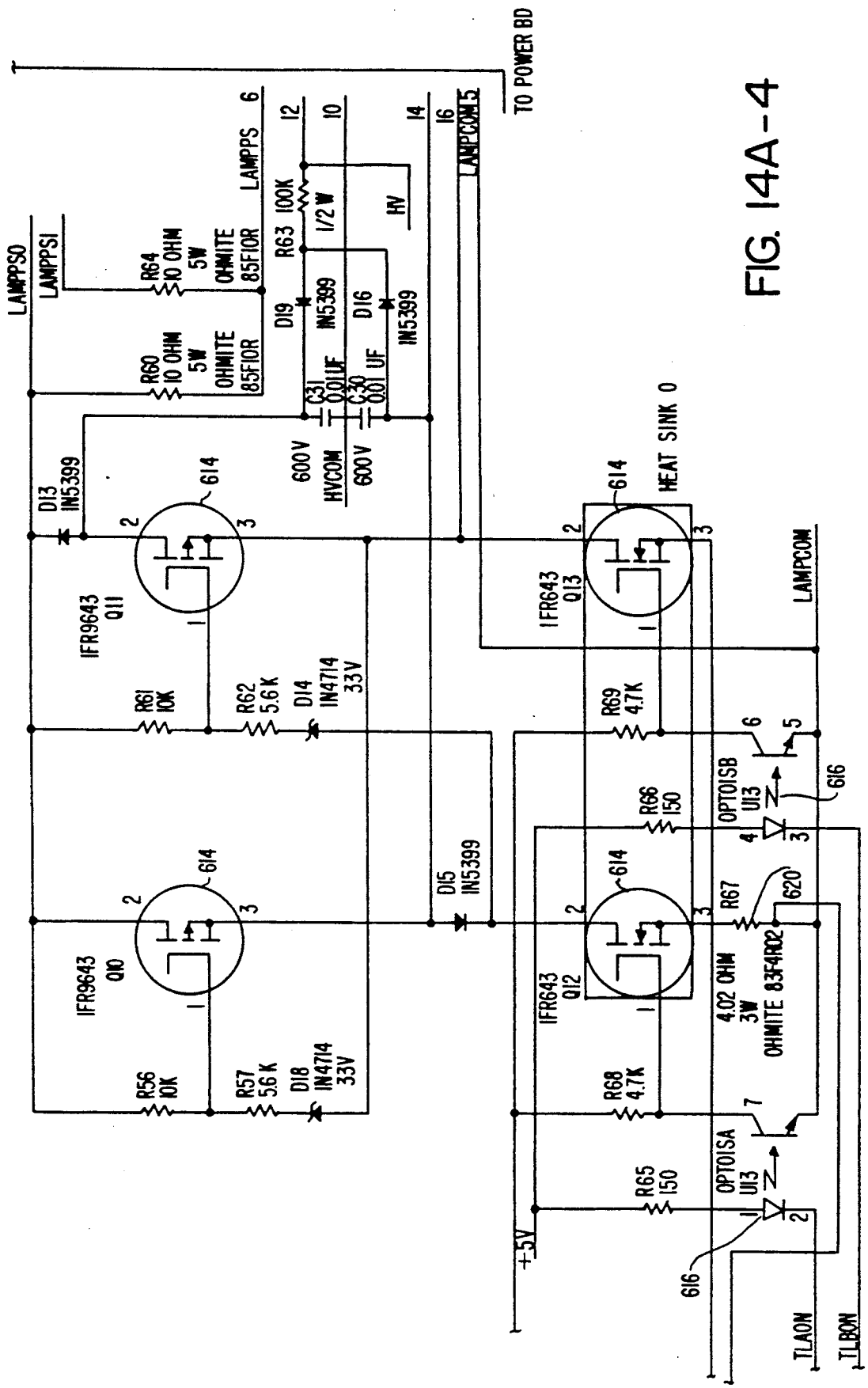
Figures 1, 14B:
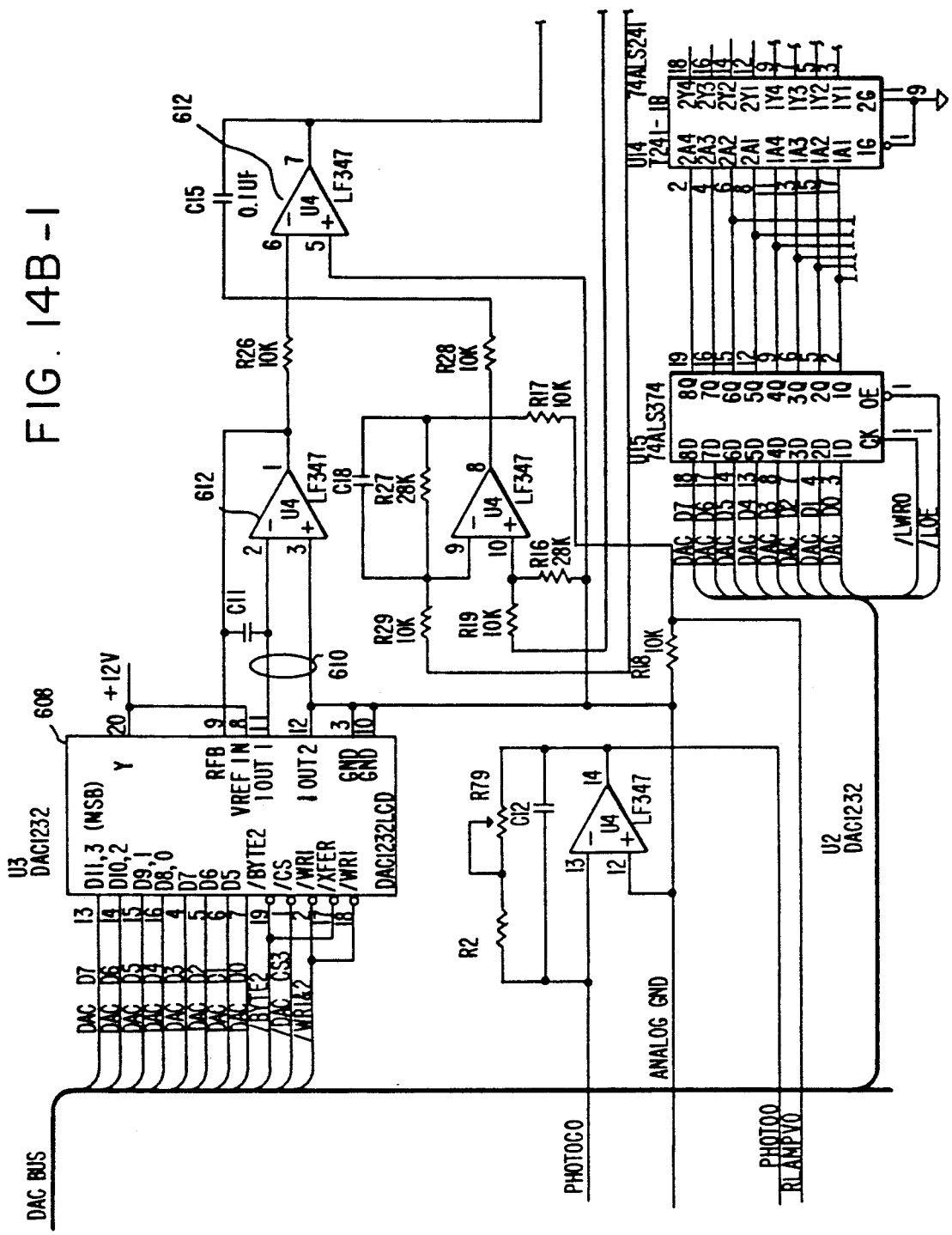
Figures 2, 14B:
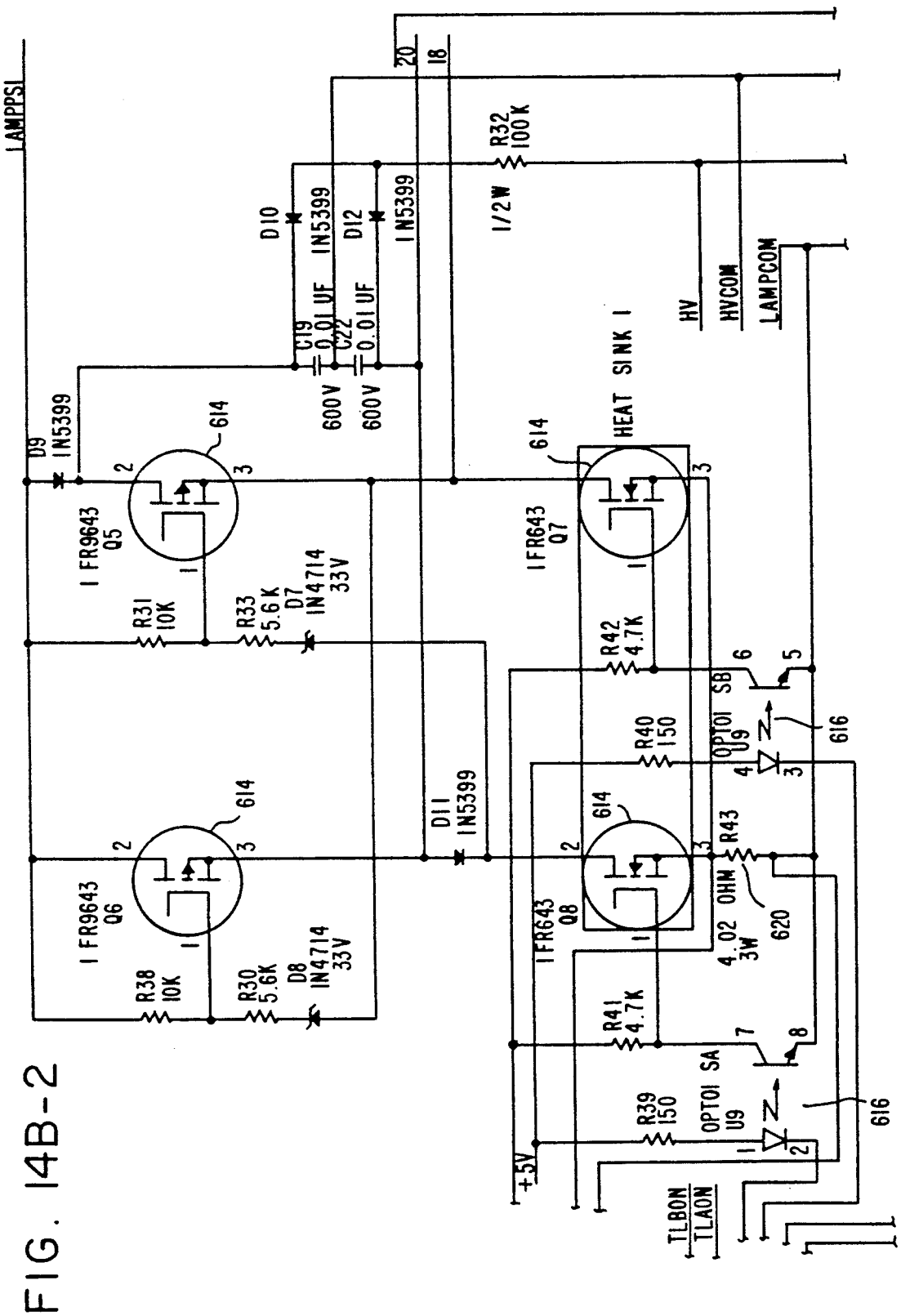
Figures 3, 14B:
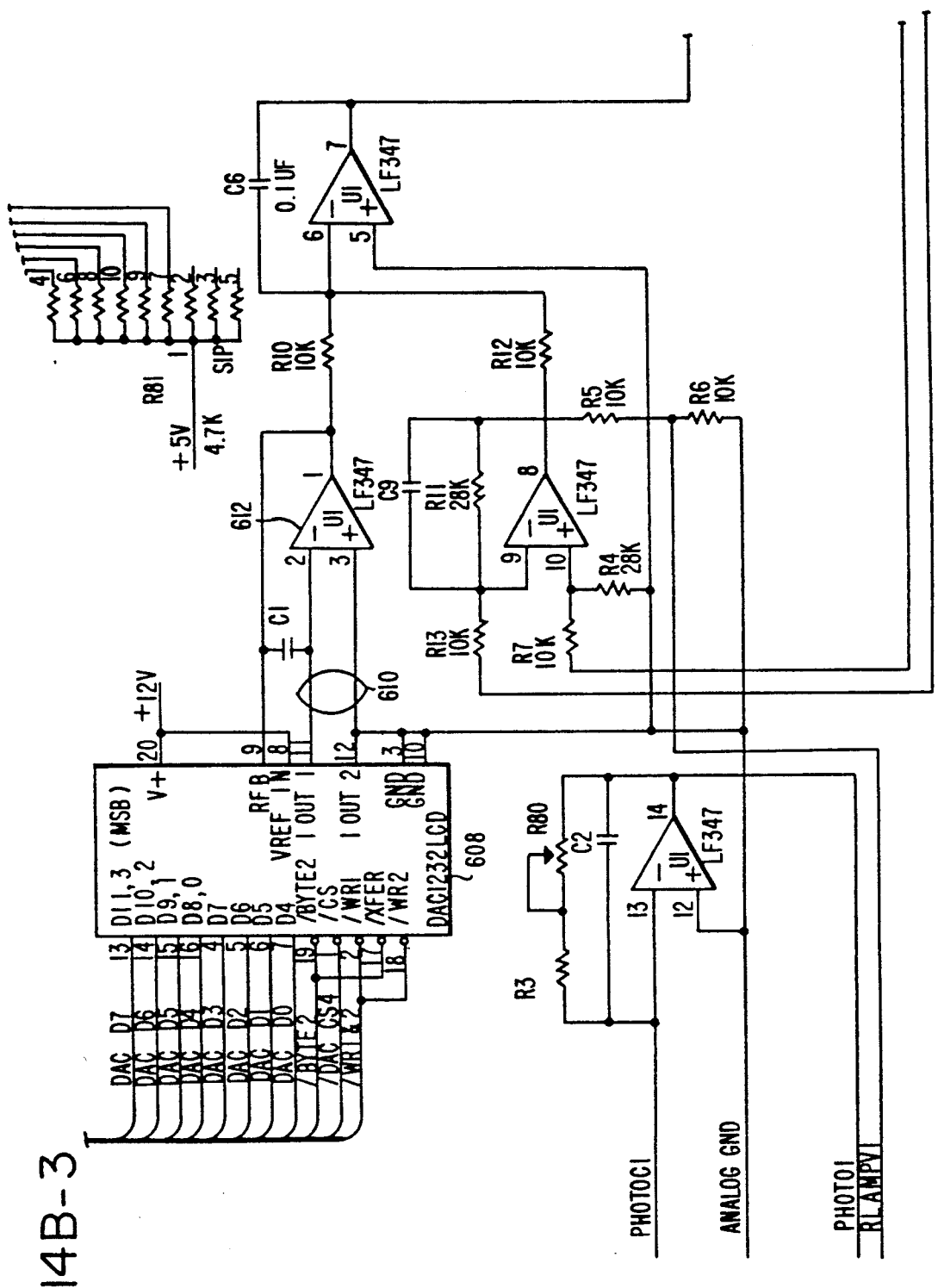
Figures 4, 14B:
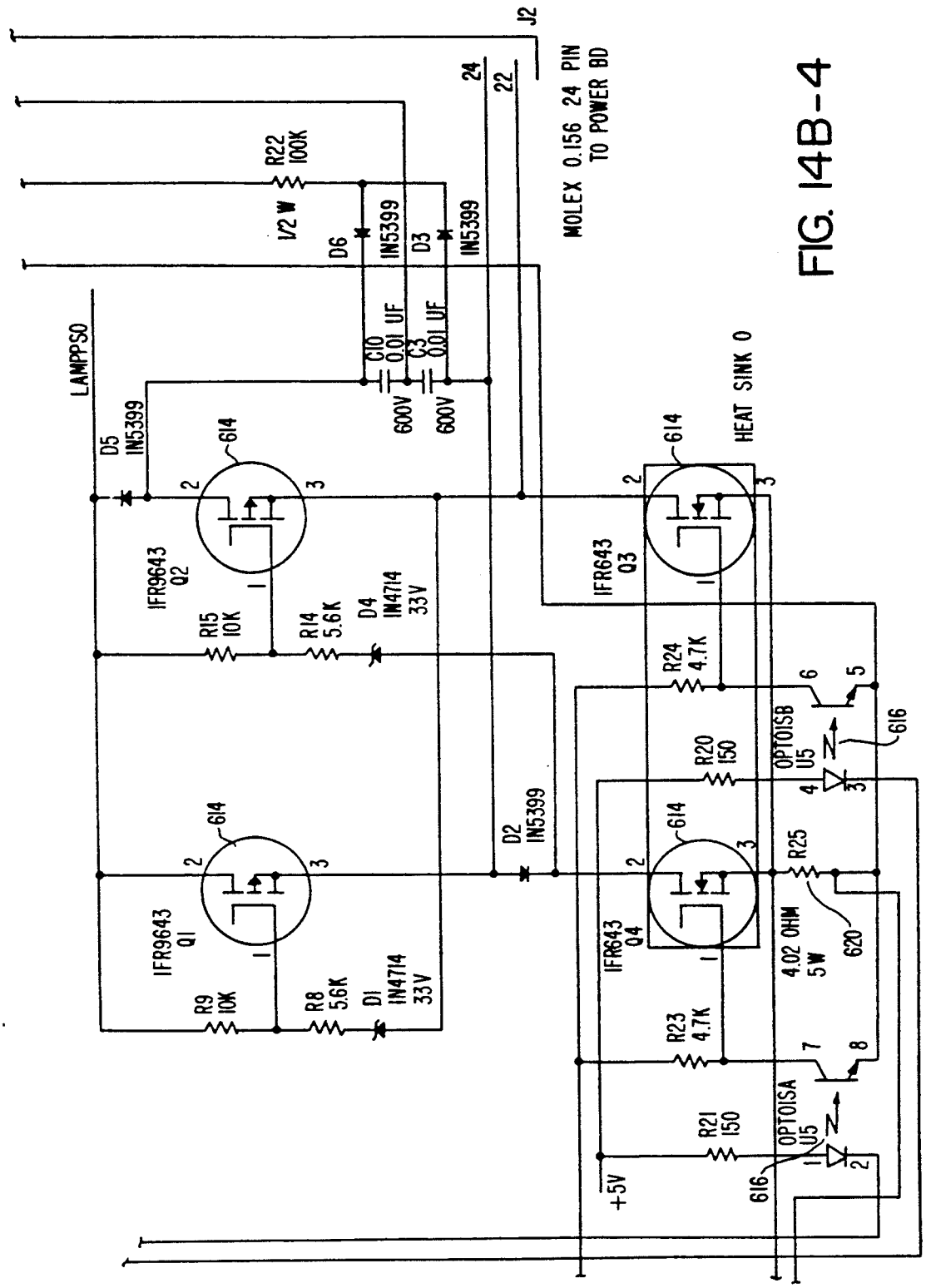
Figures 1, 14C:
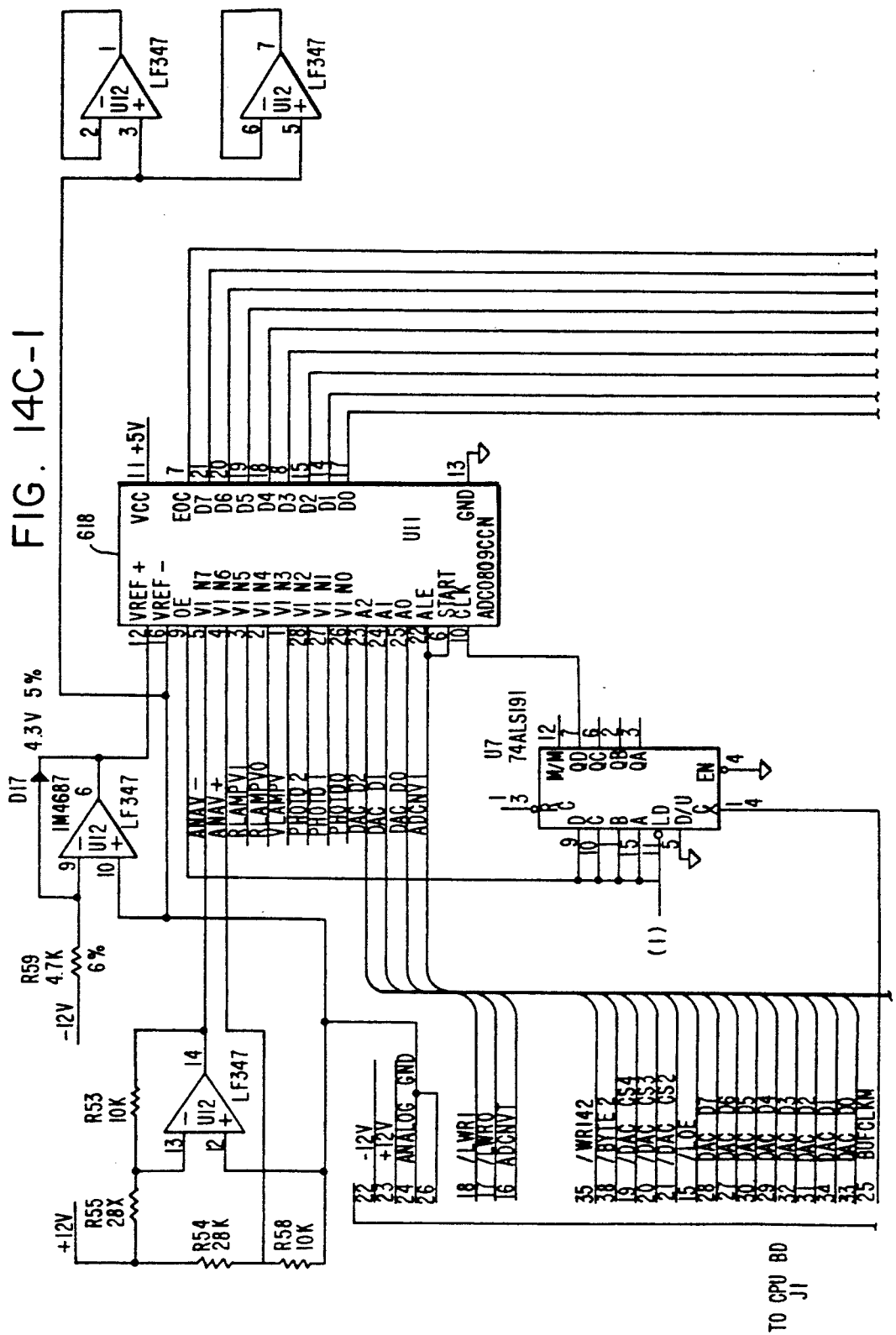
Figures 2, 14C:
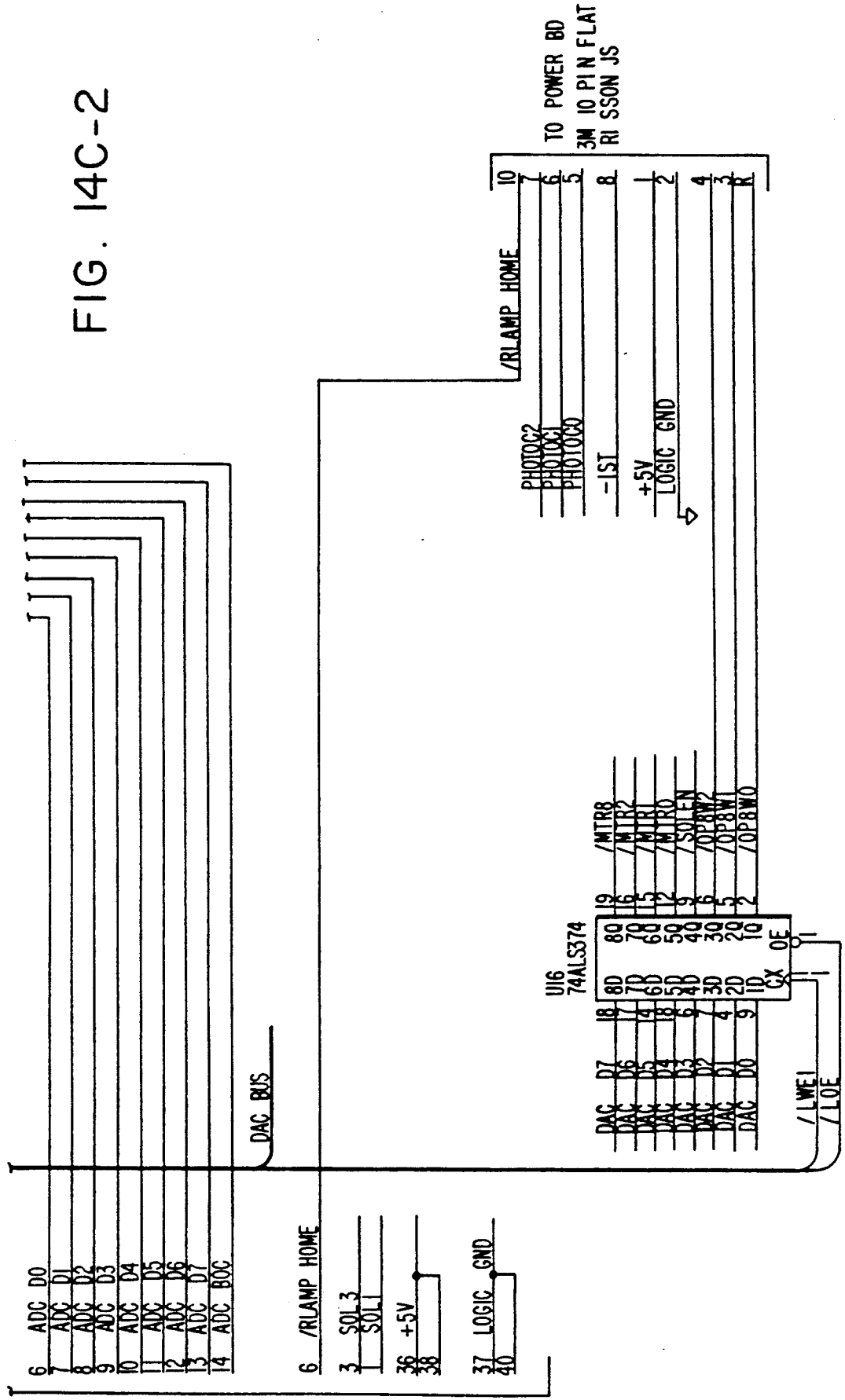
Figure 15A:
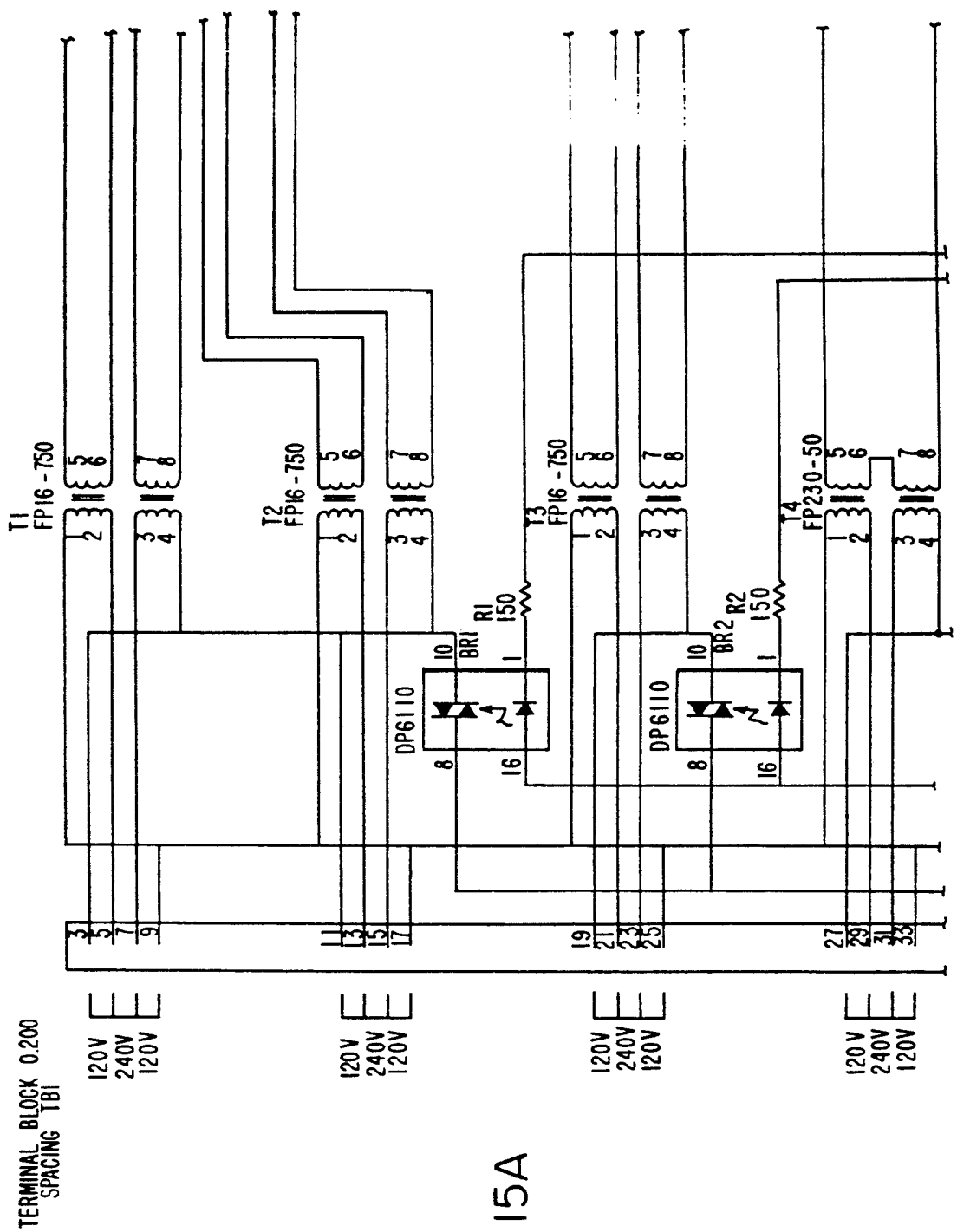
Figure 15B:
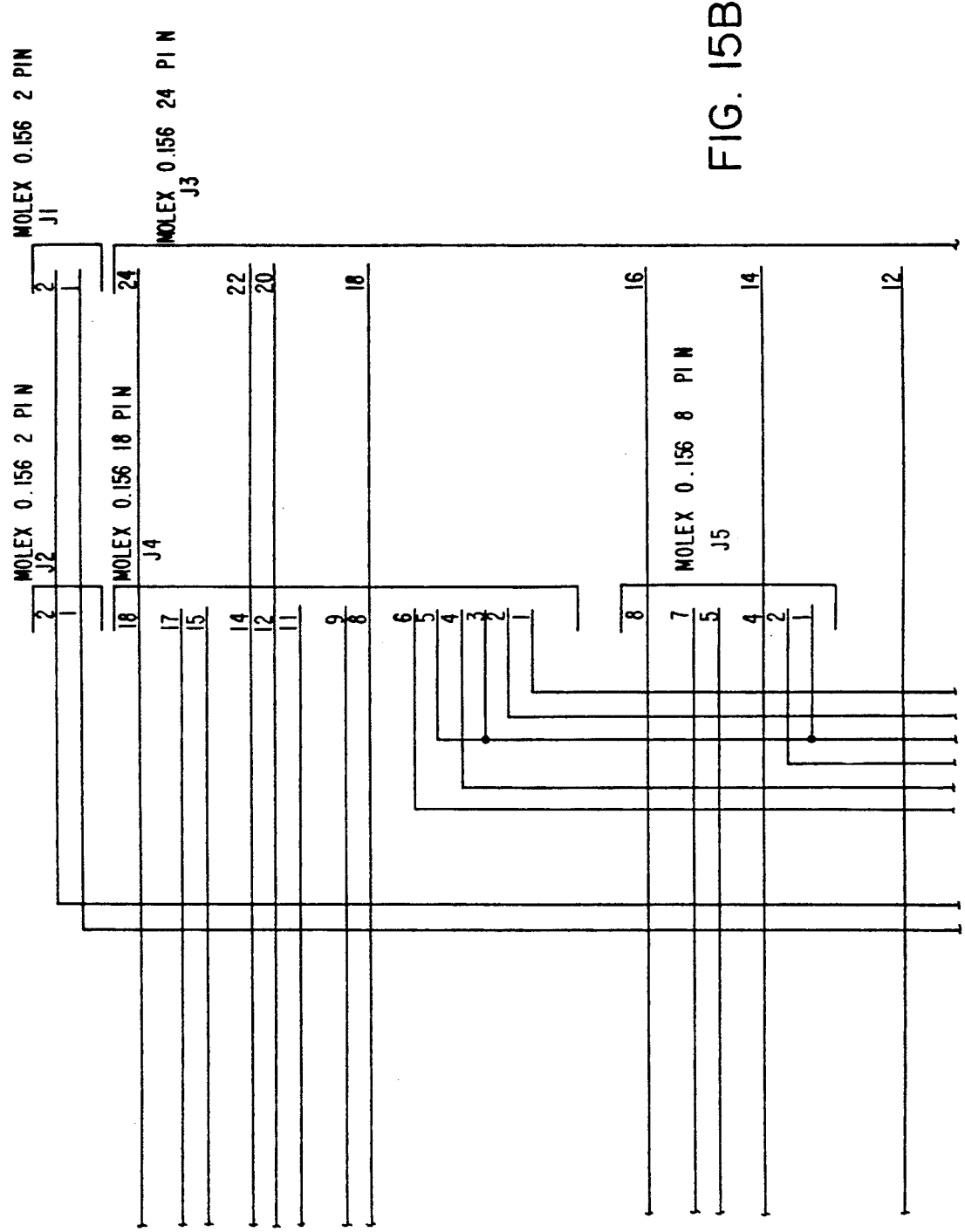
Figure 15C:
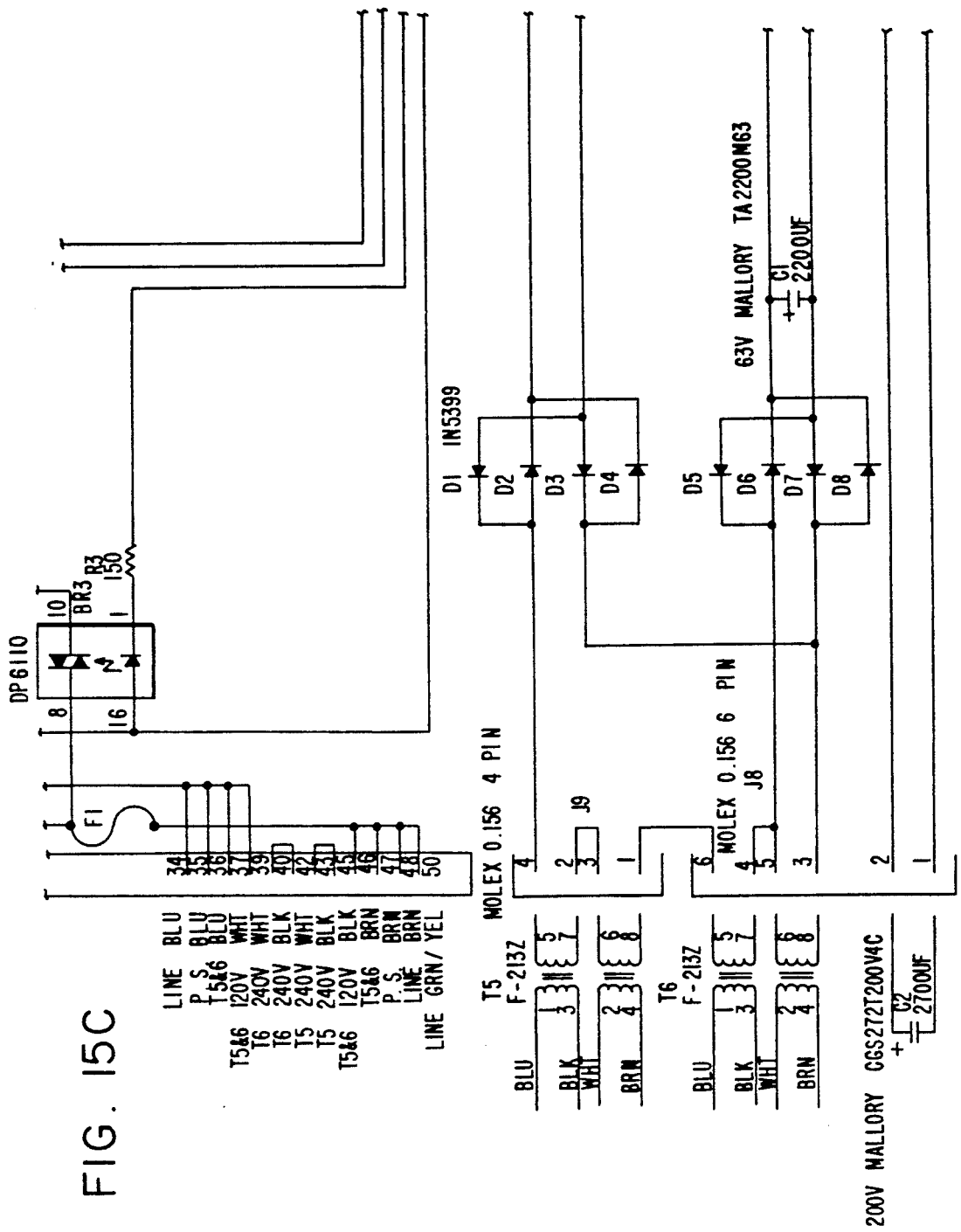
Figure 15D:
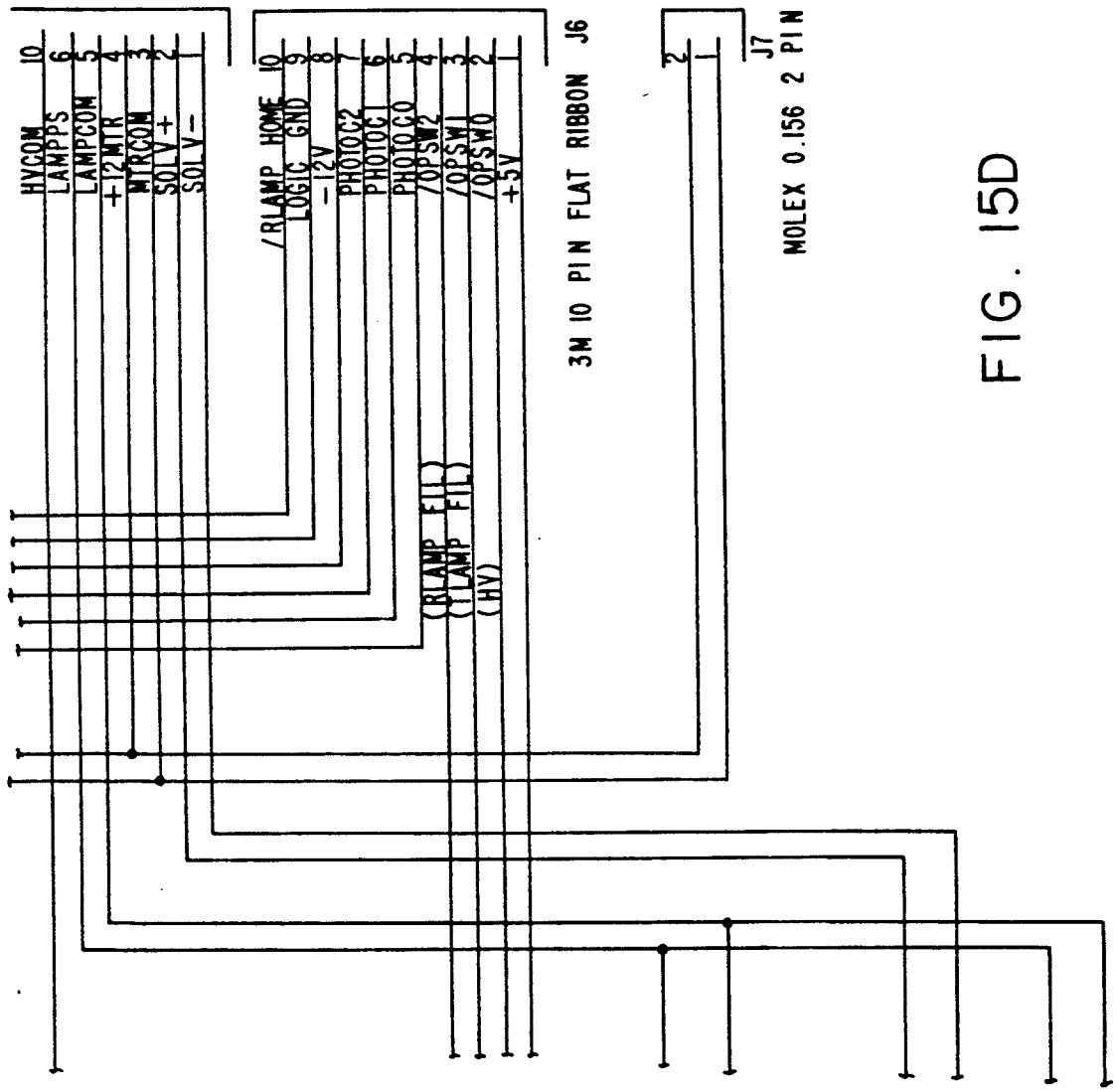

FIGS. 7, 8, and 9 are front, side, and top views, respectively, of a drive mechanism;

FIGS. 10A through 10L are various views of components of a drive mechanism; specifically FIGS. 10A, 10B, and 10C are side, top, and front views of an arm clamp; FIG. 10D is side view of a spring and FIG. 10E is a representation of the bending configuration of the spring; FIGS. 10F and 10G are top and side views, respectively, of a slot panel; FIG. 10H is an isometric view, partially in section, of a drive shaft; FIG. 10I is an isometric view of cam shaft, and FIGS. 10K and 10L respectively are a top and side view of a shutter;

FIG. 11 is a top view of a sample support tray and grid;

FIGS. 12A through 12C are electrical schematics of the scanner CPU board;

FIGS. 13A through 13C are electrical schematics of the scanner CCD board;

FIGS. 14A through 14C are electrical schematics of the scanner motor board;

FIG. 15 is an electrical schematic of the scanner power board; and

Figure 16A:
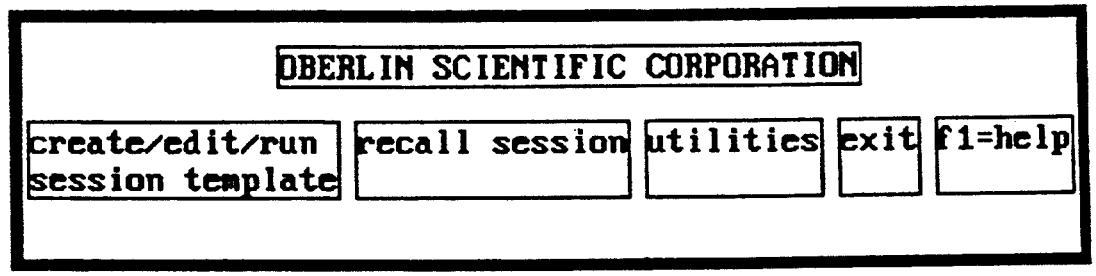

FIGS. 16A through 16AA illustrate the screen displays produced by the program printed in Appendix B.

FIGS. 17A and 17B illustrate the general method of display of information used by the invention.

STRUCTURE

Figure 1:
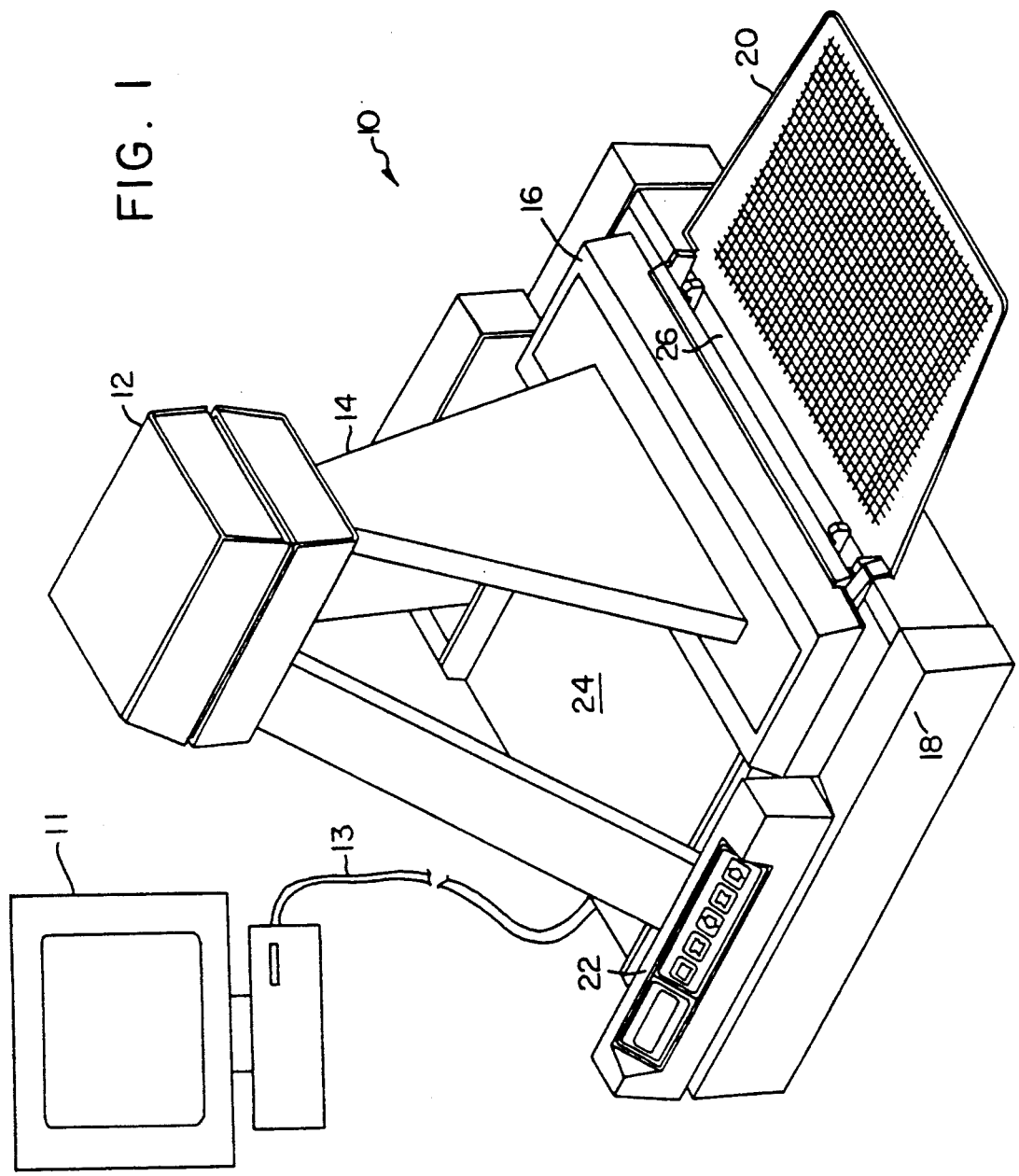
FIG. 1 is a generally isometric view of an imaging system or scanner of the invention, and its associated computer hardware.
Figure 2:
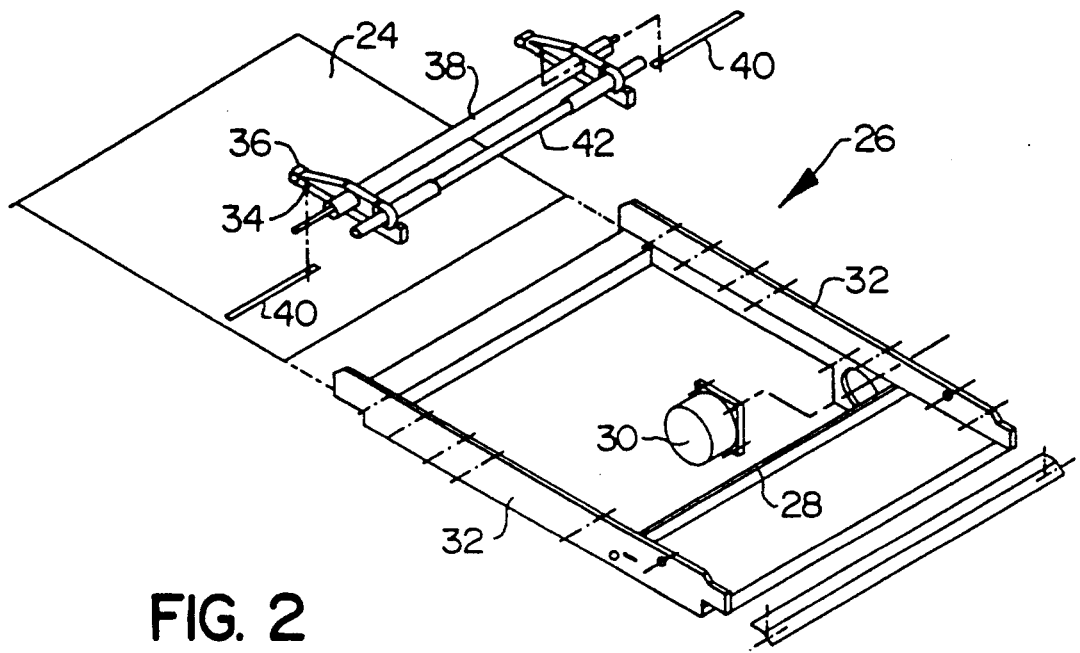
FIG. 2 is an isometric partly exploded view of a drive mechanism.
Figure 3:
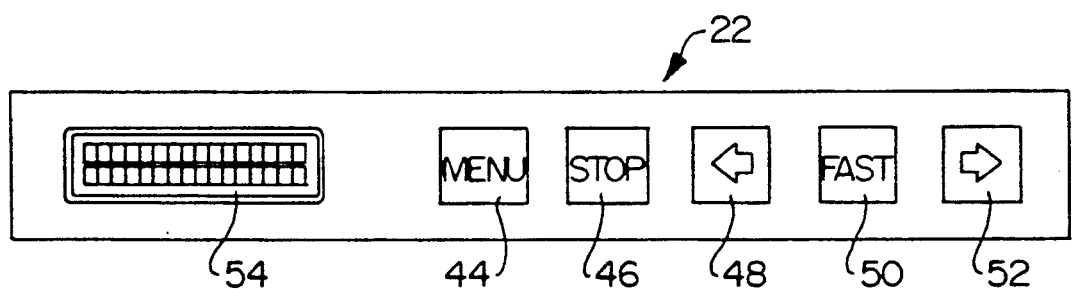
FIG. 3 is a front view of a control panel.

Referring to FIG. 1, imaging system or scanner 10 is electrically linked by a cable 13 to a host computer 11. Host computer 11 may be any standard IBM compatible AT (286 or 386 based) computer having one megabyte of random access memory (RAM), a floppy disc drive (high density), a parallel printer port, a serial port for mouse support, a mouse, a VGA graphics board with 512K of RAM, and a hard disc, preferably of capacity greater than 100 megabytes and an access time of less than 20 milliseconds. Any higher level computer also may be used with scanner 10. The computer also is provided with an SCSI interface PC board. The software used for running the computer is described below.

Scanner 10 includes a camera unit 12, having a linear 5,000 CCD array, and a light shroud 14, which prevents light entering the camera unit except from reflectance light housing 16. Light is provided either from transmission lights 18, or from reflectance lights within reflectance light housing 16. Samples are passed within reflectance light housing 16 on a flat sample support tray and grid 20. The sample is generally gripped and moved backward and forward by drive mechanism 26. Drive mechanism 26 is controlled wither by host computer 11, or by a manual control panel 22 which aids in initial positioning of the sample. As the sample is caused to pass through reflectance light housing 16 it passes from sample support tray and grid 20 to sample bed 24.

Referring to FIGS. 2 and 7 through 10 (A through L) there is shown detail of drive mechanism 26. Drive mechanism 26 includes a stainless steel drive shaft 28 connected by a drive belt 29 to a stepper motor 30. The edges of drive mechanism 26 are bounded by side railings 32. These side railings support other components of drive mechanism 26. The drive mechanism is designed to accommodate all widths (up to a maximum width of 14.0 inches) of sample, with thickness up to ¼ inch, e.g., an autoradiogram or a carrier tray. Clearance of up to ¼ inch is provided such that any item on a carrier tray also may be scanned. This includes items such as Petri dishes and microtitre well trays.

Drive mechanism 26 includes a pair of pivotally mounted sample clamps 34 each having at one end a neoprene roller bearing or idler wheel 36, and spaced therefrom an eccentric clamp shaft 38 and a clamp guide shaft 42. A pair of shutters 40 also are connected with sample clamps 34, via a pin 41. Sample clamp 34 is provided with an aperture 35 suitable for holding clamp guide shaft 42 and an aperture 37 suitable for holding cam clamp shaft 38. Rectangular aperture 39 is sized to hold pin 41 of shutter 40. A further aperture 43 is provided to roller 36 which cooperates with drive shaft 28 to cause a sample placed therebetween to move as directed by drive shaft 28.

A spring 94 is provided about sample clamp 34 to cooperate with sample clamp 34 to cause roller 36 to cause a sample to contact drive shaft 28 when cam shaft 38 is rotated by turning a handle (not shown) connected with cam shaft 38. Spring 94 is connected in a manner which allows firm contact between roller 36, a sample, and drive shaft 28 when cam shaft 38 is in one angular position, and causes no pressure to be exerted between cam shaft 38 and clamp guide shaft 32 when cam shaft 38 is in the opposite position. In this manner, sample clamps 34 may be moved freely along cam clamp shaft 38 and clamp guide shaft 42, and then clamped against drive shaft 28 at any desired position. This movement of the sample clamps causes concurrent movement of shutters 40. Shutters 40 cooperate with a slot 47, provided in a slot panel 90, through which light may pass to a sample clamped in position by the above described drive mechanism. If a sample is relatively thin, sample clamps are moved inward with concurrent inward movement of shutters 40 and light is prevented from passing through slot 47 except through the sample region. In this way saturation of the CCD array of the camera is prevented.

Motor 30 is electronically connected with a control panel 22 such that movement of the motor may be stopped by pressing button 46 or moved forwards (button 48) or backwards (button 52) or at a faster speed (button 50). A menu for lighting of the lamps may be accessed (menu button 44). The menu is displayed on LCD array 54. The drive mechanism is controlled by a microprocessor in controlled stepping motor functions of 400 steps per inch.

Referring to FIG. 11, sample bed 24 is provided with a one centimeter square grid to allow accurate placement of a sample centrally within the width of the imaging system. and against an index mark in a manner which informs the host computer of the position of the sample. In this way the host computer may control entry of the sample into the system and identify specific locations within that sample.

Figure 4:
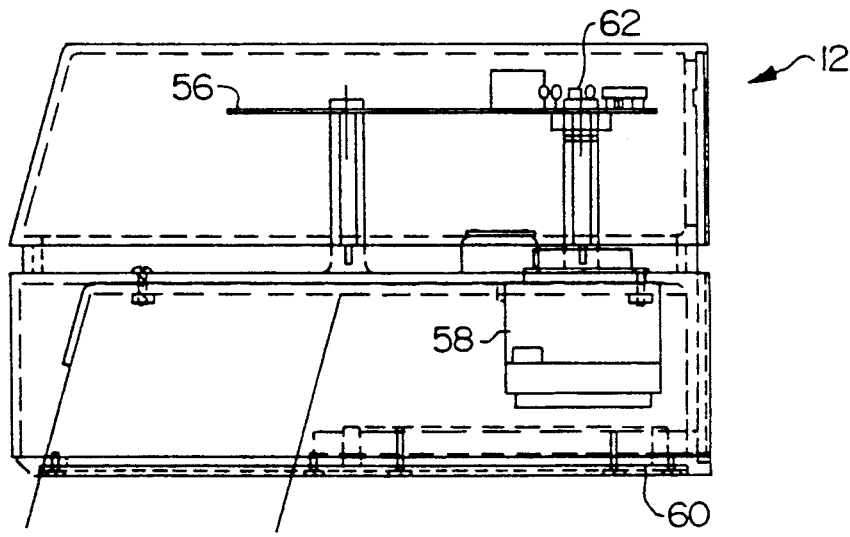
FIG. 4 is an isometric and partially sectional view of a camera unit.

Referring to FIG. 4, camera unit 12 is provided with an array PC board including a 5000 element linear array 62 and associated electronics (discussed below). Also provided is a lens 58 adapted to focus a 12.5 inch line of light from the sample slot to the array. This provides a spacial resolution of 400 dots per inch, although lower resolution may be utilized by computer processing of the image file. Also provided is a filter tray 60.

Figure 5:
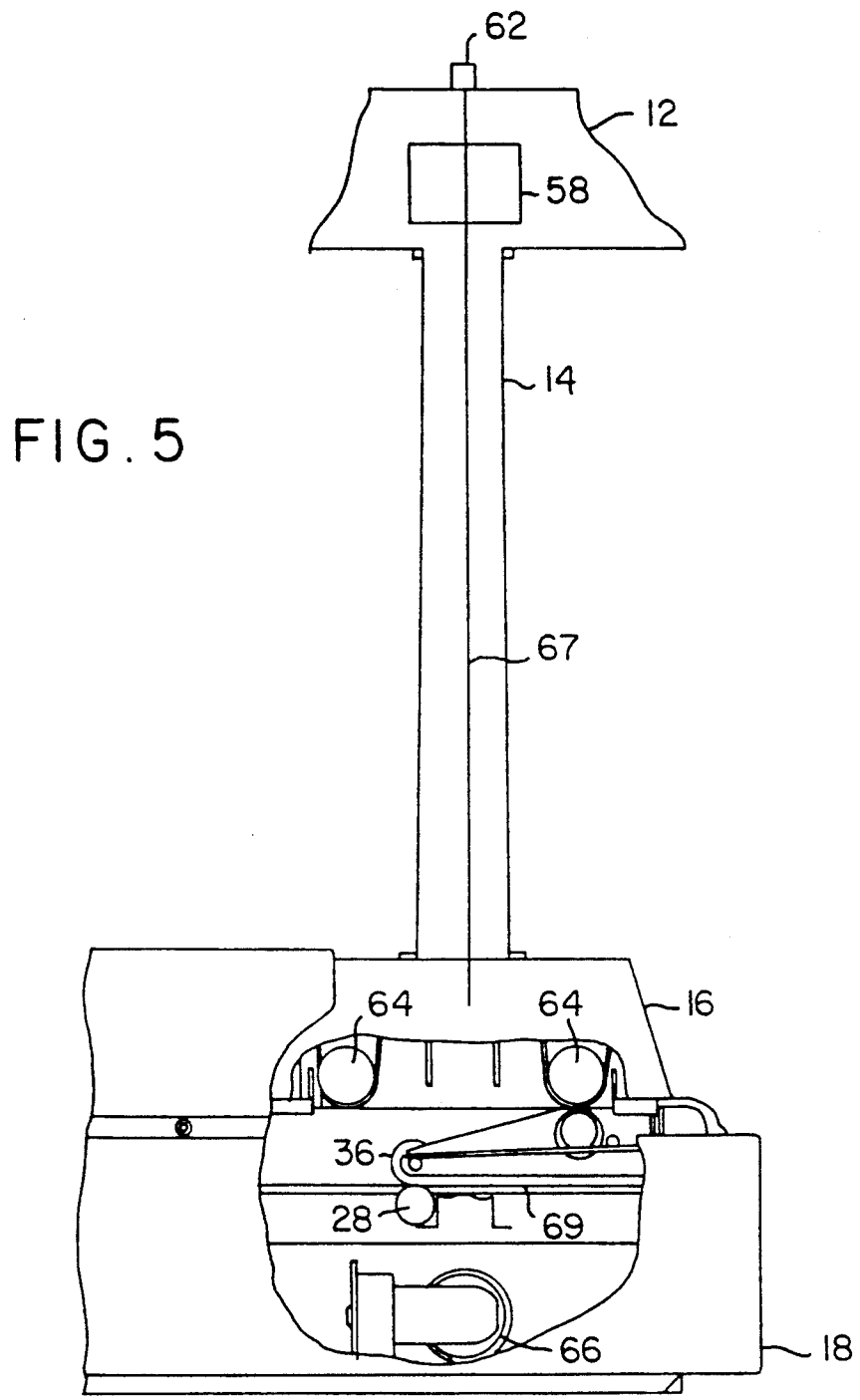
FIG. 5 is an isometric and partially sectional view of transmission and reflectance light sources and a light path to a camera.

Referring to FIG. 5, the location of camera unit 12 including array 62 and lens 58 is shown relative to light sources in the reflectance light housing 16. Light shroud 14 prevents stray light from reaching CCD array 62. Light from transmission lamp 66 or from reflectance lamps 64 is directed onto sample 69 and travels directly from the sample along light path 67 to CCD 62.

Figure 6:
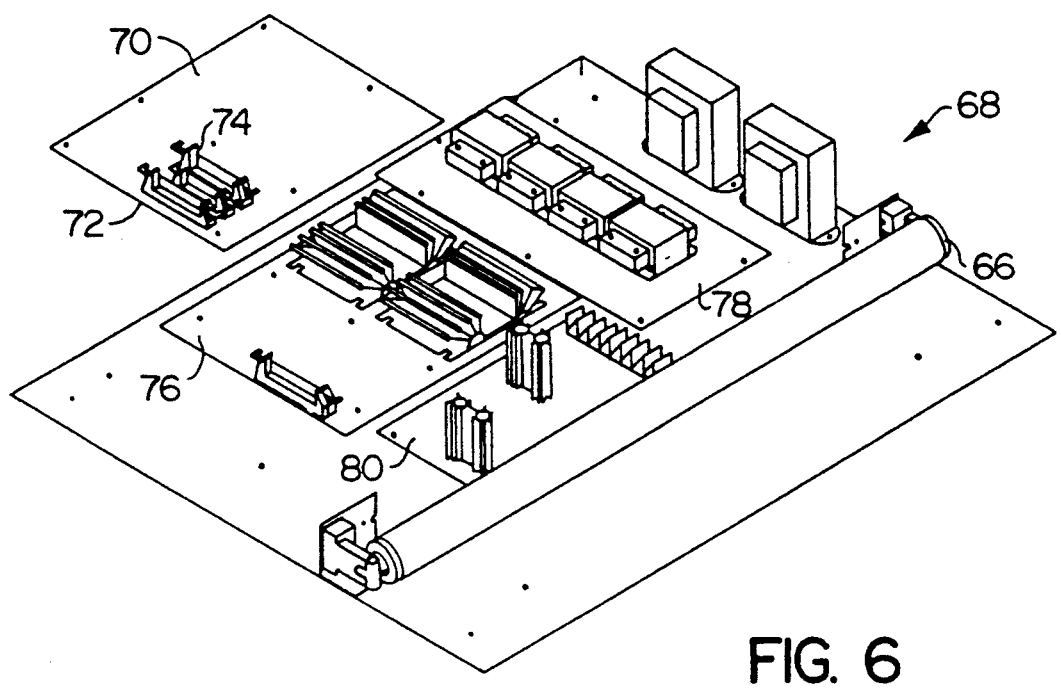
FIG. 6 is an isometric view of an electronic board controlling a scanner, including a CPU board, a power board, a motor board, and a power supply.

Referring to FIG. 6, there are shown the internal electronics boards located near to transmission lamp 66. These boards include a CPU board 70 including a microprocessor (80186) and a small computer system interface (SCSI). Also provided is a motor board 76, a power board 78, and a power supply 80 together forming an internal electronics board 68. These are described in more detail below. The power board powers and controls the transmission and reflectance lamps. Direct current is used to power the lamps for increased control.

ELECTRICAL HARDWARE DESIGN

The electrical hardware of the scanner includes four printed circuit boards. These boards include (1) a CPU board that contains the central microprocessor and controls the scanner operation, (2) a CCD board that contains the charge-coupled device sensors and the associated analog circuitry, (3) a motor board that contains the analog control and power electronics that drive the stepper motor, and (4) a power board that contains the transformer and protection circuitry that connects the scanner to the AC power line.

CPU BOARD

Referring to FIGS. 12A through 12C, the heart of the CPU board is an 80186 microprocessor 500. Microprocessor 500 is responsive to a 16 bit data bus 502, through which it communicates to 64 kilobytes of static RAM memory (in chips 504, 505, 506, and 507), and to various peripherals, including a SCSI interface chip 508 (that connects the scanner to the host computer), a digital-to-analog (D/A) converter (not shown) through data bus 510, and an analog-to-digital (A/D) converter (not shown) through data lines 512.

The static RAM memory chips and the peripherals are addressed and enabled by a 16 bit CPU address bus 514. Address values are written to the address bus 514 from the data bus 502 through three latches 515, 516, 517. The bottom 16 bits of the data bus are written to the CPU memory chips 504, 505, 506, 507. The top three bits are decoded by two decoders 518, 519, 520 (and flip-flops 521, 522) and are used to enable the CPU memory, enable the SCSI interface chip, or write data to the D/A converter data bus 510 (through buffers 524, 525) or A/D converter data lines 512 (through buffers 526, 527). In this way, one-eighth of the processor's address space is mapped to the CPU memory, one-eighth to the SCSI interface, and one-eighth to the A/D converter and D/A converters, respectively.

In addition to the above functionality, the contents of the CPU address bus may be written directly to a server I/O port 528 through buffers 530, 531, and to a tone generator 532 (for producing audible signals) through buffer 533.

The A/D converter output supports auto-ranging (see FIG. 13A and discussion below). Therefore, the A/D output must be decoded before being presented to the CPU data bus. This function is performed by the decoders 534, 535, 536, 537, 538. Auto-ranging may be enabled or disabled by the user through the SCSI port.

During operation, the microcode that controls microprocessor 500 is resident in the static RAM memory chips 504, 505, 506, 507. This microcode is downloaded to the scanner through the SCSI interface when the scanner is initialized. The assembly language file 3710.ASM contains the microcode used by the scanner; a full print-out of this file is provided in microfiche Appendix B.

CCD BOARD

Referring to FIGS. 13A through 13C, the central component of the CCD board is the CCD chip 550, which contains a 5000 CCD array, and is available from Toshiba, 9775 Toledo Way, Irvine, Calif., 92178, under part number TCD106C. The CCD array is biased and controlled by digital control circuitry, comprising buffer amplifiers 552 and decoding chips 554. The output of the CCD chip 550 is fed to analog decoding circuitry (see FIG. 13A).

The output of the CCD chip 550 is pre-processed by analog circuitry comprising op-amps 556, 558 and auto-ranging circuitry. Op-amp 558 is a non-inverting variable gain amplifier. The gain of op-amp 558 is set by selecting one of four gain resistors 560. The gain resistors 560 are selected by MOS switches in chip 562, in response to digital selection signals from decoding chip 564. The resistor selected is determined from the output of four comparators 566 which compare the buffered CCD output (from op-amp 556) to threshold voltages derived from the reference and a resistor array 558. As discussed above, the auto-ranging circuit may be disabled when desired.

The (possibly gain-adjusted) CCD output is input to the A/D converter 560 for conversion to a binary word 562. This binary word, along with three range bits on lines 564, are presented to the decoding circuitry on the CPU board.

The offset balance of the analog processing circuitry is adjusted by a D/A converter 566. The reference voltages supplied to the D/A converter 566, A/D converter 560, and resistor array 558 are produced by a 7.5 volt Zener diode 567 along with op-amps 570 and gain resistors.

MOTOR BOARD

Referring to FIGS. 14A through 14C, the motor controller board drives the stepper motor as well as the three florescent lamps. The motor is driven from a twelve volt motor supply voltage on line 600. This voltage is supplied to the motor on line 602 through a discrete D/A converter formed by four power transistors 604. Zero, one, two, three, or four of these transistors may be energized by setting the motor control bits on lines 606, thereby varying the output resistance seen by the motor and controlling the motor speed.

Each florescent lamp is controlled by a separate control circuit, however, the three control circuits have identical design. Each control circuit comprises a D/A converter 608 for producing an analog control voltage on lines 610. This voltage is filtered by op-amps 612 and used to control the current output to the florescent lamps. A transistor circuit comprising four power FET's 614 and two optical isolators 616 control the current flow and also supplies the lamps with a doubled power voltage for initial ionization.

A bipolar A/D converter 618 reads back the lamp currents (as sensed by sense resistors 620) and returns a digital representation of the current to microprocessor 500. The microcode in the microprocessor then adjusts the output of the appropriate D/A converter 608 to maintain a constant current state.

The current loop circuit is configured for bi-directional currents (for example, a bipolar A/D converter is used). Bi-directional lamp currents eliminate darkening of the lamps at one end. In the current embodiment, this bi-directional feature is not utilized.

POWER BOARD

Referring to FIG. 15, the power board contains the transformers that are used to create the power voltages for the analog and digital circuitry as well as the lamps and motor.

The following tables list the parameter values and components used in the circuit boards depicted in the schematics of FIGS. 12A through 15. Although the Figures provide sufficient detail to enable one skilled in the art to practice the invention, the following tables are a useful adjunct.

| Quantity | Location | Description | |
|---|---|---|---|
| | | | CPU Board |
| 1 | SPK1 | AUDIO OUTPUT | : PIEZOELECTRIC VARIABLE, 25V P-P, 0.001 A, MAX, PCB |
| 4 | C20,31,33,35 | CAPACITORS | : FIXED, 010, MF, 20%, 035, ELECTROLYTIC, AXIAL |
| 2 | C9,10 | CAPACITORS | : FIXED, 022, PF, 10%, 100, GLASS |
| 17 | C1-8,11-19 | CAPACITORS | : FIXED, 0.1, MF, 20%, 050, GLASS |
| 12 | C21-30,32,34 | CAPACITORS | : FIXED, 0.1, MF, 20%, 050, GLASS |
| 1 | Y1 | CRYSTALS/OSCILLAT | : 16.000, 0.02, PC BOARD, XTAL |
| 1 | Y2 | CRYSTALS/OSCILLAT | : 40.000, 0.01, PC BOARD, OSC, MODULE |
| 3 | U8,18,27 | DIGITAL TTL | : 74S, 373 |
| 3 | U3,10,24 | DIGITAL TTL | : 74HCTLS, 244, N |
| 5 | U1,2,4,11,13 | DIGITAL TTL | : 74HCTLS, 374, N |
| 1 | U14 | DIGITAL TTL | : 74HCTLS, 374, N |
| 2 | U5,15 | DIGITAL TTL | : 74HCTLS, 245, N |
| 1 | U23 | DIGITAL TTL | : 74HCTLS, 74, N |
| 1 | U28 | DIGITAL TTL | : 74S, 74, N |
| 1 | D1 | DIODES | : SILICON, PCB - 0.5", 1N914 |
| 1 | D2 | DIODES | : SILICON, 2.0 A, 1000 V, PCB - 0.5", SK5010A |
| 1 | U9 | LSI | : MICRO PROCESSOR, 80186 |
| 1 | U25 | LSI | : SCSI INTERFACE, 53C90 |
| 2 | U6,16 | MEMORY | : SRAM, 32, 08, DIP - 28 PIN |
| 5 | | PALS | : REG AND-OR-XOR, 10, 02, 02, PAL16L8AJC |
| 1 | R2 | RESISTORS | : FIXED, 1.00, 100000, 05%, 0.250 W (1/4), CARBON |
| 2 | R5,6 | RESISTORS | : NETWORK, 4.70, 1000, 01%, 0.0625 W (1/16), MRYSL FI |
| 1 | R1 | RESISTORS | : FIXED, 5.60, 1000, 05%, 0.250 W (1/4), CARBON |
| 1 | J5 | SOCKETS/PLUGS | : HEADER-ST, EJECTORS, 3M, MALE, 26, 0.100, 0.100 (DUAL) |
| 2 | U7, 17 | SOCKETS/PLUGS | : IC SOCKET, 28, 0.100, 0.600 |
| 1 | U9 | SOCKETS/PLUGS | : IC SOCKET, CARRIER, 68 |
| 1 | U25 | SOCKETS/PLUGS | : IC SOCKET, PLCC, FEMALE, 68, 0.100, 0.100 (DUAL), BE |
| 2 | J4,6 | SOCKETS/PLUGS | : HEADER-ST, EJECTORS, 3M, MALE, 40, 0.100, 0.100 (DUAL) |
| 1 | | SYSTEM 3710 PARTS | : , BARE PCB, CPU BD |
| 1 | | SYSTEM 3710 PARTS | : , PROGRAMMED PROM, CPU BD, LOW BYTE |
| 1 | | MEMORY | : PROM, 32M 08, DIP - 28 PIN |
| 1 | | SYSTEM 3710 PARTS | : , CPU BD, SCANNER FIRMWARE, PROMWARE |
| 1 | | SYSTEM 3710 PARTS | : , PROGRAMMED PROM, CPU BD, HIGH BYTE |
| 1 | | MEMORY | : PROM, 32, 08, DIP - 28 PIN |
| 1 | | SYSTEM 3710 PARTS | : , CPU BD, SCANNER FIRMWARE, PROMWARE |
| | | | CCD Board |
| | | | : FIXED, 0.1, MF, 20%, 050, GLASS |
| 11 | C1-C3,C10-C17 | CAPACITORS | : FIXED, 0.1, MF, 20%, 050, GLASS |
| 5 | C20,C22-C26 | CAPACITORS | : FIXED, 0.1, MF, 20%, 050, GLASS |
| 2 | C29,C30 | CAPACITORS | : FIXED, 0.1, MF, 20%, 050, GLASS |
| 3 | C33,C34,C35 | CAPACITORS | : FIXED, 0.1, MF, 20%, 050, GLASS |
| 3 | C38,C39,C42 | CAPACITORS | : FIXED, 0.1, MF, 20%, 050, GLASS |
| 6 | C4-C9 | CAPACITORS | : FIXED, 1000, PF, 050, GLASS |
| 1 | C18 | CAPACITORS | : FIXED, 560, PF, 05%, 063, POLYSTYRENE/FOIL, AXIAL |
| 3 | C21,C27,C28 | CAPACITORS | : FIXED, 010, MF, 10%, 020, TANTALUM, AXIAL |
| 3 | C32,C47,C40 | CAPACITORS | : FIXED, 010, MF, 10%, 020, TANTALUM, AXIAL |
| 1 | C41 | CAPACITORS | : FIXED, 010, MF, 10%, 020, TANTALUM, AXIAL |
| 1 | U13 | CONVERTERS | : D/A, DIP 20 PIN, 12, +5 TO +15, DAC1232LCJ, UP COMPA |
| 1 | U10 | CONVERTERS | : A/D, 08, AD7821 |
| 1 | U12 | DETECTOR | : ARRAY, 5000, CCD LINEAR SENSOR, TCD106C |
| 2 | U1,U2 | DIGITAL TTL | : 74HCTLS, 244, N |
| 1 | U8 | DIGITAL TTL | : 74HCTLS, 191, N |
| 1 | U3 | DIGITAL TTL | : 74HCTLS, 74, N |
| 3 | D1,D2,D3 | DIODES | : SILICON, PCB - 0.5", 1N914 |
| 1 | D5 | DIODES | : ZENER, 007.5 V, PCB - 0.5", 1N4693 |
| 1 | D3 | DIODES | : ZENER, 013 V, PCB - 0.5", 1N4700 |
| 2 | D7,D8 | DIODES | : SCHOTTKY, 1.0 A, 040 V, PCB - 0.5", 1N5819 |
| 3 | Q1,Q2,Q3 | FET | : N CHANNEL MOSFET, SIGNAL, TO-72,070 OHMS, 0.05A, 02 |

-continued

| Quantity | Location | Description | |
|---|---|---|---|
| 1 | U17 | FET | : N CHANNEL MOSFET, SIGNAL, 16, PIN DIP, 070 OHMS, 0.05 |
| 2 | U11,U15 | OP AMPS | : COMPARATOR, BIPOLAR, 05 TO 18 (+/−), DIP 14 PIN, LM3 |
| 1 | U18 | OP AMPS | : LINEAR, JFET, 05 TO 18 (+/−), DIP 14 PIN, LF347, 4 |
| 2 | U9,U14, | OP AMPS | : LINEAR, BIPOLAR, 05 TO 18 (+/−), DIP 8 PIN, LM6161, |
| 2 | U4,U16 | PALS | : REG AND-OR, 10, 02, 00, PAL16R8AJC |
| 2 | R27,R30 | RESISTORS | : FIXED, 2.20, 100, 05%, 0.250 W (1/4), COMPOSITION |
| 1 | R34 | RESISTORS | : FIXED, 1.00, 100000, 01%, 0.125 W (1/8), METAL FILM |
| 3 | R7,R24,R36 | RESISTORS | : FIXED, 1.00, 1000, 05%, 0.250 W (1/4), CARBON |
| 4 | R14-R17 | RESISTORS | : FIXED, 3.30, 1000, 05%, 0.250 W (1/4), CARBON |
| 1 | R25 | RESISTORS | : FIXED, 1.50, 1000, 05%, 0.250 W (1/4), CARBON |
| 2 | R18,R21 | RESISTORS | : FIXED, 2.20, 1000, 05%, 0.250 W (1/4), CARBON |
| 1 | R8 | RESISTORS | : FIXED, 4.70, 10000, 05%, 0.250 W (1/4), CARBON |
| 1 | R45 | RESISTORS | : NETWORK, 4.70, 1000, 01%, 0.0625 W (1/16), METAL FI |
| 2 | R11,R12 | RESISTORS | : FIXED, 1.00, 100, 01%, 0.125 W (1/8), METAL FILM |
| 3 | R13,R23,R32 | RESISTORS | : FIXED 1.00, 10000, 01%, 0.125 W (1/8), METAL FILM |
| 2 | R55,R56 | RESISTORS | : FIXED, 1.00, 10000, 01%, 0.125 W (1/8), METAL FILM |
| 1 | R40 | RESISTORS | : FIXED, 2.00, 10000, 01%, 0.125 W (1/8), METAL FILM |
| 3 | R26,R33,R38 | RESISTORS | : FIXED, 2.00, 10000, 01%, 0.125 W (1/8), METAL FILM |
| 7 | R1-R6,R20 | RESISTORS | : FIXED, 3.30, 100, 05%, 0.250 W (1/4), CARBON |
| 2 | R28,R29 | RESISTORS | : FIXED, 3.30, 100, 05%, 0.250 W (1/4), CARBON |
| 1 | R37 | RESISTORS | : FIXED, 4.70, 100, 05%, 0.250 W (1/4), CARBON |
| 1 | R10 | RESISTORS | : FIXED, 2.00, 100, 01%, 0.125 W (1/8), METAL FILM |
| 1 | R9 | RESISTORS | : FIXED, 4.02, 100, 01%, 0.125 W (1/8), METAL FILM |
| 1 | R41 | RESISTORS | : FIXED, 1.24, 1000, 01%, 0.125 W (1/8), METAL FILM |
| 1 | R42 | RESISTORS | : FIXED, 2.74, 1000, 01%, 0.125 W (1/8), METAL FILM |
| 1 | R43 | RESISTORS | : FIXED, 6.49, 1000, 01%, 0.125 W (1/8), METAL FILM |
| 1 | R44 | RESISTORS | : FIXED, 1.96, 10000, 01%, 0.125 W (1/8), METAL FILM |
| 1 | R31 | RESISTORS | : FIXED, 1.69, 10000, 01%, 0.125 W (1/8), METAL FILM |
| 3 | R50,R51,R53 | RESISTORS | : VARIABLE-25 TURN, 1.00, 10000, 10%, 0.500 W (1/2), |
| 1 | R49 | RESISTORS | : VARIABLE-25 TURN, 1.00, 1000, 10%, 0.500 W (1/2), C |
| 2 | R46,R47 | RESISTORS | : VARIABLE-25 TURN, 2.00, 100, 10%, 0.500 W (1/2), CE |
| 1 | R48 | RESISTORS | : VARIABLE-25 TURN, 5.00, 100, 10%, 0.500 W (1/2), CE |
| 1 | R35 | RESISTORS | : FIXED, 4.70, 1000, 05%, 0.125 W (1/8), METAL FILM, |
| 1 | R22 | RESISTORS | : FIXED, 5.11, 1000, 01%, 0.125 W (1/8), METAL FILM, |
| 1 | R52 | RESISTORS | : VARIABLE-25 TURN, 5.00, 10000, 10%, 0.500 W (1/2), |
| 3 | U5,U6,U7 | SIGNAL INTERFACE | TTL, MOS, 8 PIN DIP, DS0026 |
| 1 | CN3 | SOCKETS/PLUGS | : HEADER-R<, EJECTORS, 3M, MALE, 40, 0.100, 0.100 (DUAL |
| 1 | TP2 | SOCKETS/PLUGS | : TEST POINT, FEMALE, 01, 0.400, SILVER/BLACK |
| 1 | TP1 | SOCKETS/PLUGS | : TEST POINT, FEMALE, 01, 0.400, SILVER/RED |
| 1 | CN4 | SOCKETS/PLUGS | : HEADER-RT.ANGLE, ANGLE, MOLEX, MALE, 24, 0.156, TIN |
| 1 | | SYSTEM 3710 PARTS | : , BARE PCB, CCD BD |

Motor Board

| Quantity | Location | Description | |
|---|---|---|---|
| 10 | C4-8,13-17 | CAPACITORS | : FIXED, 0.1, MF, 20%, 050, GLASS |
| 6 | C23-25,27-29 | CAPACITORS | : FIXED, 0.1, MF, 20%, 050, GLASS |
| 3 | C32-34 | CAPACITORS | : FIXED, 0.1, MF, 20%, 050, GLASS |
| 4 | C3,10,19,22 | CAPACITORS | : FIXED, 0.01, MF, GMV (−0%), 600, CERAMIC, RADIAL |
| 2 | C30,31 | CAPACITORS | : FIXED, 0.01, MF, GMV (−0%), 600, CERAMIC RADIAL |
| 3 | U2,3,6 | CONVERTERS | : D/A, DIP 20 PIN, 12, +5 TO +15, DAC1232LCJ, UP COMPA |
| 1 | U11 | CONVERTERS | : A/D, DIP 28 PIN, 08, +5, ADC0809CCN, 8 CHANNEL INP M |
| 2 | U15,16 | DIGITAL TTL | : 74HCTLS, 374, N |
| 1 | U7 | DIGITAL TTL | : 74HCTLS, 191, N |
| 1 | U14 | DIGITAL TTL | : 74HCTLS, 240, N |
| 6 | D1,4,7,8,14,18 | DIODES | : ZENER, 033 V, PCB - 0.5", 1N4714 |
| 1 | D17 | DIODES | : ZENER, 004.3 V, PCB - 0.5", 1N4687 |
| 9 | D2,3,5,6,9-13 | DIODES | : SILICON, 2.0 A, 1000 V, PCB - 0.5", SK5010A |
| 3 | D15,16,19 | DIODES | : SILICON, 2.0 A, 1000 V, PCB - 0.5", SK5010A |
| 11 | Q3,4,7-9,12-17 | FET | : N CHANNEL MOSFET, 125 W, TO-220, 0.22 OHMS, 16A, 150 |
| 6 | Q1,2,5,6,10,11 | FET | : P CHANNEL MOSFET, 125 W, TO-220, 0.7 OHMS, 09A, 150V |
| 6 | | HEATSINKS/ETC. | : TO-220, INSULATOR, SILICONE RUBBER |
| 4 | U1,4,8,12 | OP AMPS | : LINEAR, JFET, 05 TO 18 (+/−), DIP 14 PIN, LF347, 4 |
| 5 | U5,9,10,13,17 | OPTOISOL/INTRPT | : OPTOISOLATOR, DIP - 8 PIN, 0.06 A, 30V/0.03A |
| 1 | U18 | OPTISOL/INTRPT | : OPTOISOLATOR, DIP - 8 PIN, 0.06 A, 30V/0.03A |
| 5 | R9,15,31,38,48 | RESISTORS | : FIXED, 1.00, 10000, 05%, 0.250 W (1/4), CARBON |
| 4 | R50,51,56,61 | RESISTORS | : FIXED, 1.00, 10000, 05%, 0.250 W (1/4), CARBON |
| 4 | R20,21,39,40 | RESISTORS | : FIXED, 1.50, 100, 05%, 0.250 W (1/4), CARBON |
| 4 | R49,65,66,72 | RESISTORS | : FIXED, 1.50, 100, 05%, 0.250 W (1/4), CARBON |
| 3 | R73-75 | RESISTORS | : FIXED, 1.50, 100, 05%, 0.250 W (1/4), CARBON |
| 1 | R81 | RESISTORS | : NETWORK, 4.70, 01%, 0.625 W (1/16), METAL FILM |
| 6 | R5-7,10,12,13 | : RESISTORS | : FIXED, 1.00, 10000, 01%, 0.125 W (1/8), METAL FILM |
| 5 | R17-19,26,28 | RESISTORS | : FIXED, 1.00, 10000, 01%, 0.125 W (1/8), METAL FILM |
| 5 | R29,35-37,44 | RESISTORS | : FIXED, 1.00, 10000, 01%, 0.125 W (1/8), METAL FILM |
| 4 | R46,47,53,58 | RESISTORS | : FIXED, 1.00, 10000, 01%, 0.125 W (1/8), METAL FILM |
| 1 | R82 | RESISTORS | : NETWORK, 1.00, 1000, 01%, 0.0625 W (1/16), METAL FILM |
| 4 | R70,71,76,77 | RESISTORS | : FIXED, 1.50, 10, 01%, 05 W, WIRE BOUND |
| 1 | R52 | RESISTORS | : FIXED, 2.70, 1, 05%, 01 W, CARBON |
| 4 | R23,24,41,42 | RESISTORS | : FIXED, 4.70, 1000, 05%, 0.250 W (1/4), CARBON |
| 3 | R59,68,69 | RESISTORS | : FIXED, 4.70, 1000, 05%, 0.250 W (1/4), CARBON |
| 4 | R8,14,30,33 | RESISTORS | : FIXED, 5.60, 1000, 05%, 0.250 W (1/4), CARBON |
| 2 | R57,62 | RESISTORS | : FIXED, 5.60, 1000, 05%, 0.250 W (1/4), CARBON |
| 4 | R4,11,16,27 | RESISTORS | : FIXED, 2.80, 10000, 01%, 0.250 W (1/8), METAL FILM |
| 4 | R34,45,54,55 | RESISTORS | : FIXED, 2.80, 10000, 01%, 0.250 W (1/8), METAL FILM |

-continued

| Quantity | Location | Description | |
|---|---|---|---|
| 3 | R25,43,67 | RESISTORS | : FIXED, 4.02, 1, 01%, 03 W, WIRE WOUND |
| 2 | R60,64 | RESISTORS | : FIXED, 1.00, 10, 01%, 05 W, WIRE WOUND |
| 3 | R22,32,63 | RESISTORS | : FIXED, 1.00, 100000, 05%, 0.500 W (1/2), CARBON |
| 6 | | SCREWS | : PAN HEAD-PHILLIPS, 04–40, 0.1875 (3/16) |
| 1 | J1 | SOCKETS/PLUGS | : HEADER-ST, EJECTORS, 3M, MALE, 40, 0.100, 0.100 (DUAL) |
| 1 | J3 | SOCKETS/PLUGS | : HEADER-ST, EJECTORS, 3M, MALE, 10, 0.100, 0.100 (DUAL) |
| 1 | J2 | SOCKETS/PLUGS | : HEADER-ST. LOCK, MOLEX, MALE, 24M 0.156, TIN |
| 1 | | SYSTEM 3710 PARTS | : , BARE PCB, MOTOR BD |
| 1 | | SYSTEM 3710 PARTS | : HEAT SINK W/HOLES, MOTOR BD, MODIFIED HEAT SINK |
| 1 | | HEATSINKS/ETC. | : PC BOARD-FLAT, 141, HEAT SINK |
| 6 | | WASHERS | : INSULATE/SHOULDER, 04, POLYPHENYLENE SULF |
| | | Power Board | |
| 1 | C1 | CAPACITORS | : FIXED, 2200, MF, 063, ELECTROLYTIC, AXIAL |
| 8 | D1-8 | DIODES | : SILICON, 2.0 A, 1000 V, PCB - 0.5:, SK5010A |
| 3 | BR1-3 | OPTISOL/INTRPT | : SOLID STATE RELAY, PCB MOUNT - 4 PIN, 0.005 A, 280VA |
| 1 | F1 | POWER ENTRY | : FUSE HOLDER, 15, 1.46 × 0.5, PRINTED CIRCUIT |
| 5 | TB1 | SOCKETS/PLUGS | : BAR. STRP PC MOUNT, 10, 0.200, 22-12, WIRE CLAMPING |
| 1 | J6 | SOCKETS/PLUGS | : HEADER-ST, EJECTORS, 3M, MALE, 10, 0.100, 0.100 (DUAL) |
| 1 | J3 | SOCKETS/PLUGS | : HEADER-ST, MOLEX, MALE, 24, 0.156, TIN |
| 1 | | SYSTEM 3710 PARTS | : , BARE PCB, POWER BD |
| 3 | T1-3 | TRANSFORMER | : 115/230 50/60, 8 V, .75 A, DUAL, PC MOUNT |
| 1 | T4 | TRANSFORMER | : 115/230 50/60, 115 V, .05A, DUAL, PC MOUNT |

SOFTWARE DESIGN

One difficulty with present image scanning and processing systems is that, typically, configuring the system to perform specialized tasks requires intimate knowledge of the operation of the system, and an understanding of computer programming. This difficulty is enhanced by the fact that several types of intermediate data files are produced during the processing of an image. The overhead that is required to simply manage the various files of data can be taxing on even experienced users.

One field where these difficulties are apparent is that of automated analysis of electrophoretic gels. In this field, the image of the gel must be processed to locate bands or spots, and the bands or spots must be sequenced. These difficulties are reduced or overcome as described below.

TOOLS, APPLICATIONS, SESSIONS

One aspect of the software design of the invention is its general programmability. There are several independent software "tools" (defined by independent source code files in microfiche Appendix B) that may be invoked to perform image processing. Typically, an analysis of, e.g., an electrophoretic gel comprises the sequential invocation of a sequence of these tools, using as input one or more scanned image files and creating as output one or more final or intermediate data files.

When a sequence of tools is used to perform an overall task, the sequence is an interpretive program, known as an "application". To customize the system, the user creates application files that describe sequences of tools corresponding to applications, as well as their input and output files. A complex operation involving several tools and potentially producing several intermediate files may then be performed by executing the operations indicated in the pre-defined application file.

Each time an application is invoked, a "session" is created. In a broad sense, an application may be considered to be the series of tools that process image data, whereas the session also includes the particular data being processed and the state of that data during processing.

When a session begins, the files that store the application sequence and any intermediate files are copied to new files under the session name. Thereafter, during the session, the user may modify the application, run the application, backstep and modify the application, re-run the application, and so on until any desired result is accomplished. As the session runs the application, each item in the application sequence is "checked-off" in the session's application file, and at the completion of the session the application copy is checked-off.

One important advantage to this scheme is that the "state" of each session is automatically stored and may be retrieved. Therefore, the user may have several sessions pending at any one time, or may recall a previous session and review the results and/or state of the session after its last use. This allows the user to run the same applications on different data, and view the results in parallel. Furthermore, several different applications may be run in parallel and the results viewed in parallel. Also, the session provides for simplistic management of the intermediate data produced by the image processing, because each of the intermediate files is automatically cross-referenced to the application version that created it and the other intermediate files or data files that it is related to.

MENUS

It is important that the creation and editing of an application be as user-friendly as possible. To accomplish this, the editing system is fully "menu driven". This means that, when the user is performing operations to create an application, the choices available at each step are displayed in menus—the user is not forced to remember the choices. Furthermore, the menus are context-sensitive. That is, the items in the menu are only those that are relevant to the current situation. This prevents the user from making incorrect choices from the menu, and reduces confusion.

Referring to FIG. 16A, the initial menu presented to the user has four options: Create/Edit/Run, Recall Session, Utilities, and Exit.

Figure 16B:
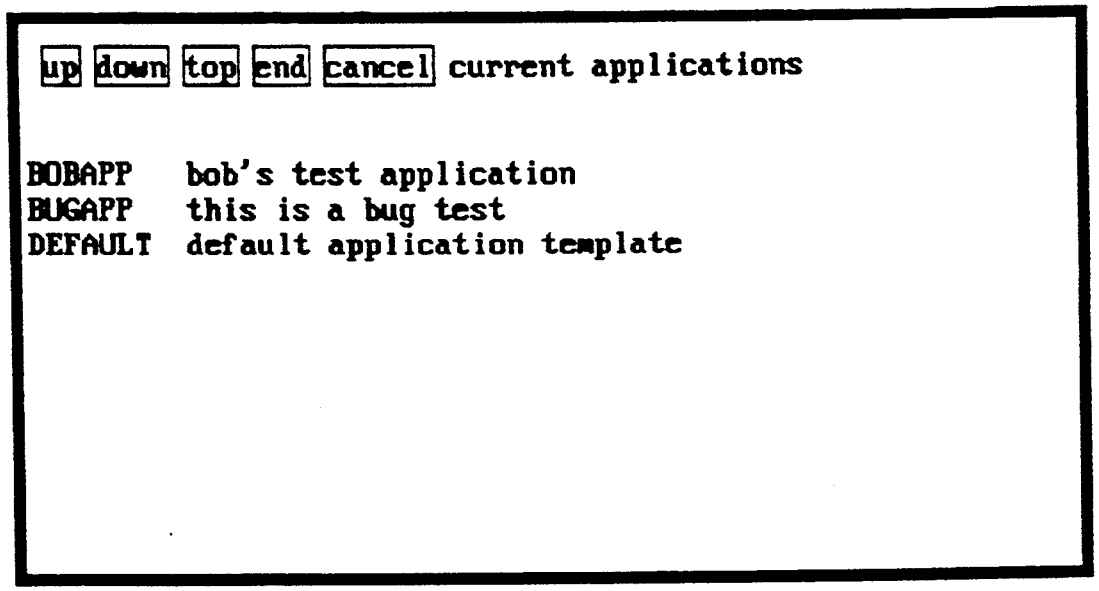

Referring to FIG. 16B, if the user selects Create/Edit/Run, to facilitate editing of existing applications, a list of the existing applications (which are defined by .CLF command language file—see Appendices A and B) is initially displayed to the user, and the user is allowed to select an application from the list for running or editing. When moving through the list of applications, the user may use one of the following commands: Up (move up one item in the list), Down (move down one item), Top (move to the top of the list), End (move to the end of the list), or Cancel (belay the Create/Edit/Run command).

Figure 16C:
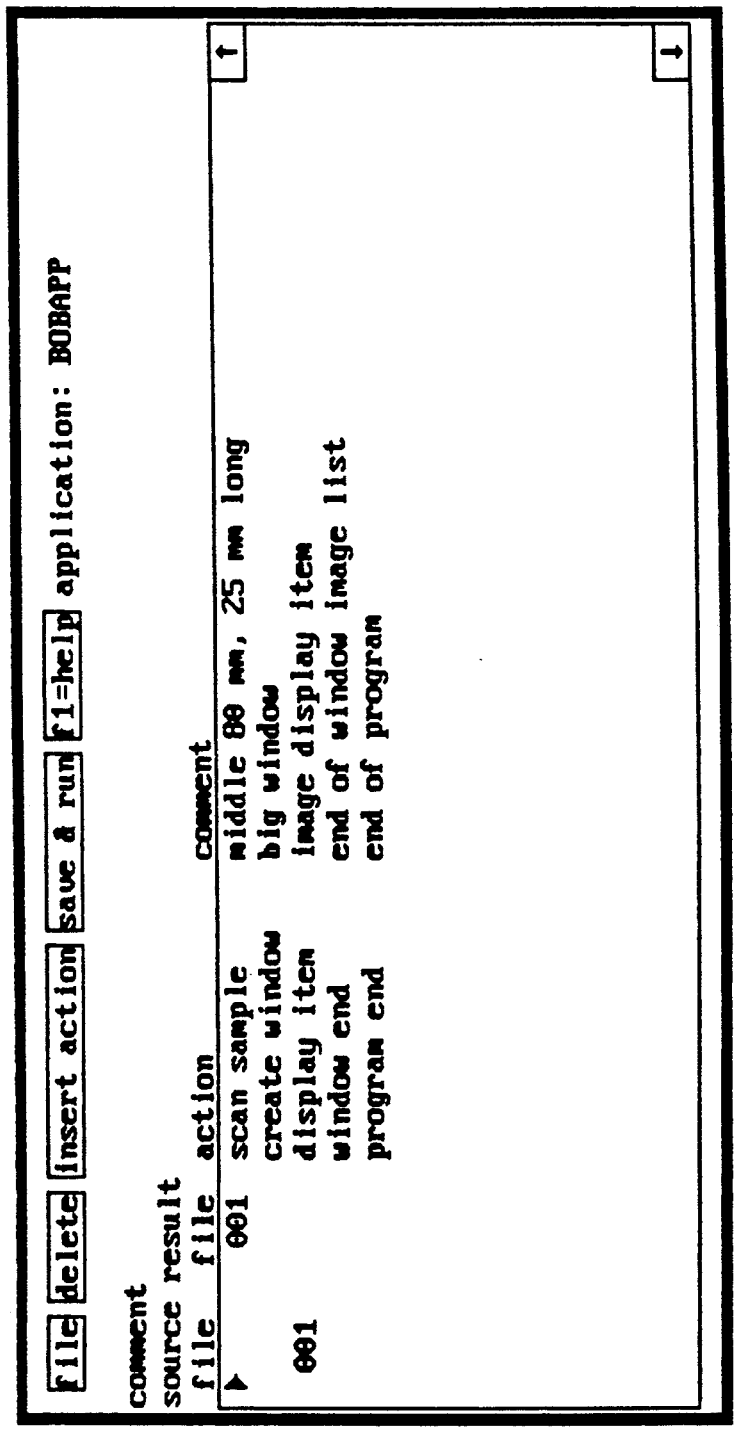

Referring to FIG. 16C, the user has now selected the application named BOBAPP. The application is presented as a series of natural language identifiers (e.g., scan sample, create window) that describe actions and their related source files and result files in an editing window. The editing window allows the user to edit the existing application, or define a new one. While editing, the user may use the various editing commands (see below) available at the top of the window to, for example, add tools to the application sequence, or save the application to a file name.

The application BOBAPP scans a sample (Scan Sample) that is 80 mm wide and 25 mm long, and puts the result data into the file denoted by the number 001. Next, BOBAPP creates a large window (Create Window) and displays the resulting file (Display Item) in the window.

The actions performed by the applications may be arbitrarily defined by the user. For example, another application could scan a sample, find the spots on the sample, and create a display that compared the original image (in a small window) to the spots detected by the detection algorithm. An application which performs this function is as follows:

| Source File | Result File | Action (Tool Invocation) | Comment |
|---|---|---|---|
| | 000 | Scan Sample | A scan of a sample |
| 000 | 001 | Image Reduction | A 1 to 4 reduction |
| 001 | 002 | Image Reduction | A 1 to 2 reduction |
| 000 | 003 | Spot Find | Standard parameters |
| | | Create Window | Thin Top Window |
| 002 | | Display Image | Small image display |
| | | Window End | |
| | | Create Window | Large Window |
| 000 | | Display Image | Original Image display |
| 003 | | Display Spots | Display spot file |
| | | Window End | |
| | | Program End | |

Each of the rows in this list represents the invocation of one of the tools. Tools (for example, the image reduction tool) may be invoked more than once, depending upon the needs in the application. The parameters that are passed to the tool upon invocation may change the operation of the tool (for example, the image reduction tool may do a 1 to 2 or a 1 to 4 reduction). These parameters are not displayed above; however, the "comments" column indicates the effective action to be performed by the tool.

As seen in the above example and in FIG. 16C, the intermediate files created by image processing are identified by numerical identifiers. This is a significant advantage of the invention, because it allows the user to easily reference intermediate files without being concerned with long file names or other intermediate files created by other sessions. In a user-transparent fashion, the intermediate files are stored using the session name as a root and the file number as an extension in the form <session name>.<file number> (e.g., HELLO.002 for the second intermediate file in the session "HELLO").

Another important advantage of the invention is the heavy use of comments. Comments are generally more explanatory than code, primarily because comments are created by the programmer in whatever syntax was the most clear to the programmer (rather than the arbitrary syntax of the programming language). Therefore, the user's comments are used to indicate the actions being performed, rather than the parameters.

While an application is displayed, a new set of menus are available. These are entitled File (for manipulating application files), Delete (deletes the tool invocation above the insertion point; the insertion point is the small triangle at the left of FIG. 16C), Insert Action (adds a tool invocation at the insertion point), and Save and Run (saves the current version of the application in a file, and runs the application).

Figure 16D:
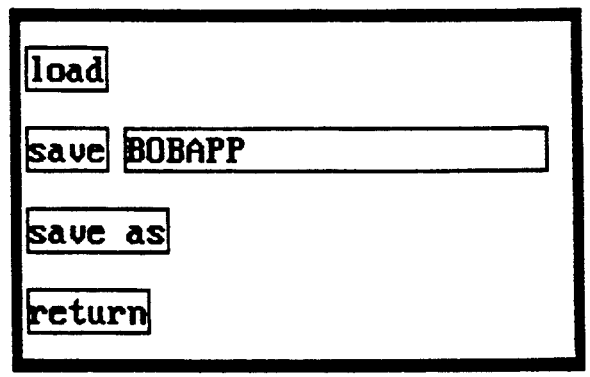

Referring to FIG. 16D, in the File menu, several operations may be performed. These include Load (loads another application file), Save (saves the current version of the application under its current file name, e.g. BOBAPP), Save as (saves the application under a file name provided by the user), and Return (returns to the previous screen).

Figure 16E:
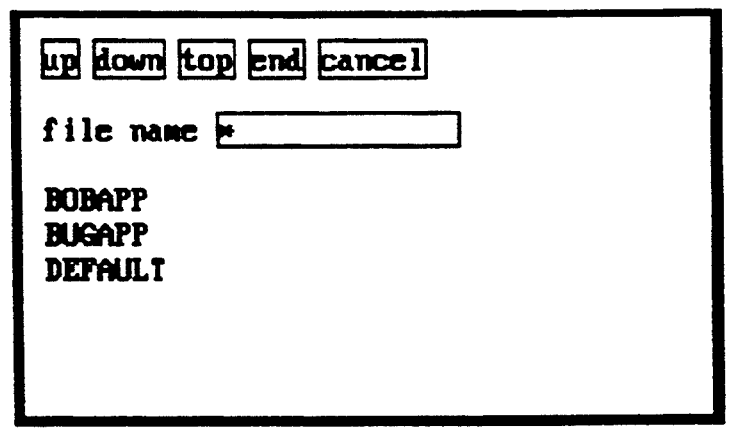

Referring to FIG. 16E, when Load is selected, a list of the available applications is displayed, and one may be selected in a fashion similar to that illustrated in FIG. 16B.

Referring to FIG. 16F, when Insert Action is selected from the edit window (FIG. 16C) menu, several tool invocations may be inserted into the application at the insertion point. The available options are displayed to the user in a menu. This menu is context sensitive—only those options which are currently relevant are displayed. For example, if the insertion point is within a window definition (i.e., between a Create Window line and a Window End line), only those options which concern the display of data are displayed in the menu.

In the embodiment of the invention encoded in the microfiche Appendix B, the Options which may be available for selection at any given time are Scan Sample, Create Window, Display Image, Image Reduction, Find Spots, Display Spots. Only those which are currently relevant will actually be displayed.

Other advanced actions could also be implemented, such as convolution of images, derivatives of images, or offsetting of images to change the background contrast, cut-and-pasting portions of images, and measuring distances on the image on the screen with the cursor. Other graphic and plotting capabilities could also be implemented.

In addition to the menu command, the application may be edited by placing the cursor on any of the tool command lines and clicking the mouse button. This will display the current parameters for that invocation of the tool, and allow the user to edit the parameters.

Referring to FIG. 16G, to edit the parameters of a Scan Sample command, the user clicks on the Scan Sample name from the editing window (FIG. 16C) menu. The result is a window displaying the scan parameters (i.e., the x and y dimensions, the resolution of the data storage, and the lamp to be used). By clicking on the various fields, the user is allowed to edit the parameters. Some of the parameter fields (such as the data storage field) produce menus of available options (see FIG. 16Y through 16AA). Others contain numerical values which are entered from the keyboard.

Clicking on the File command in FIG. 16G brings up a menu of files that contain pre-defined parameters (see the menu of image reduction parameters in FIG. 16K).

In this menu, the user may retrieve the parameters from a pre-defined file, or may save the current parameters to a file.

Clicking on the Comment field in FIG. 16G allows the user to change the comments (which are displayed in the main user and indicate generally the operations performed by the parameters).

Pushing Return or hitting the Escape key updates the scan size parameters in the application. Thereafter, the modified scan size will be used when scanning the sample.

Referring to FIG. 16H, clicking on a Create Window command displays the current window parameters for the window, and allows the user to edit them. In similar fashion to FIG. 16I, the File menu produces a list of the currently pre-defined window parameter files, and allows the user to select one or save the current parameters to one.

Referring to FIG. 16I, selecting any of the parameters relating to color in FIG. 16H (e.g., background or border color) results in a window showing the color hues available. The user is able to modify these as appropriate.

Referring to FIG. 16J, selecting any of the parameters relating to magnification in FIG. 16H results in a window showing the current magnification and the available options.

Figure 16L:
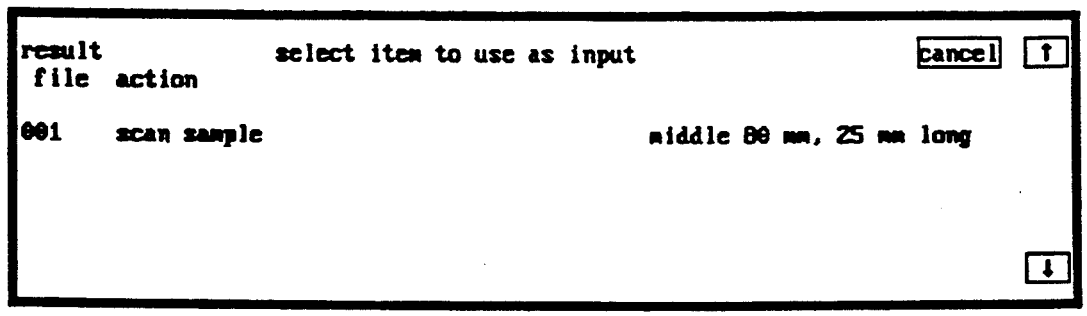

Referring to FIG. 16K, selecting any of the tool commands from the Select Action menu (FIG. 16F) results in a list of the pre-defined parameter files for that command type. For example, selecting an Image Reduction command displays a list of the pre-defined reduction parameter files; the user is allowed to select one. Referring to FIG. 16L, selecting one of the image reduction parameter files produces a window that displays the resulting command as it will appear in the application. The user can then edit the result file parameter (where necessary) and insert the command, or can cancel the command by clicking on the Cancel box.

Figure 16M:
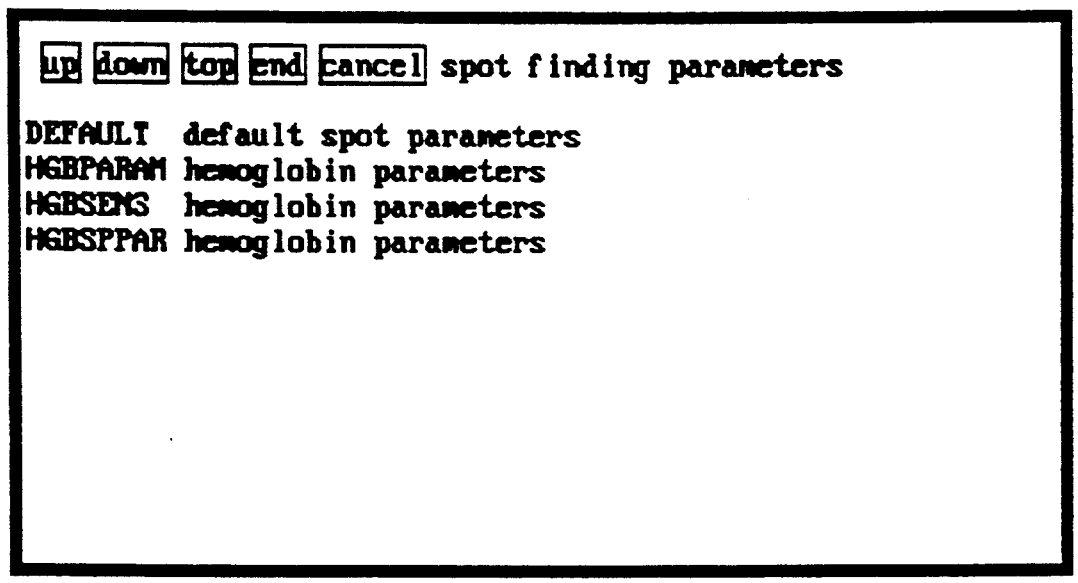

Referring to FIG. 16M, selecting Find Spots from the select action menu (FIG. 16F) displays a list of the previously defined spot finding parameter files and allows the user to select one.

Referring to FIG. 16N, selecting Find Spots creates a new menu asking the user to select which image file will serve as the input to the spot finding tool (similar screens are used for all other tools which use image files for input). Note that the sequence of files created by previous tools (e.g., the Image Reduction tool) is illustrated as a hierarchical tree, where each command and output file (e.g., 002) that uses another output file is connected graphically to that other output file. For example, in the FIG. a short line shows that the Image Reduction command (that will create file 002) will use as its input file, the file 001 created by the Scan Image command. This helps the user to understand the geneology of the available image files. The user can select one of the image files by clicking on one of the lines in the application, or can cancel by clicking on the Cancel box.

Referring to FIG. 16O, if the user clicks on a Find Spots command from the application window (FIG. 16C), the result is a menu of the current parameters for that command. The parameters may be edited by clicking on the appropriate fields, and/or parameter files may be created or retrieved through the File command.

RECALLING SESSIONS

Figure 16P:
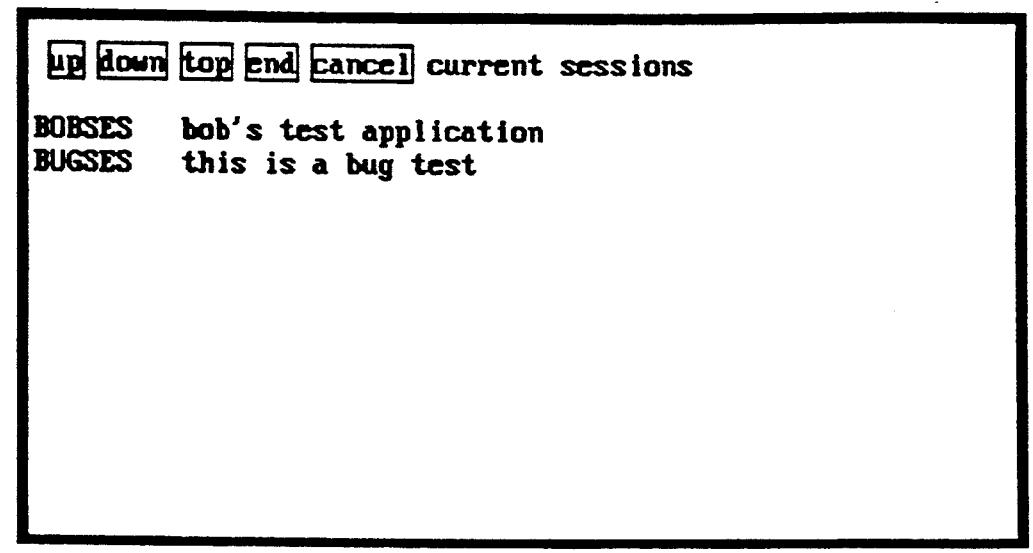

Referring to FIG. 16P, if the user selects Recall Session from the initial menu (FIG. 16A), a menu of the previous sessions is displayed, and the user is allowed to select one from the list for review. When moving through the list of sessions, the user may use one of the following commands: Up (move up one item in the list), Down (move down one item), Top (move to the top of the list), End (move to the end of the list), or Cancel (belay the Recall Session command).

Figure 16Q:
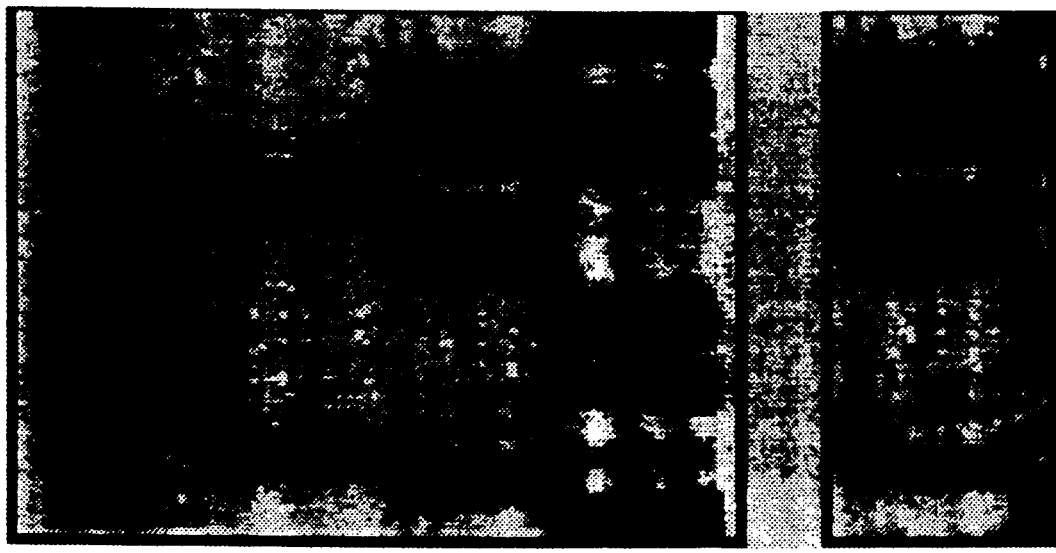

Referring to FIG. 16Q, selecting a session initializes the display to whatever its state was when the selected session was last exited. (Note that the last time this window was exited a scan result was being displayed.) During the session, another menu is displayed containing the options Program, Windows, Go and Done.

Figure 16R:
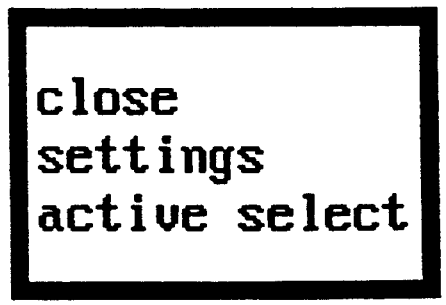
Figure 16S:
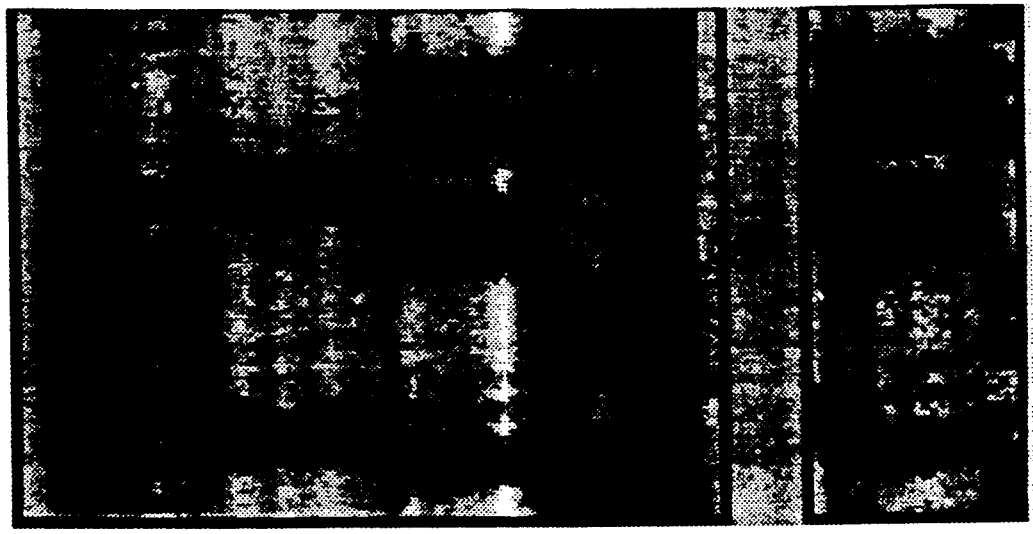

Referring to FIG. 16R, selecting Windows from FIG. 16Q provides the user with commands that manipulate the session's windows. The window to be manipulated by the commands is indicated by moving the cursor into the window and clicking the mouse button. The user may use the Active Select command to bring the window to the "front" of the screen, use the Close command to close it and remove it from the display, or use the Settings command to edit the settings that describe it. Referring to FIG. 16S, selecting any of these options will prompt the user to "Point to the window and Click". When the user does so, the selected action will be done to the indicated window.

Figure 16T:
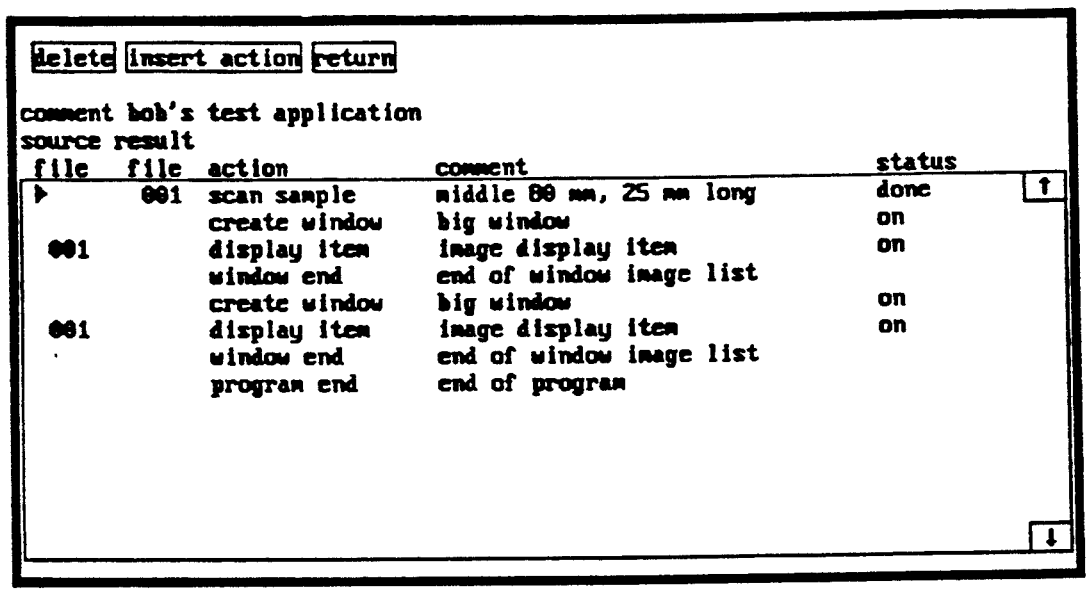

Referring to FIG. 16T, by selecting Program from the session menu (FIG. 16P), the user can retrieve the application used in the session, which will be displayed and can be edited in the same way as in application editing (FIG. 16C). However, an additional column, "status" is displayed to indicate the state of the execution of tools in the application.

Figure 16U:
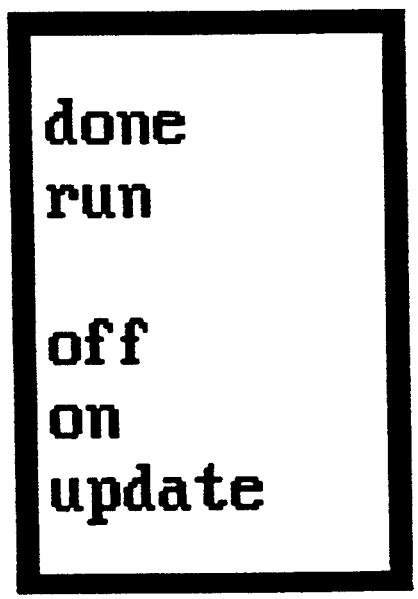

Referring to FIG. 16U, selecting any entry on the status column creates a menu that allows the user to modify the status of each tool in the application, thereby allowing the user to repeat execution of tools, skip execution of tools, or update the results of tools (after changing the tool's parameters).

HELP

Figure 16V:
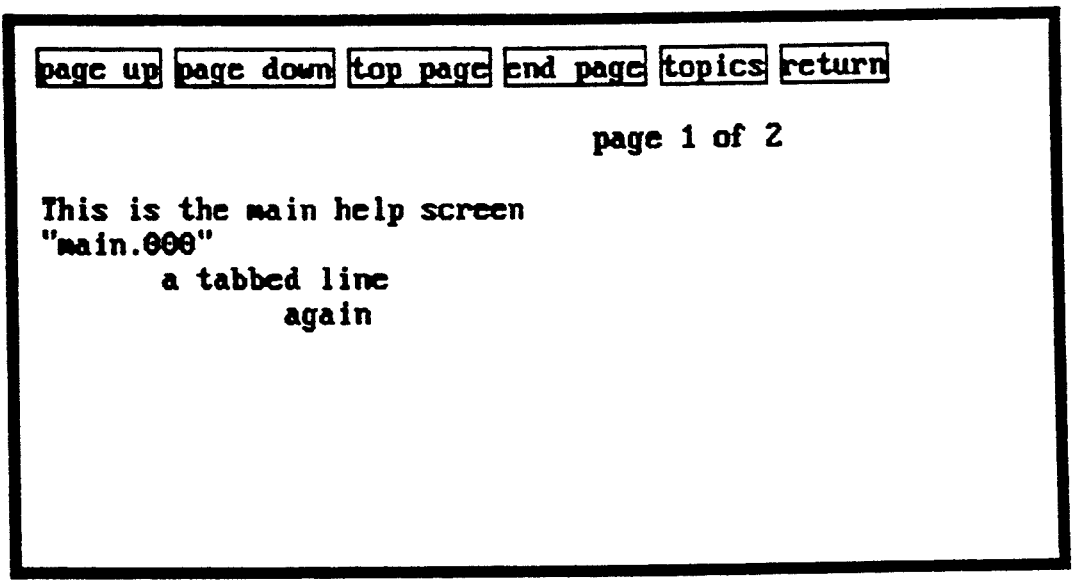
Figure 16W:
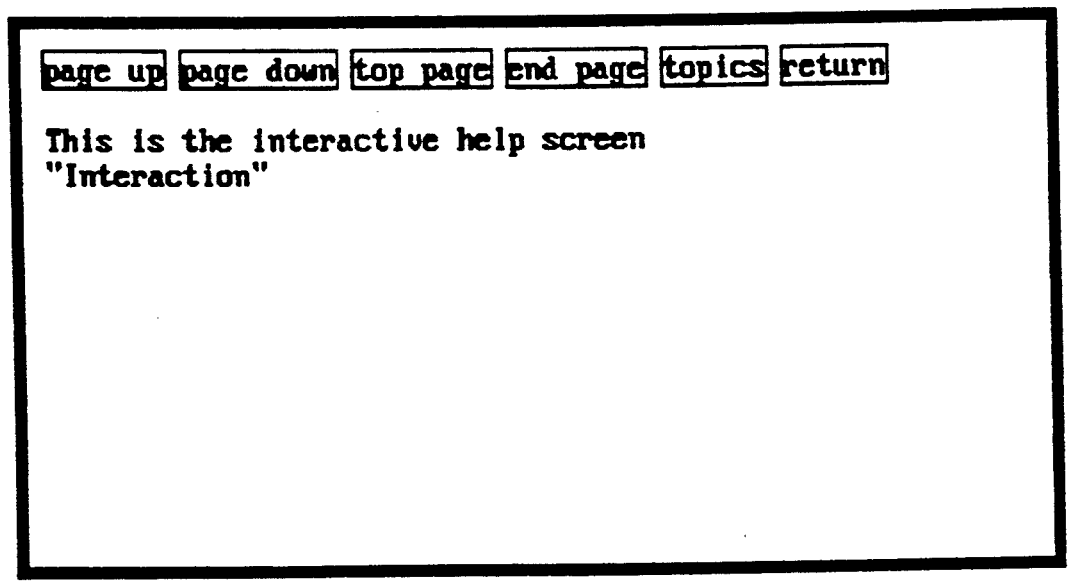

Referring to FIGS. 16V and 16W, Help may be obtained at any time by pressing the F1 key. As shown, the help given can be context-sensitive, that is, it may explain the commands currently available to the user and include other explanatory information.

Figure 16X:
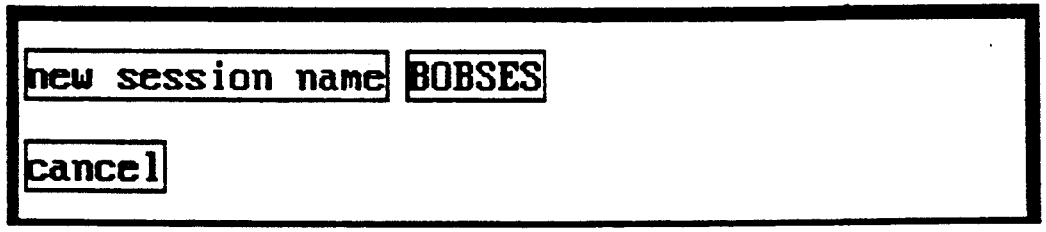

Referring to FIG. 16X, selecting Save and Run from the application editing window (FIG. 16C) prompts the user for a name of the resulting session. The user can also cancel the command by clicking on the Cancel box.

Figure 16Y:
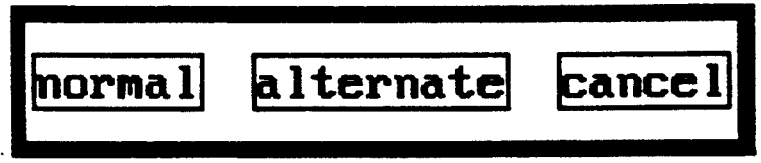
Figure 16Z:
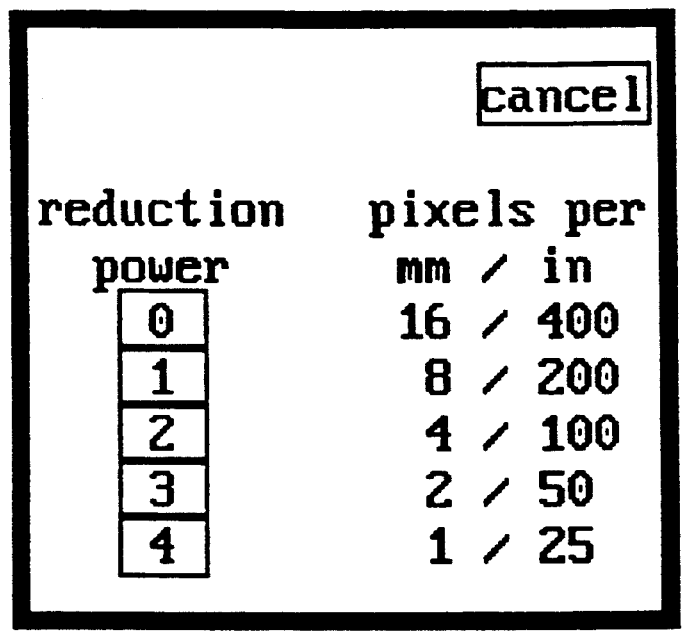
Figure 16A:
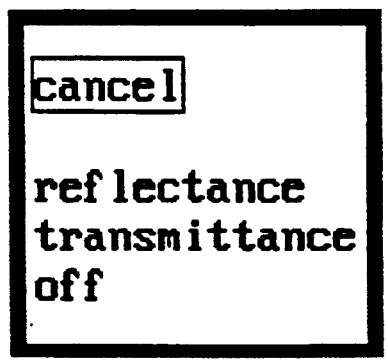

Referring to FIGS. 16Y through 16AA, the data storage density (FIG. 16Y), x or y axis reduction power (FIG. 16Z), or lamps (FIG. 16AA) in the Scan Sample parameters menu (FIG. 16G) are selected by choosing items from the respective menus.

Selecting Utilities from the main window (FIG. 16A) creates a menu of file managing utilities that allow the user to copy, move, delete and back-up a file or group of files.

Selecting Exit from the main window (FIG. 16A) exits the program.

Selecting Display Image from the select action window (FIG. 16F) presents a tree of the application, indicating those images which can be displayed, and allows the user to select one.

Selecting Display Spots from the select action window (FIG. 16F) lists the spot display parameter files that currently defined, and allows the user to select one.

METHOD

There follows an example of use of the above described system for analysis of an autoradiogram representing products of a DNA sequencing reaction. This autoradiogram may be produced by any standard procedure. It is particularly desirable to produce an autoradiogram which results from a DNA sequencing reaction performed using a manganese buffer rather than a magnesium buffer. In this way more than one of the normal four samples may be run within a lane. For example, the sequencing reaction is performed in the manganese based buffer and a mixture of two or more chain terminating agents, e.g., dideoxy chain terminating agents. These chain terminating agents are provided at different concentrations to cause production of different concentrations of DNA products in the sequencing reaction. In this way the bands produced in the resulting autoradiogram will be of different density; the density of each band representing the nucleotide base at the end of the DNA product. Thus, the density of a band may be used to determine the sequence of nucleotide bases along a DNA molecule. If desired, all four dideoxy nucleotide bases may be provided in a sequencing reaction, thereby producing four different densities of bands. The scanner of the present invention is able to analyze a single lane and determine the relative densities of each band and thence the nucleotide base which corresponds to each position along the DNA molecule.

In general, the autoradiograph produced from a DNA sequencing reaction is placed on sample bed 20 at a location where the first DNA bands to be analyzed are located in a position which the computer recognizes as the base or start position. Sample clamps 34 are moved to accommodate the appropriate width of sample to be analyzed, and clamped in position such that the autoradiographic film is clamped between drive shaft 28 and rollers 36. The host computer is then controlled as described above and the sample caused to move over the sample slot in order to allow a determination of the densities of various parts of the autoradiographic film. The information is collected by the CCD device and relayed to the host computer. This information is then analyzed as described above.

Referring to FIG. 17A, in the method used to display information to the user, software tools providing general processing functionality are stored 700. Next 710, an interpretive program is supplied so that, 720, the user may interactively specify a sequence of the tools to be executed (e.g., an application).

Referring to FIG. 17B, later, the user may run an application to establish a session 730, at which time a copy of the application is copied to the session 740, and a copy of any auxiliary data is also copied 750. After 760 the session is finished, the state of the application as well as any auxiliary data is stored 770 under the session, so that later 780 the session may be resumed from this stored state.

APPENDIX A: SYNOPSIS OF ROUTINES IN APPENDIX B

The source code in microfiche Appendix B may be compiled and run on any DOS operating system computer having a 80286 or 80386 microprocessor. The software is organized into several categories:

The files with the .C or .H extensions are C language programs and data files that, when compiled, form the "tools" that may be called by applications. These files are written in the C language, and may be compiled by the Microsoft C compiler, version 5.1, available from Microsoft Inc., 16011 NE 36th Way, Box 97017, Redmond, Wash., 98073-9717.

The files with .CLF (command language file) extensions describe applications, and list a sequence of tools to be invoked by the applications.

The files with the .MPL (menu parameter list) extensions describe menu configurations for the .CLF files.

The files named DEFAULT.* describe an initial sequence of tools to be invoked by applications.

The two .ASM files contain assembly code for performing low-level functions. The 3710DRV.ASM file is a TSR program for the host PC SCSI interface. The 3710.ASM file contains the controlling microprogram for the scanner microprocessor (it is resident in the scanner). These files are written for the Microsoft Macro Assembler, version 5.1, available from Microsoft Inc. at the above address.

One important tool for operating the system is the Spot Find tool. Spot Find breaks the image into packets along the x axis and stores these packets in a linked-list data structure. These packets are then combined and processed in the y direction. Using the Spot Find parameters, the user is able to adjust the sensitivity and minimum and maximum intensities. Combining in the y-direction overcomes problems associated with "smiling".

The scanned pixel data is stored in database files managed by the FoxBase+2.00 database server, available from Fox Software, 27493 Holiday Lane, Perrysburg, Ohio 43551.

What is claimed is:

1. In a data processing system comprising a computer, an image scanner, and a natural language interface responsive to user input of natural language identifiers, a method for creating and executing a custom application computer program comprising a sequence of user-specified software tools for scanning and analyzing an image comprising four vertical sections, each section containing zero or more horizontal bands with non-uniform perimeters, said method comprising the computer-implemented steps of:
   storing a plurality of said software tools for directing the performance of said scanning and analysis of said image;
   creating a custom application computer program by storing a user-defined sequence of software tools using said natural language identifiers, to be executed for scanning and analyzing said image;
   executing said custom application computer program to scan said image and store data relating to said scanned image; and
   executing said custom application computer program to use said stored data to locate said horizontal bands with non-uniform perimeters in each of said four vertical sections and to correlate each of said horizontal bands with non-uniform perimeters to a predetermined shape.

* * * * *